United States Patent
Ishikawa et al.

(10) Patent No.: US 11,220,677 B2
(45) Date of Patent: Jan. 11, 2022

(54) HEAT-RESISTANT REVERSE TRANSCRIPTASE MUTANT

(71) Applicant: TAKARA BIO INC., Shiga (JP)

(72) Inventors: Kazuhiko Ishikawa, Sakai (JP); Takashi Uemori, Otsu (JP); Nariaki Takatsu, Kusatsu (JP)

(73) Assignee: TAKARA BIO INC., Shiga (JP)

(*) Notice: Subject to any disclaimer, the term of this patent is extended or adjusted under 35 U.S.C. 154(b) by 341 days.

(21) Appl. No.: 16/466,352

(22) PCT Filed: Dec. 13, 2017

(86) PCT No.: PCT/JP2017/044693
§ 371 (c)(1),
(2) Date: Jun. 4, 2019

(87) PCT Pub. No.: WO2018/110595
PCT Pub. Date: Jun. 21, 2018

(65) Prior Publication Data
US 2021/0277367 A1   Sep. 9, 2021

(30) Foreign Application Priority Data

Dec. 14, 2016 (JP) .............................. JP2016-242171

(51) Int. Cl.
| C12N 9/12 | (2006.01) |
| C12N 15/52 | (2006.01) |
| C12Q 1/686 | (2018.01) |
| C12N 15/09 | (2006.01) |

(52) U.S. Cl.
CPC ........... *C12N 9/1276* (2013.01); *C12N 15/52* (2013.01); *C12Q 1/686* (2013.01); *C12Y 207/07049* (2013.01)

(58) Field of Classification Search
None
See application file for complete search history.

(56) References Cited

U.S. PATENT DOCUMENTS

| 2002/0090618 A1 | 6/2002 | Smith et al. |
| 2008/0227661 A1 | 9/2008 | Hogrefe et al. |
| 2011/0065606 A1 | 3/2011 | Janulaitis et al. |
| 2013/0143225 A1 | 6/2013 | Yasukawa et al. |

FOREIGN PATENT DOCUMENTS

| JP | 2004-511211 | 4/2004 |
| JP | 4193079 | 12/2008 |
| JP | 2009-504162 | 2/2009 |
| JP | 2011-516072 | 5/2011 |
| WO | 2004/024749 | 3/2004 |
| WO | 2007/022045 | 2/2007 |
| WO | 2009/125006 | 10/2009 |
| WO | 2012/020759 | 2/2012 |
| WO | 2012/108672 | 8/2012 |
| WO | 2015/112767 | 7/2015 |

OTHER PUBLICATIONS

Airaksinen et al. (Nucleic Acids Research, 1998, vol. 26 No. 2, p. 576-581).*
Folz et al. (Journal of Biological Chemistry, vol. 263, No. 4, Feb. 5, 1988, p. 2070-2078).*
Office Action dated Oct. 5, 2021 in corresponding Japanese Patent Application No. 2018-556717, with English Machine Translation, 13 pages.
Hisayoshi, et al. "Amino acid substitutions away from the RNase H catalytic site increase the thermal stability of MMLV reverse transcriptase through RNase H inactivation", Annual Meeting of the Japan Society for Bioscience, Biotechnology, and Agrochemistry, 2015, p. 4C22p03, 3 pages.
Extended European Search Report dated Jul. 21, 2020 issued in corresponding European Patent Application No. 17880765.7, 7 pages.
International Search Report dated Mar. 13, 2018 in International Application No. PCT/JP2017/044693.
Written Opinion of the International Searching Authority dated Mar. 13, 2018 in International Application No. PCT/JP2017044693.
International Preliminary Report on Patentability dated Jun. 18, 2019 in International Application No. PCT/JP2017/044693.
Hisayoshi et al., thermostabilization of MMLV reverse transcriptase and disappearance of RNase H activity due to amino acid mutation to side away from the RNase H catalytic site, Annual Meeting of the Japan Society for Bioscience, Biotechnology, and Agrochemisty, 2015.

* cited by examiner

*Primary Examiner* — Suzanne M Noakes
*Assistant Examiner* — Jae W Lee
(74) *Attorney, Agent, or Firm* — Wenderoth, Lind & Ponack, L.L.P.

(57) ABSTRACT

Provided are: a reverse transcriptase mutant including an amino acid mutation at a position corresponding to position 55 of the amino acid sequence of wild-type reverse transcriptase derived from the Moloney murine leukemia virus, wherein the reverse transcriptase mutant is characterized in that the amino acid mutation is a substitution from threonine to another amino acid, and the other amino acid is selected from the group consisting of amino acids having a nonpolar aliphatic side chain and amino acids having a polar acidic functional group side chain; a nucleic acid that encodes the mutant; a method for producing the mutant and the nucleic acid that encodes the mutant; a method for synthesizing cDNA in which the mutant is used; and a composition and kit including the mutant.

6 Claims, No Drawings
Specification includes a Sequence Listing.

HEAT-RESISTANT REVERSE TRANSCRIPTASE MUTANT

TECHNICAL FIELD

The present invention relates to heat-resistant reverse transcriptase mutants. Furthermore, the present invention relates to a method for increasing the heat-resistance of existing reverse transcriptases, and a method for producing the heat-resistant reverse transcriptase mutants.

BACKGROUND ART

Reverse transcriptases (RTase) generally have RNA-dependent DNA polymerase activity, which is an activity for synthesizing cDNA from a template RNA, and ribonuclease H (RNase H) activity, which is an activity for degrading the RNA chain of an RNA/DNA hybrid.

Since reverse transcriptases have RNA-dependent DNA polymerase activity, they can be used for sequencing of mRNA which directly reflects the amino acid sequence of a protein expressed in a living organism, construction of cDNA libraries, RT-PCR and the like. For these uses, reverse transcriptases produced by Moloney murine leukemia virus or avian myeloblastosis virus are often used.

Thus reverse transcriptases have various uses. However, there are various problems caused due to template RNA. For example, in the case where mRNA has a nucleotide sequence that easily forms a secondary structure, cDNA synthesis from the mRNA as a template by using a reverse transcriptase may be hindered by the secondary structure. To solve this problem, raising the temperature of reverse transcription reaction is effective. However, the reverse transcriptases produced from Moloney murine leukemia virus or avian myeloblastosis virus have poor resistance to heat, and they are inactivated under such a temperature condition that suppresses the secondary structure formation of RNA. Therefore, reverse transcriptase mutants having increased heat resistance have been proposed (see, for example, Patent Literatures 1 to 6).

CITATION LIST

Patent Literatures

Patent literature 1: JP 4193079 A
Patent literature 2: WO2004/024749
Patent literature 3: WO2007/022045
Patent literature 4: WO2009/125006
Patent literature 5: WO2012/108672
Patent literature 6: WO2015/112767

SUMMARY OF INVENTION

Problem to be Solved by the Invention

However, development of additional heat-resistant reverse transcriptases is still desired. An object of the present invention is to provide heat-resistant reverse transcriptase mutants.

Solutions to the Problems

As a result of intensive studies to develop heat-resistant reverse transcriptase mutants, the present inventors surprisingly found that a reverse transcriptase having heat-resistance was obtained by replacing threonine at position 55 in the amino acid sequence of a reverse transcriptase produced from Moloney murine leukemia virus (hereinafter sometimes referred to as MMLV), which had never been mutated and was believed to be involved in stabilization of loop structure, with a different amino acid selected from the group consisting of amino acids having non-polar aliphatic side chains, amino acids having polar acidic functional group side chains, amino acids having polar basic functional group side chains, and amino acids having polar hydroxy aliphatic side chains. Furthermore, they found that the heat-resistance of a known reverse transcriptase was further increased by combining the amino acid mutation at position 55 with the known amino acid mutation of the known heat-resistant reverse transcriptase. Furthermore, they found that a reverse transcriptase having further increased heat resistance was obtained by combining the amino acid mutation at position 55 with a different novel amino acid mutation. Thus, the present invention was completed.

Specifically, the present invention is characterized by a replacement(s) of an amino acid(s) in a range of position 53 to position 56 to stabilize the steric structure of loop structure in the amino acid sequence of a wild-type Moloney murine leukemia virus reverse transcriptase. The first aspect of the present invention relates to, but not limited to, a reverse transcriptase mutant comprising an amino acid mutation at a position corresponding to position 55, wherein the amino acid mutation is a replacement of threonine with a different amino acid and the different amino acid is selected from the group consisting of amino acids having non-polar aliphatic side chains, amino acids having polar acidic functional group side chains, amino acids having polar basic functional group side chains, and amino acids having polar hydroxy aliphatic side chains. In the reverse transcriptase mutant as the first aspect of the present invention, the amino acid mutation may be a replacement of threonine with a different amino acid selected from the group consisting of amino acids having non-polar aliphatic side chains and amino acids having polar acidic functional group side chains. Further, in the reverse transcriptase mutant as the first aspect of the present invention, the amino acid mutation may be a replacement of threonine with a different amino acid selected from the group consisting of amino acids having non-polar aliphatic side chains, amino acids having polar basic functional group side chains, and amino acids having polar hydroxy aliphatic side chains.

As an example, in the reverse transcriptase mutant as the first aspect of the present invention, the amino acid mutation is a replacement of threonine with glycine or aspartic acid. The reverse transcriptase mutant as the first aspect of the present invention may further comprise one or more amino acid replacements selected from the group consisting of the following (1) to (8):
(1) A54P,
(2) T287K,
(3) Q291K,
(4) T306K,
(5) D524A,
(6) D524N,
(7) H204R, M289L, T306K and F309N, and
(8) D209P and I212A.

The present invention includes reverse transcriptase mutants comprising the above-mentioned amino acid replacement at position 55 and the above-mentioned amino acid replacement (1) at position 54 in combination with one or more amino acid replacements selected from the group consisting of the above-mentioned amino acid replacements (2) to (8). Further, the reverse transcriptase mutant as the first aspect of the present invention may lack ribonuclease H activity.

It was found that the above-mentioned amino acid replacement (3) at position 291 and the above-mentioned amino acid replacement (8) at position 209 and position 212 were involved in heat-resistance for the first time in the present invention. For example, a reverse transcriptase mutant comprising the amino acid replacement of glutamine with lysine at position 291 or the amino acid replacements of aspartic acid with proline at position 209 and isoleucine with alanine at position 212 in the amino acid sequence of a wild-type MMLV reverse transcriptase has increased heat-resistance as compared with the wild-type MMLV reverse transcriptase. Therefore, these amino acid replacements may be combined with the above-mentioned amino acid replacement at position 55 in the present invention.

The second aspect of the present invention relates to a nucleic acid encoding the reverse transcriptase mutant described as the first aspect of the present invention.

The third aspect of the present invention relates to an expression vector comprising the nucleic acid described as the second aspect of the present invention and an expression regulatory sequence.

The fourth aspect of the present invention relates to a cell which is transformed with the expression vector described as the third aspect of the present invention and which expresses a reverse transcriptase mutant.

The fifth aspect of the present invention relates to a method for producing a nucleic acid encoding a reverse transcriptase mutant, the method comprising a step of replacing a codon encoding threonine at a position corresponding to position 55 of the amino acid sequence of a wild-type MMLV reverse transcriptase in a nucleic acid encoding a MMLV reverse transcriptase, with a codon encoding an amino acid selected from the group consisting of amino acids having non-polar aliphatic side chains, amino acids having polar acidic functional group side chains, amino acids having polar basic functional group side chains, and amino acids having polar hydroxy aliphatic side chains. In the fifth aspect of the present invention, the codon encoding threonine may be replaced with a codon encoding an amino acid selected from the group consisting of amino acids having nonpolar aliphatic side chains and amino acids having polar acidic functional group side chains.

In the fifth aspect of the invention, the nucleic acid encoding a MMLV reverse transcriptase may be a nucleic acid encoding a wild-type MMLV reverse transcriptase or a mutant thereof.

In the fifth aspect of the present invention, the nucleic acid encoding a MMLV reverse transcriptase may be a nucleic acid encoding a reverse transcriptase mutant comprising one or more amino acid replacements selected from the group consisting of the following (1) to (8):
(1) A54P,
(2) T287K,
(3) Q291K,
(4) T306K,
(5) D524A,
(6) D524N,
(7) H204R, M289L, T306K and F309N, and
(8) D209P and I212A.

The sixth aspect of the present invention relates to a method for producing a heat-resistant reverse transcriptase mutant, the method comprising a step of replacing threonine at a position corresponding to position 55 of the amino acid sequence of a wild-type MMLV reverse transcriptase, with a different amino acid selected from the group consisting of amino acids having non-polar aliphatic side chains, amino acids having polar acidic functional group side chains, amino acids having polar basic functional group side chains, and amino acids having polar hydroxy aliphatic side chains. In the method of the sixth aspect of the present invention, the threonine may be replaced with an amino acid selected from the group consisting of amino acids having nonpolar aliphatic side chains and amino acids having polar acidic functional group side chains.

The seventh aspect of the present invention relates to a method for synthesizing cDNA, the method comprising a step of synthesizing a DNA complementary to a template RNA using the reverse transcriptase mutant described as the first aspect of the present invention. Further, the method may include a step of amplifying the cDNA. Further, in the method, amplification of the cDNA may be carried out by isothermal amplification reaction or PCR.

The eighth aspect of the present invention relates to a composition comprising the reverse transcriptase mutant described as the first aspect of the present invention.

The ninth aspect of the present invention relates to a kit comprising the reverse transcriptase mutant described as the first aspect of the present invention.

The tenth aspect of the present invention relates to a method for increasing heat resistance of a reverse transcriptase, the method comprising a step of replacing threonine at a position corresponding to position 55 of the amino acid sequence of a wild-type MMLV reverse transcriptase, with a different amino acid selected from the group consisting of amino acids having non-polar aliphatic side chains, amino acids having polar acidic functional group side chains, amino acids having polar basic functional group side chains, and amino acids having polar hydroxy aliphatic side chains. Further, provided is a method for increasing heat resistance of a reverse transcriptase, the method comprising a step of replacing a codon encoding threonine at a position corresponding to position 55 of the amino acid sequence of a wild-type MMLV reverse transcriptase in a nucleic acid encoding a MMLV reverse transcriptase, with a codon encoding an amino acid selected from the group consisting of amino acids having non-polar aliphatic side chains and amino acids having polar acidic functional group side chains.

Effects of the Invention

The present invention provides a heat-resistant reverse transcriptase mutant and a method for producing the mutant. According to the present invention, a heat-resistant reverse transcriptase mutant is provided by replacing threonine at a position corresponding to position 55 of the amino acid sequence of a wild-type MMLV reverse transcriptase with a different amino acid. In addition, the heat resistance of a known heat-resistant reverse transcriptase is further increased by replacing threonine at the position corresponding to position 55 of the amino acid sequence of a wild-type MMLV reverse transcriptase with another amino acid. Such an amino acid replacement that produces effect of further increasing the heat-resistance of known heat-resistant reverse transcriptases has been found by the present invention for the first time. In addition, the heat-resistant reverse transcriptase mutant of the present invention has increased heat-resistance while the properties of reverse transcriptase, such as RNA binding activity, cDNA elongation activity, and cDNA elongation rate are not affected.

MODE FOR CARRYING OUT THE INVENTION

As used herein, "heat resistance" refers to a property of retaining enzyme activity even after heating treatment. For example, when an enzyme that usually loses 50% of its activity by treatment at 40° C. for 5 minutes retains 50% or more of the activity even after treatment at 50° C. or more, 60° C. or more, or 70° C. or more for 5 minutes, the enzyme has increased "heat resistance". Such an enzyme having increased heat resistance can be subjected to reaction at higher temperature. For example, in the case of using a Moloney murine leukemia virus reverse transcriptase, since the optimum temperature of the wild-type enzyme is in a range of 37 to 42° C., a reverse transcriptase mutant that retains the enzyme activity at for example 43° C. or more, preferably 45° C. or more, more preferably 50° C. or more is "heat resistant" or "has increased heat resistance".

As used herein, "residual activity" refers to enzyme activity remaining after heating treatment. The "residual activity rate" also refers to a rate (%) of enzyme activity remaining after heating treatment when the enzyme activity of a protein untreated with heat (an unheated protein) is 100%.

Amino acid numbers (or amino acid positions) as used herein are represented by numbers when methionine encoded by the initiation codon is not counted. Thus, when the first methionine is counted, one should be added to the amino acid numbers described herein.

Hereinafter, the present invention will be explained in detail.

1. Heat-Resistant Reverse Transcriptase Mutant of the Present Invention

The first aspect of the present invention relates to a heat-resistant reverse transcriptase mutant, that is, a mutant of a reverse transcriptase which has acquired heat resistance (or has increased heat resistance). The reverse transcriptase mutant is characterized by comprising a mutation to change a steric structure ranging from position 53 to position 56, which corresponds to a loop structure portion in the wild-type Moloney murine leukemia virus reverse transcriptase, into a more stable structure in the amino acid sequence of the wild-type MMLV reverse transcriptase or a mutant thereof. For example, the reverse transcriptase mutant is characterized by comprising a replacement of threonine at a position corresponding to position 55 of the wild-type amino acid sequence with an amino acid to stabilize the steric structure of loop structure in the reverse transcriptase, such as an amino acid selected from the group consisting of amino acids having nonpolar aliphatic side chains and amino acids having polar acidic functional group side chains. In other words, the "amino acids having nonpolar aliphatic side chains" are nonpolar and hydrophobic amino acids, and examples thereof include isoleucine, leucine, valine, glycine, proline and alanine. The "amino acids having polar acidic functional group side chains" are amino acids having carboxylic acid groups, and examples thereof include aspartic acid and glutamic acid. It is particularly preferable that the amino acid mutation in the reverse transcriptase mutant of the present invention is an amino acid replacement of threonine with glycine or aspartic acid.

From the viewpoint of replacement with an amino acid to stabilize a steric structure, for example, the reverse transcriptase mutant of the present invention comprises an amino acid mutation at a position corresponding to position 55 of the amino acid sequence of the wild-type MMLV reverse transcriptase, wherein the amino acid mutation is a replacement of threonine with a different amino acid and the different amino acid is selected from the group consisting of amino acids having nonpolar aliphatic side chains, amino acids having polar acidic functional group side chains, amino acids having polar basic functional group side chains and amino acids having polar hydroxy aliphatic side chains. Preferably, the reverse transcriptase mutant of the present invention comprises an amino acid mutation at a position corresponding to position 55 of the amino acid sequence of the wild-type MMLV reverse transcriptase, wherein the amino acid mutation is a replacement of threonine with a different amino acid and the different amino acid is selected from the group consisting of amino acids having nonpolar aliphatic side chains and amino acids having polar acidic functional group side chains. Examples of the "amino acids having polar basic functional group side chains" include arginine and lysine. Examples of the "amino acid having polar hydroxy group aliphatic side chains" include serine.

The reverse transcriptase mutant of the present invention may be a reverse transcriptase mutant comprising an amino acid mutation at a position corresponding to position 55 of the amino acid sequence of the wild-type MMLV reverse transcriptase, wherein the amino acid mutation is a replacement of threonine with a different amino acid and the different amino acid is selected from the group consisting of amino acids having nonpolar aliphatic side chains, amino acids having polar basic functional group side chains and amino acids having polar hydroxy aliphatic side chains. For example, the amino acid mutation may be a replacement of threonine with glycine, arginine, lysine or serine.

For example, the reverse transcriptase mutant of the present invention may be a reverse transcriptase mutant comprising an amino acid mutation at a position corresponding to position 55 of the amino acid sequence of the wild-type MMLV reverse transcriptase, wherein the amino acid mutation is a replacement of threonine to a different amino acid and the different amino acid is an amino acid selected from the group consisting of isoleucine, leucine, valine, glycine, proline, alanine, aspartic acid, glutamic acid, arginine, lysine and serine. As a further example, the different amino acid may be an amino acid selected from the group consisting of glycine, aspartic acid, lysine and serine.

As used herein, the "position corresponding to position 55 of the amino acid sequence of a wild-type MMLV reverse transcriptase" refers to a position relating to the steric structure of loop structure in the wild-type MMLV reverse transcriptase, and specifically means position 55 in an amino acid sequence or a position in the amino acid sequence of a MMLV reverse transcriptase mutant which corresponds to position 55 in the amino acid sequence of the wild-type MMLV reverse transcriptase. The "position in the amino acid sequence of a MMLV reverse transcriptase mutant which corresponds to position 55 in the amino acid sequence of the wild-type MMLV reverse transcriptase" can be easily determined by comparing or aligning the amino acid sequence of the mutant with the amino acid sequence of the wild-type, for example, using a known algorithm etc. Similarly, an amino acid position as used herein refers to an amino acid position in the amino acid sequence of a wild-type, and includes a position in the amino acid sequence of a mutant which corresponds to the amino acid position in the amino acid sequence of the corresponding wild-type. Examples of a position corresponding to position 55 of the wild-type amino acid sequence include, but not limited to, positions in a range from position 53 to position 56 in the amino acid sequence of a mutant.

The reverse transcriptase mutant of the present invention may comprise the amino acid replacement of threonine at the "position corresponding to position 55 of the amino acid sequence of a wild-type MMLV reverse transcriptase" (hereinafter also referred to as "the amino acid replacement at position 55") as well as a mutation(s) at an amino acid position(s) other than position 55 (hereinafter also referred to as the "mutation at a different amino acid position"). The mutation at a different amino acid position may be an amino acid replacement, an amino acid insertion or an amino acid deletion. The reverse transcriptase mutant of the present invention may comprise two or more mutations at different amino acid positions. The mutation at a different amino acid position is not particularly limited, and may be any amino acid mutation.

Examples of the mutation at a different amino acid position include, but not limited to, mutations for imparting heat resistance, mutations for increasing heat resistance, and amino acid mutations for improving the properties of reverse transcriptase. For example, when the reverse transcriptase mutant of the present invention comprises the amino acid replacement at position 55 in combination with a mutation for imparting or increasing heat resistance as the mutation at a different amino acid position, the heat resistance is further increased.

Preferable examples of the mutation at a different amino acid position include, but not limited to, an amino acid replacement and combinations of amino acid replacements as shown in the following (1) to (8):
(1) A54P,
(2) T287K,
(3) Q291K,
(4) T306K,
(5) D524A,
(6) D524N,
(7) H204R, M289L, T306K and F309N, and
(8) D209P and I212A.

Among the above-mentioned mutations at different amino acid positions, the above-mentioned amino acid replacement (3) at position 291 and the above-mentioned amino acid replacement (8) at position 209 and position 212 were found to be involved in heat-resistance for the first time in the present invention. For example, a reverse transcriptase mutant comprising the amino acid replacement of glutamine with lysine at position 291 or the amino acid replacements of aspartic acid with proline at position 209 and isoleucine with alanine at position 212 in the amino acid sequence of the wild-type MMLV reverse transcriptase has increased heat-resistance as compared with the wild-type MMLV reverse transcriptase. Therefore, a reverse transcriptase having further increased heat resistance can be obtained by combining such mutation(s) at a different amino acid position(s) with the amino acid replacement at position 55 of the present invention.

For example, the reverse transcriptase mutant of the present invention may comprise, in addition to the amino acid replacement at position 55, one or more amino acid replacements or combinations of amino acid replacements selected from the above-mentioned amino acid replacements (1) to (8). For example, a reverse transcriptase mutant comprising the amino acid replacement at position 55 and the above-mentioned amino acid replacement (1) at position 54 as well as one or more amino acid replacements or combinations of amino acid replacements selected from the above-mentioned amino acid replacements (2) to (8) is also included in the present invention. Examples of such a reverse transcriptase mutant include a reverse transcriptase mutant comprising the amino acid replacement of alanine at position 54 with proline and the amino acid replacement of threonine at position 55 with glycine in combination with one or more amino acid replacements selected from the above-mentioned amino acid replacements (2) to (8).

The reverse transcriptase mutant of the present invention may further comprise a mutation that deletes RNase H activity. Examples of the RNase H activity-deletion mutation include, but not limited to, a replacement of aspartic acid at position 583 and/or position 524 with a different amino acid, and a mutation to delete an RNase H active domain. Thus, the present invention provides a reverse transcriptase mutant having heat-resistance and lacking RNase H activity. Such a mutant is suitably used in reverse transcription reaction using RNA as a template.

Examples of the reverse transcriptase mutant of the present invention include, but not limited to, a mutant comprising an amino acid sequence (SEQ ID NO: 2) in which threonine at position 55 is replaced with glycine in the wild-type amino acid sequence of SEQ ID NO: 1, and a protein comprising an amino acid sequence (SEQ ID NO: 3) in which threonine at position 55 is replaced with aspartic acid in the wild-type amino acid sequence of SEQ ID NO: 1. Further examples of the reverse transcriptase mutant of the present invention include a mutant consisting of the amino acid sequence shown in SEQ ID NO: 2 and a mutant consisting of the amino acid sequence shown in SEQ ID NO: 3. Additional examples of the reverse transcriptase mutant of the present invention include, but not limited to, mutants comprising any amino acid sequence of SEQ ID NOs: 4 to 10, 39 to 44, 52, and 55 to 62. Further examples of the reverse transcriptase mutant of the present invention include mutants consisting of any amino acid sequence of SEQ ID NOs: 4 to 10, 39 to 44, 52, and 55 to 62. The above-mentioned amino acid sequences may comprise other mutations for further improving heat resistance, mutations for improving the properties of reverse transcriptase, and the like.

Furthermore, examples of the reverse transcriptase mutant of the present invention include mutants having heat-resistance and comprising an amino acid sequence having at least 80%, for example, at least 85%, at least 90%, at least 95%, at least 98% or at least 99% identity with SEQ ID NO: 1, wherein threonine at a position corresponding to position 55 in the amino acid sequence is replaced with a different amino acid selected from the group consisting of amino acids having nonpolar aliphatic side chains, amino acids having polar acidic functional group side chains, amino acids having polar basic functional group side chains, and amino acids having polar hydroxy group aliphatic side chains, for example, glycine or aspartic acid. Further examples of the reverse transcriptase mutant of the present invention include mutants having heat-resistance and consisting of an amino acid sequence having at least 80%, for example, at least 85%, at least 90%, at least 95%, at least 98% or at least 99% identity with SEQ ID NO: 1, wherein threonine at a position corresponding to position 55 in the amino acid sequence is replaced with a different amino acid selected from the group consisting of amino acids having nonpolar aliphatic side chains, amino acids having polar acidic functional group side chains, amino acids having polar basic functional group side chains, and amino acids having polar hydroxy group aliphatic side chains, for example, glycine or aspartic acid.

The reverse transcriptase mutant of the present invention exhibits activity even under a temperature condition of 40°

C. or higher, for example, 45° C. or higher, 50° C. or higher, 55° C. or higher, or 60° C. or higher whereas the wild-type reverse transcriptase exhibits activity at 37° C. to 42° C. For example, the reverse transcriptase mutant of the present invention exhibits high activity even at a high temperature range of 50 to 55° C. as compared with the wild-type, and also has high residual activity after being maintained at the high temperature range as compared with the wild-type.

The reverse transcriptase mutant of the present invention has heat-resistance and retains the properties of reverse transcriptase, such as RNA binding activity, cDNA elongation activity and the like. In other words, the "amino acid replacement at position 55" imparts heat resistance to a reverse transcriptase, but does not affect the properties of the reverse transcriptase, such as RNA binding activity, cDNA elongation activity, and cDNA elongation rate.

The reverse transcriptase mutant of the present invention has further increased heat-resistance when it comprises the amino acid replacement at position 55 in combination with other mutations for thermostabilization.

Furthermore, the reverse transcriptase mutant of the invention may comprise an affinity tag to facilitate purification of an expressed polypeptide. The reverse transcriptase mutant of the present invention may comprise a peptide or polypeptide such as an affinity tag, for example, at the N-terminus or C-terminus, as long as the reverse transcriptase activity and the peculiar heat-resistance are maintained. Such a tag is useful for preparation of the mutant. Examples of the tag include known tags such as a histidine tag consisting of 4 to 8 consecutive His residues, a Flag tag, an HA tag, a c-myc tag, and a GST tag. The tag may be linked to the mutant of the present invention via a linker comprising 1-15 amino acids, if desired.

2. Nucleic Acid Encoding Heat-Resistant Reverse Transcriptase Mutant of the Present Invention According to the present invention, a nucleic acid encoding a heat-resistant reverse transcriptase mutant is provided. Specifically, a nucleic acid encoding the reverse transcriptase mutant of the present invention as described above is provided.

Examples of the nucleic acid encoding the reverse transcriptase mutant of the present invention include, but not limited to, nucleic acids comprising nucleotide sequences encoding any amino acid sequence of SEQ ID NOs: 2 to 10, 39 to 44, 52, and 55 to 62. Further examples of the nucleic acid encoding the reverse transcriptase mutant of the present invention include nucleic acids consisting of nucleotide sequences encoding any amino acid sequence of SEQ ID NOs: 2 to 10, 39 to 44, 52, and 55 to 62. More preferably, examples of the nucleic acid encoding the reverse transcriptase mutant of the present invention include nucleic acids comprising nucleotide sequences encoding any amino acid sequence of SEQ ID NOs: 12 to 20, 45 to 50, 54, and 63 to 70. Further examples of the nucleic acid encoding the reverse transcriptase mutant of the present invention include nucleic acids consisting of nucleotide sequences encoding any amino acid sequence of SEQ ID NOs: 12 to 20, 45 to 50, 54, and 63 to 70. The nucleic acid may further comprise a different nucleic acid mutation for imparting or increasing heat-resistance or a nucleic acid mutation for improving the properties of reverse transcriptase.

The nucleic acid encoding the reverse transcriptase mutant of the present invention is not particularly limited as long as it is composed of codons encoding a protein that can be expressed in a host to be used and has reverse transcriptase activity. The codons may be optimized to allow expression in the host or to increase the expression level. The codon optimization is preferably performed by a method usually used in the art.

3. Expression Vector Comprising Nucleic Acid Encoding Heat-resistant Reverse Transcriptase Mutant of the Present Invention The expression vector of the present invention preferably comprises a nucleic acid encoding the reverse transcriptase mutant of the present invention and an expression regulatory sequence operably linked to the nucleic acid.

An expression vector into which the nucleic acid encoding the reverse transcriptase mutant of the present invention will be inserted is not particularly limited, and may be any expression vector usually used in the art. A vector capable of autonomously replicating in a host cell or a vector that can be integrated into a host chromosome may be used. A vector compatible with a host may be used.

Examples of the expression vector into which the nucleic acid encoding the reverse transcriptase mutant of the present invention will be inserted include a plasmid vector, a phage vector, a virus vector and the like. As the plasmid vector, a plasmid suitable for a host to be used, for example, a plasmid derived from *E. coli*, a plasmid derived from *Bacillus* bacteria, or a plasmid derived from yeast is well known to a person skilled in the art. Many plasmid vectors are commercially available. In the present invention, these known plasmids and altered plasmids from the known plasmids can be used. As the phage vector, for example, λ phage (for example, Charon 4A, Charon 21A, EMBL3, EMBL4, λgt10, λgt11, λZAP) and the like can be used. As the virus vector, for example, an animal virus such as retrovirus or vaccinia virus or an insect virus such as baculovirus can be used. In addition, many heterologous protein expression systems using yeast, insect cells, and mammalian cells as hosts have been constructed, and have been already commercially available. These expression systems may be used for preparation of the reverse transcriptase mutant of the present invention.

A promoter to be incorporated into the expression vector of the present invention can be selected depending on a host. Examples of the promoter when the host is *E. coli* include, but not limited to, promoters from *E. coli* or phage such as a trp promoter, a lac promoter, a PL promoter and a PR promoter, and promoters altered from the above-mentioned promoters. Furthermore, an expression system comprising a phage-derived promoter and an RNA polymerase gene in combination (for example, a pET expression system etc.) may be used.

In order to facilitate purification of an expressed polypeptide, the expression vector of the present invention may further comprise a nucleic acid encoding an affinity tag. The nucleic acid encoding an affinity tag is inserted into the vector so as to allow expression of a fusion protein of the reverse transcriptase mutant of the present invention and the affinity tag. Examples of the affinity tag include, but not limited to, nucleic acids encoding a histidine (His) tag, a glutathione S-transferase (GST) tag, a maltose binding protein (MBP) tag, a Strep (II) tag consisting of 8 amino acid residues (Trp-Ser-His-Pro-Gln-Phe-Glu-Lys), and the like. The tag may be added to the 5' end and/or the 3' end of the nucleic acid encoding the MMLV reverse transcriptase (MMLV RTase) mutant of the present invention, and may be appropriately added to such a position that the expression and the tag function are not impaired. The tag is preferably a tag that can be cleaved in a purification step of an expressed polypeptide. Examples of such a cleavable tag include, but not limited to, tags comprising nucleic acids encoding recognition sequences of fusion polypeptidecleaving proteases such as Facror Xa, PreScission Protease, Thrombin, enterokinase, and TEV protease (Tobacco etch virus protease).

The expression vector of the present invention may further contain one or more expression regulatory sequences. Examples of the expression regulatory sequence include, not limited to, a promoter and a gene involved in the control of a promoter, a ribosome binding sequence, a polyadenylation signal, a transcription termination sequence (transcription terminator), and an enhancer. Further examples of the expression regulatory sequence include a replication origin (origin), a gene encoding a marker used for selection of transformants (drug resistance gene, a fluorescent marker, a luminescent marker), and a base sequence for enhancing translation efficiency.

4. Cell transformed with Expression vector of the Present Invention

A Cell (host) to be transformed with the vector for expressing the reverse transcriptase mutant of the present invention may be any host commonly used in the art, and it is not particularly limited. For example, bacteria (*E. coli, Bacillus subtilis*, etc.), yeast, filamentous fungi, insect cells, eukaryotic cells, and animal cells (mammalian cells including human cells, etc.) can be used.

When a prokaryotic cell is used as the host cell, for example, a bacterium belonging to genus *Escherichia* such as *Escherichia coli* (*E. coli*), genus *Bacillus* such as *Bacillus subtilis*, genus *Pseudomonas* such as *Pseudomonas putida*, or genus *Rhizobium* such as *Rhizobium meliloti* can be used as the host cell. *E. coli* that can be used for production of heterologous proteins is well known to a person skilled in the art, and many strains thereof are commercially available (for example, *Escherichia coli* BL21T1R, *Escherichia coli* BL21, *E. coli* XL1-Blue, *E. coli* XL2-Blue, *E. coli* DHl, *E. coli* JM109, *E. coli* HB101, etc.). In addition, *Bacillus subtilis* MI114, *B. subtilis* 207-21 and the like belonging to genus *Bacillus*, and *Brevibacillus choshinensis* and the like belonging to genus *Brevibacillus* are known as hosts for production of heterologous proteins. A combination of the host cell and an expression vector suitable for the host can be used in production of a fusion polypeptide of the present invention. Preferably, but not limited to, *E. coli* BL21T1R or BL21DE3 which is an *E. coli* BL2 strain can be used.

A method for introducing the expression vector into the host is not particularly limited as long as it can introduce a nucleic acid into the host, and examples thereof include a method comprising use of a calcium ion, an electroporation method, a spheroplast method, and a lithium acetate method. A method for introducing a recombinant vector into an insect cell is not particularly limited as long as it can introduce a DNA into an insect cell, and examples thereof include a calcium phosphate method, a lipofection method, and an electroporation method. In the case where a phage vector or a viral vector is used, a host cell may be infected with the vector by a method suitable for the vector used to obtain a transformant expressing the fusion polypeptide of the present invention.

After the transformant is cultured, the reverse transcriptase mutant of the present invention can be obtained from the culture. The culture conditions are not particularly limited as long as they are suitable for the expression vector used, the host used and the like. For example, in the case where *E. coli* is transformed with a pET vector, a transformant is inoculated into an LB medium and cultured at 37° C. with shaking. When the culture reaches to an OD of 0.2 to 0.8, IPTG is added to the medium, and the shaking culture is continued, for example, at 15 to 30° C. for 2 to 5 hours, preferably at 25° C. for 4 to 5 hours in order to induce the expression of a protein of interest. Thereafter, a culture solution is centrifuged, and the obtained cells are washed, and then sonicated or lysed with lysozyme to obtain a disrupted product containing the mutant of the present invention. Since the disrupted product contains many contaminants, it is preferable that the mutant of the present invention is purified by appropriately using purification methods used in the art such as ammonium sulfate precipitation, anion exchange column chromatography, cation exchange column chromatography, gel filtration, affinity column chromatography, dialysis, etc. in combination. The mutant to which the affinity tag is added can be conveniently purified using an affinity carrier selected depending on the property of the affinity tag. In addition to IPTG, other necessary inducers such as L-arabinose may be added at appropriate timing depending on the type of host or expression vector used.

5. Method of Producing Nucleic Acid Encoding Heat-Resistant Reverse Transcriptase Mutant of the Present Invention A method for producing the nucleic acid of the present invention comprises, for example, a step of replacing a codon encoding threonine at a position corresponding to position 55 of the amino acid sequence of a wild-type MMLV reverse transcriptase in a nucleic acid encoding a MMLV reverse transcriptase, with a codon encoding an amino acid to stabilize a steric structure, such as an amino acid selected from the group consisting of amino acids having non-polar aliphatic side chains, amino acids having polar acidic functional group side chains, amino acids having polar basic functional group side chains, and amino acids having polar hydroxy aliphatic side chains. The amino acid to stabilize a steric structure is as explained in above section 1. The codon encoding threonine is, but not limited to, preferably replaced with a codon encoding an amino acid selected from the group consisting of amino acids having nonpolar aliphatic side chains and amino acids having polar acidic functional group side chains, and more preferably replaced with a code encoding glycine or aspartic acid.

As explained in above section 1, the reverse transcriptase mutant of the present invention is characterized by, for example, comprising a mutation that is a replacement of threonine at a position corresponding to position 55 of the amino acid sequence of a wild-type MMLV reverse transcriptase, with an amino acid to stabilize a steric structure, such as an amino acid selected from the group consisting of amino acids having non-polar aliphatic side chains, amino acids having polar acidic functional group side chains, amino acids having polar basic functional group side chains, and amino acids having polar hydroxy aliphatic side chains. In the present invention, a reverse transcriptase amino acid sequence into which the amino acid replacement at position 55 will be introduced may be a wild-type amino acid sequence, or a mutant amino acid sequence, such as an amino acid sequence of a heat-resistant mutant. Therefore, in the method for producing the nucleic acid of the present invention, the nucleic acid encoding a MMLV reverse transcriptase into which the above-described codon replacement will be introduced may be a nucleic acid encoding a wild-type MMLV reverse transcriptase, or a nucleic acid encoding a MMLV reverse transcriptase mutant.

For example, in the case where the amino acid replacement at position 55 is introduced into a MMLV heat-resistant reverse transcriptase mutant, a codon encoding threonine at a position corresponding to position 55 of the amino acid sequence of the wild-type MMLV reverse transcriptase in a nucleic acid encoding the MMLV heat-resistant reverse transcriptase mutant is replaced with a codon encoding an amino acid selected from the group consisting of amino acids having non-polar aliphatic side chains, amino acids having polar acidic functional group side chains, amino acids having polar basic functional group side chains, and amino acids having polar hydroxy aliphatic side chains, and thereby, a nucleic acid encoding a reverse transcriptase mutant having increased heat-resistance as compared with the heat-resistance of the reverse transcriptase mutant before the codon replacement can be produced.

For example, the nucleic acid encoding the MMLV heat-resistant reverse transcriptase mutant into which the above-described codon replacement will be introduced may be a nucleic acid encoding a reverse transcriptase mutant comprising one or more amino acid replacements selected from the group consisting of the following (1) to (8):
(1) A54P,
(2) T287K,
(3) Q291K,
(4) T306K,
(5) D524A,
(6) D524N,
(7) H204R, M289L, T306K and F309N, and
(8) D209P and I212A.

The above-described codon replacement may be performed by a known method. For example, the codon replacement can be performed by mutagenesis using a known method, such as site-directed mutagenesis using primers for mutagenesis, or artificial synthesis of a nucleic acid having a mutated sequence (or a part of the sequence). In addition, codon optimization may be performed in order to allow the expression in a host used or increase the expression level. The codon optimization can be performed by a method commonly used in the art.

Furthermore, in the nucleic acid production method of the present invention, one or more other codon replacements as well as the codon replacement to introduce the amino acid replacement at position 55 may be performed in the nucleic acid encoding a MMLV reverse transcriptase. Examples of the other codon replacements include a codon replacement to introduce a mutation for imparting heat resistance, a codon replacement to introduce an amino acid replacement for increasing heat resistance, a codon replacement to introduce a mutation for improving the properties of reverse transcriptase, and a codon replacement to introduce an RNase H activity deletion mutation. Examples of the codon replacement to introduce an amino acid replacement for imparting or increasing heat resistance include, but not limited to, codon replacements to introduce the above-mentioned amino acid replacements (1) to (8). Further, codon replacements to stabilize or increase protein production in a host may be performed in combination with the above-mentioned codon replacement.

The nucleic acid production method of the present invention is applicable to production of the nucleic acid as explained in above section 2.

6. Method for Producing Reverse Transcriptase Mutant of the Present Invention and Method for Improving Heat Resistance of Reverse Transcriptase of the Present Invention The method for producing a reverse transcriptase mutant of the present invention is characterized by replacing threonine at a position corresponding to position 55 of the amino acid sequence of a wild-type MMLV reverse transcriptase, with an amino acid to stabilize a steric structure, such as a different amino acid selected from the group consisting of amino acids having non-polar aliphatic side chains, amino acids having polar acidic functional group side chains, amino acids having polar basic functional group side chains, and amino acids having polar hydroxy aliphatic side chains. The method for improving the heat-resistance of a reverse transcriptase of the present invention is characterized by replacing threonine at a position corresponding to position 55 of the amino acid sequence of a wild-type MMLV reverse transcriptase, with an amino acid to stabilize a steric structure, such as a different amino acid selected from the group consisting of amino acids having non-polar aliphatic side chains, amino acids having polar acidic functional group side chains, amino acids having polar basic functional group side chains, and amino acids having polar hydroxy aliphatic side chains. The amino acid to stabilize a steric structure is as explained in above section 1. The amino acid replacement at position 55 is preferably a replacement with an amino acid selected from the group consisting of amino acids having nonpolar aliphatic side chains and amino acids having polar acidic functional group side chains, more preferably a replacement with glycine or aspartic acid.

The method for producing a reverse transcriptase mutant of the present invention and the method for improving the heat resistance of a reverse transcriptase of the present invention comprise introducing the amino acid replacement at position 55 into an amino acid sequence of a MMLV reverse transcriptase. The amino acid sequence of a MMLV reverse transcriptase may be a wild-type amino acid sequence or a mutant sequence. In the case where an amino acid sequence of a MMLV heat-resistant reverse transcriptase mutant is used as the mutant sequence, a reverse transcriptase mutant having increased heat-resistance as compared with the heat-resistance of the reverse transcriptase mutant before introduction of the amino acid replacement at position 55 can be produced by introducing the amino acid replacement at position 55 according to the present invention.

Therefore, according to the method for improving the heat-resistance of a reverse transcriptase of the present invention, the heat-resistance of a MMLV heat-resistant reverse transcriptase mutant can be increased as compared with the heat-resistance of the reverse transcriptase mutant before introduction of the amino acid replacement at position 55 by introducing the amino acid replacement at position 55 into the amino acid sequence of the MMLV heat-resistant reverse transcriptase mutant. According to this technique, the heat-resistance of an existing heat-resistant reverse transcriptase can be further increased. The said technique is useful as a method for producing a reverse transcriptase mutant having increased heat-resistance.

Examples of the MMLV heat-resistant reverse transcriptase mutant into which the amino acid replacement at position 55 will be introduced include, but not limited to, reverse transcriptase mutants comprising one or more amino acid replacements selected from the group consisting of the following (1) to (8):
(1) A54P,
(2) T287K,
(3) Q291K,
(4) T306K,
(5) D524A,
(6) D524N,
(7) H204R, M289L, T306K and F309N, and
(8) D209P and I212A.

Furthermore, in the method for producing a reverse transcriptase mutant of the present invention and the method for improving the heat resistance of a reverse transcriptase of the present invention, a mutation(s) at one or more other amino acid positions as well as the amino acid replacement at position 55 may be introduced in the amino acid sequence of a MMLV reverse transcriptase. Examples of the mutation(s) at one or more other amino acid positions include a mutation for imparting heat resistance, a mutation for increasing heat resistance, a mutation for improving the properties of reverse transcriptase, and an RNase H activity deletion mutation. Examples of the mutation for imparting or increasing heat resistance include, but not limited to, the above-mentioned amino acid replacements (1) to (8).

Introduction of the above-mentioned amino acid replacements and other mutations may be carried out by a known method, for example, a method of introducing a mutation into a corresponding nucleotide sequence by using PCR, or a method of artificially synthesizing an entire nucleic acid of a gene. For example, a nucleic acid encoding the reverse transcriptase mutant of the present invention may be prepared as described in above section 5, the reverse transcriptase mutant may be expressed in a host cell using a suitable expression vector, and the reverse transcriptase mutant may be obtained from the cell culture.

According to the method for producing a reverse transcriptase mutant of the present invention and the method for improving the heat resistance of a reverse transcriptase of the present invention, for example, a reverse transcriptase that can be used even under temperature conditions of 40° C. or more, 45° C. or more, 50° C. or more, 55° C. or more, or 60° C. or more is obtained. The method for producing a reverse transcriptase mutant of the present invention and the method for improving the heat resistance of a reverse transcriptase of the present invention can increase the heat-resistance without affecting the properties of reverse transcriptase, such as RNA binding activity, cDNA elongation activity, and cDNA elongation rate.

7. Method for Synthesizing cDNA Using Reverse Transcriptase Mutant of the Present Invention The reverse transcriptase mutant of the present invention can be used in a cDNA synthesis method comprising a step of synthesizing a DNA complementary to an RNA. Since the reverse transcriptase mutant of the present invention is heat-resistant, use of the reverse transcriptase mutant of the present invention enables reverse transcription reaction at a higher temperature than the wild-type MMLV reverse transcriptase. Furthermore, since the reverse transcriptase mutant of the present invention has increased heat-resistance as compared with conventional heat-resistant reverse transcriptases, use of the reverse transcriptase mutant of the present invention enables reverse transcription reaction under higher temperature conditions as compared with the conventional heat-resistant reverse transcriptases. Although synthesis of cDNA has been performed at 40° C., 45° C., 50° C. or 55° C. using known heat-resistant reverse transcriptases, use of the reverse transcriptase mutant of the present invention enables reverse transcription reaction under high temperature conditions that have never been expected, such as 40° C. or more, 45° C. or more, 50° C. or more, 55° C. or more, 60° C. or more, or 70° C. or more. Thus, destruction of the higher-order structure of mRNA which cannot be achieved under the conventional temperature conditions can be achieved by using the reverse transcriptase mutant of the present invention. As a result, cDNA is easily synthesized from a full-length mRNA.

For performing the cDNA synthesis method as described above, a reaction solution containing a divalent metal salt, dNTPs, a buffer component (buffer solution) for maintaining pH, a reducing agent and the like is usually prepared. Examples of a bivalent metal ion which constitutes the bivalent metal salt include, but not limited to, a manganese ion, a magnesium ion, and a cobalt ion. Suitable divalent metal ions for reverse transcriptase and their concentration are known in the art. The divalent metal ion may be supplied in the form of a salt such as chloride, sulfate or acetate. Examples of the concentration of the divalent metal ion in the composition of the present invention include, but not limited to, preferably 0.5 to 20 mM. As the dNTPs, at least one selected from the group consisting of dATP, dCTP, dGTP and dTTP, and their derivatives is used. Preferably, a mixture of dATP, dCTP, dGTP and dTTP is used.

As the buffer component for maintaining pH, a mixture of a weak acid and its conjugated base or a mixture of a weak base and its conjugated acid which are known in the art can be used. Examples of the buffer component for maintaining pH include, but not limited to, a Tris buffer, a HEPES buffer, an acetate buffer, and a phosphate buffer. For example, buffer components suitable for reverse transcriptase and their concentration are known in the art. Examples of the reducing agent include, but not limited to, DTT (dithiothreitol) and 2-mercaptoethanol. Suitable reducing agents for reverse transcriptase and their concentration are known in the art.

For cDNA synthesis using primers, for example, random 6-mers, Oligo dT primer, and gene specific primers can be used as the primers. The length of the primer is preferably 6 nucleotides or more, more preferably 10 nucleotides or more from the viewpoint of hybridization specificity, and preferably 100 nucleotides or less, more preferably 30 nucleotides or less from the viewpoint of oligonucleotide synthesis. As a random primer for non-specific cDNA synthesis, a mixture of oligonucleotides having a length of 6 to 8 nucleotides may be used. The oligonucleotides may be chemically synthesized, for example, by a known method, or may be derived from a biological sample. For example, the oligonucleotides may be prepared by preparing a DNA from a natural sample, digesting the DNA with restriction endonucleases and isolating the oligonucleotides from the digested products.

The cDNA obtained by the above-described method may be used as a template to further amplify the cDNA. Examples of DNA amplification reaction include a PCR method and various isothermal amplification methods. Since nucleic acid amplification is performed by a complementary strand synthesis reaction using the cDNA obtained by the above-described cDNA synthesis method as a template, a DNA polymerase may be further added to the reaction solution. A preferable example of the DNA polymerase is a heat-resistant DNA polymerase.

Since the reverse transcriptase mutant of the present invention has excellent heat resistance as described above, it is useful for cDNA synthesis or RT-PCR utilizing reverse transcription reaction wherein an RNA which forms a complicated secondary structure is used as a template.

8. Composition or Kit of the Present Invention

The composition of the present invention is a composition for reverse transcription reaction. The composition of the present invention contains, in addition to the reverse transcriptase mutant of the present invention, components necessary for reverse transcription, such as a divalent metal salt, dNTPs, a buffer component, a reducing agent, sterile water and the like. The composition of the present invention may further contain primers. The kit of the present invention is a kit for reverse transcription reaction. Examples of the kit of the present invention include a kit containing the reverse transcriptase mutant of the present invention, a divalent metal salt, dNTP, a buffer component, a reducing agent and the like, and for preparing a reverse transcription reaction solution by mixing the contents when using the kit; a kit containing the composition of the present invention, which necessitates only addition of a template DNA and water (such as sterile water) when using the kit; and a kit containing the composition of the present invention in a dry state. Also included in the present invention is a kit for the purpose of detecting a specific RNA, which contains primers specific for the target RNA and an RNA for a positive control. The bivalent metal salt, dNTPs, buffer component, and reducing agent are as explained in above section 7.

Furthermore, the kit of the present invention may contain components necessary for double-stranded nucleic acid synthesis, such as a heat-resistant DNA polymerase, and components necessary for detection of an amplified double-stranded nucleic acid, such as intercalators and fluorescently labeled probes. Examples of the intercalator include SYBR (registered trademark) Green I and other nucleic acid binding dyes. Examples of the fluorescently labeled probe include TaqMan (registered trademark) probes, Cycleave (registered trademark) probes, and molecular beacon probes. The kit may further contain a primer set for double stranded nucleic acid synthesis.

EXAMPLES

Hereinafter, the present invention will be more specifically explained by way of Examples, which the present invention is not limited to.

Experimental Method 1

(1) Preparation-A of Reverse Transcriptase Mutant

A nucleotide sequence of a gene encoding a wild-type reverse transcriptase from Moloney murine leukemia virus is disclosed in Genbank Acc. No. AF033811.1. Based on the nucleotide sequence, a mutation was introduced at a specific site by a conventional method to prepare an artificial gene. The artificial gene thus obtained was introduced into plasmid pET6×HN-C (manufactured by Takara Bio USA) using In-Fusion (registered trademark) HD Cloning Kit (manufactured by Takara Bio USA). The plasmid thus obtained had a nucleotide sequence encoding a reverse transcriptase mutant having a histidine tag attached to its C-terminal side.

Next, *E. coli* BL21 (DE3) strain (manufactured by Takara Bio Inc.) was transformed with the plasmid, and cultured overnight at 37° C. on a 1.5% agarose LB plate containing 100 µg/ml of ampicillin. Three single colonies were selected from this plate, inoculated into an LB medium containing 100 µg/ml of ampicillin (hereinafter referred to as an "LB-AP medium"), and cultured with shaking at 37° C. overnight. Then, 300 µl of a culture solution was inoculated into 6 ml of an LB-AP medium, and cultured with shaking at 37° C. overnight. When an OD600 value of 0.6 was reached, IPTG was added at a final concentration of 1 mM to the culture solution and further cultured at 25° C. for 4 hours for induction. When an OD600 value of 4 was reached, bacterial cells were harvested.

The cells as obtained above were suspended in a solution containing 400 µl of 50 mM Tris-HCl pH 7.5, 300 mM NaCl, 5% glycerol and 0.15% Triton X-100 (hereinafter referred to as "Buffer S"), and sonicated three times at 4° C. for 30 seconds using a sonicator (manufactured by Sonic & Materials, Inc.). Thus the suspension became clear. The suspension after sonication was centrifuged at 4° C. at 11000×g for 10 minutes, and a supernatant was collected. A crude extract thus obtained was subjected to Ni resin purification.

The Ni resin purification was performed as follows. Fifty microliters of Ni-NTA Agarose (manufactured by Qiagen) in a 1.5 ml tube was washed twice with 250 µl of sterile distilled water, and then equilibrated twice with 250 µl of Buffer A (50 mM Tris-HCl pH 7.5, 300 mM NaCl, 5% glycerol, and 5 mM imidazole). The equilibrated Ni-NTA Agarose was suspended in 400 µl of the crude extract, left to stand for 30 minutes, and then centrifuged at 4° C., at 12000×g for 10 minutes. After a supernatant was removed, the precipitated Ni-NTA Agarose was washed three times with 100 µl of Buffer A. Then, 100 µl of Buffer B (50 mM Tris-HCl pH 7.5, 300 mM NaCl, 5% glycerol and 300 mM imidazole) was used to elute adsorbed substances from the Ni-NTA Agarose. The eluate thus obtained was used as a reverse transcriptase mutant solution in the next test.

(2) Heat-Resistance Evaluation Test-A of Reverse Transcriptase Mutant

The reverse transcriptase mutant solution obtained in above (1) was tested for heat resistance by the following method. The reverse transcriptase mutant solution was diluted 2-fold with a dilution buffer (50 mM Tris-HCl pH 8.3, 2 mM DTT, 0.1% NP-40 and 10% glycerol) containing bovine serum albumin (manufactured by Takara Biotechnology (Dalian) Co., Ltd.) at a final concentration of 0.25%. The diluted solution was not heated, or was heated at 44° C. or 50° C. for 15 minutes. The unheated diluted solution and the heated diluted solutions were diluted 5-fold with the dilution buffer, and then subjected to measurement of reverse transcriptase activity.

The measurement was performed as follows. To 35 µl of a reaction solution containing 0.01 µg/µl of poly(riboadenine nucleotide), 0.1 ng/µl of oligo(dT)$_{12-18}$, 85 mM potassium chloride, 8 mM magnesium chloride, 50 mM Tris-HCl pH 8.3, 10 mM DTT and 0.1% NP-40, 5 µl of the unheated or heated diluted solution was added and heated at 37° C. for 5 minutes. Next, 10 µl of 2.5 mM dTTP was added to the reaction solution, and reacted at 37° C. for 10 minutes. The reaction was stopped by adding 5 µl of a 100 mM EDTA solution. After the reaction was stopped, 5 µl of the reaction solution was put into a 96-well plate. In each well of this plate, 150 µl of 1×SYBR Green I (manufactured by Thermo Scientific Inc.) was put and mixed using a plate mixer (manufactured by Taitec Corporation). Then, the plate was centrifuged at 1000 rpm for 1 minute using a plate centrifuge (manufactured by Allegra). After centrifugation, the plate was set in TECAN infinite 200 pro (manufactured by Tecan), and reverse transcriptase activity was measured by determining the amount of fluorescence in each well at an excitation wavelength of 485 nm and a detection wavelength of 520 nm.

Experimental Method 2

(1) Preparation-B of Reverse Transcriptase Mutant

A Reverse transcriptase mutant was prepared by the same method as described in Experimental method 1-(1) except that the cell treatment method was changed from sonication to lysis with lysozyme.

(2) Heat-Resistance Evaluation Test-B of Reverse Transcriptase Mutant

The reverse transcriptase mutant obtained in above (1) was tested for heat resistance by the same method as described in Experimental method 1-(2) except that the heating temperature was changed to 55° C., 60° C., 65° C. or 70° C.

Example 1: Preparation-1 of Reverse Transcriptase Mutant (1) Preparation of MMLV reverse transcriptase mutants O1 To O3 and P12, P13 (T55G, T55A, T55S, T55D, T55K)

According to Experimental method 1-(1), an artificial gene encoding a mutant protein in which threonine at position 55 was replaced with glycine in the wild-type amino acid sequence of MMLV reverse transcriptase was prepared. Using the artificial gene thus obtained, protein expression and purification were performed according to Experimental method 1-(1). As used herein, a reverse transcriptase mutant having a replacement mutation from threonine to glycine at position 55 was named "O1". A reverse transcriptase mutant in which threonine at position 55 was replaced with alanine and a reverse transcriptase mutant in which threonine at position was replaced with serine were named "O2" and "O3", respectively. A reverse transcriptase mutant in which threonine at position 55 was replaced with aspartic acid and a reverse transcriptase mutant in which threonine at position 55 was replaced with lysine were named "P12" and "P13", respectively. The amino acid sequences and nucleotide sequences of these proteins are shown in SEQ ID NOs: 21-26.

(2) Preparation of MMLV Reverse Transcriptase Mutant C3 (T55G+A54P)

According to Experimental method 1-(1), an artificial gene encoding a mutant protein in which threonine at position 55 was replaced with glycine and alanine at position 54 was replaced with proline in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 54 and 55 was named "C3". The amino acid sequence and nucleotide sequence of the protein are shown in SEQ ID NOS: 4 and 14.

(3) Preparation of MMLV Reverse Transcriptase Mutant D1 (T287K)

According to Experimental method 1-(1), an artificial gene encoding a mutant protein in which threonine at position 287 was replaced with lysine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutation at position 287 was named "D1". The amino acid sequence and nucleotide sequences of the protein are shown in SEQ ID NOs: 27 and 33.

(4) Preparation of MMLV Reverse Transcriptase Mutant O1+D1 (T55G+T287K)

According to Experimental method 1-(1), an artificial gene encoding a mutant protein in which threonine at position 55 was replaced with glycine and threonine at position 287 was replaced with lysine in the wild-type amino acid sequence of MMLV reverse transcriptase was prepared. Using the artificial gene thus obtained, protein expression and purification were performed according to Experimental method 1-(1). As used herein, the reverse transcriptase mutant having the replacement mutations at positions 55 and 287 was named "O1+D1". The amino acid sequence and nucleotide sequences of the protein are shown in SEQ ID NOs: 5 and 15.

(5) Preparation of MMLV reverse transcriptase mutant C3+D1 (T55G+A54P+T287K)

According to Experimental method 1-(1), an artificial gene encoding a mutant protein in which threonine at position 55 was replaced with glycine, alanine at position 54 was replaced with proline and threonine at position 287 was replaced with lysine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 55, 54 and 287 was named "C3+D1". The amino acid sequence and nucleotide sequence of the protein are shown in SEQ ID NOs: 39 and 45.

(6) Preparation of MMLV reverse transcriptase mutant LT (H204R+M289L+T306K+F309N)

According to Experimental method 1-(1), an artificial gene encoding a mutant protein in which histidine at position 204 was replaced with arginine, methionine at position 289 was replaced with leucine, threonine at position 306 was replaced with lysine, and phenylalanine at position 309 was replaced with asparagine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 204, 289, 306 and 309 was named "LT". The amino acid sequence and nucleotide sequence of the protein are shown in SEQ ID NOs: 32 and 38.

(7) Preparation of MMLV reverse transcriptase mutant O1+LT (T55G+H204R+M289L+T306K+F309N)

According to Experimental method 1-(1), an artificial gene encoding a mutant protein in which threonine at position 55 was replaced with glycine, histidine at position 204 was replaced with arginine, methionine at position 289 was replaced with leucine, threonine at position 306 was replaced with lysine, and phenylalanine at position 309 was replaced with asparagine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 55, 204, 289, 306 and 309 was named "O1+LT". The amino acid sequence and nucleotide sequence of the protein are shown in SEQ ID NOs: 10 and 20.

(8) Preparation of MMLV reverse transcriptase mutant C3+LT (T55G+A54P+H204R+M289L+T306K+F309N)

According to Experimental method 1-(1), an artificial gene encoding a mutant protein in which alanine at position 54 was replaced with proline, threonine at position 55 was replaced with glycine, histidine at position 204 was replaced with arginine, methionine at position 289 was replaced with leucine, threonine at position 306 was replaced with lysine, and phenylalanine at position 309 was replaced with asparagine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 54, 55, 204, 289, 306 and 309 was named "C3+LT". The amino acid sequence and nucleotide sequence of the protein are shown in SEQ ID NOs: 44 and 50.

(9) Preparation of MMLV Reverse Transcriptase Mutant K1 (Q291K)

An artificial gene encoding a mutant protein in which glutamine at position 291 was replaced with lysine in the wild-type amino acid sequence of MMLV reverse transcriptase was prepared. Using the artificial gene thus obtained, protein expression and purification were performed according to Experimental method 1-(1). As used herein, a reverse transcriptase mutant having the mutation at position 291 was named as "K1". The amino acid sequence and nucleotide sequence of the protein are shown in SEQ ID NOS: 28 and 34 in the Sequence Listing.

(10) Preparation of MMLV Reverse Transcriptase Mutant O1+K1 (T55G+Q291K)

According to Experimental method 1-(1), an artificial gene encoding a mutant protein in which threonine at position 55 was replaced with glycine and glutamine at position 291 was replaced with lysine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 55 and 291 was named "O1+K1". The amino acid sequence and nucleotide sequence of the protein are shown in SEQ ID NOs: 6 and 16.

(11) Preparation of MMLV reverse transcriptase mutant C3+K1 (T55G+A54P+Q291K)

According to Experimental method 1-(1), an artificial gene encoding a mutant protein in which alanine at position 54 was replaced with proline, threonine at position 55 was replaced with glycine and glutamine at position 291 was replaced with lysine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 54, 55 and 291 was named "C3+K1". The amino acid sequence and nucleotide sequence of the protein are shown in SEQ ID NOs: 40 and 46.

(12) Preparation of MMLV Reverse Transcriptase Mutant K2 (D524N)

According to Experimental method 1-(1), an artificial gene encoding a mutant protein in which aspartic acid at position 524 was replaced with asparagine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutation at position 524 was named "K2". The amino acid sequence and nucleotide sequence of the protein are shown in SEQ ID NOs: 31 and 37.

(13) Preparation of MMLV Reverse Transcriptase Mutant O1+K2 (T55G+D524N)

According to Experimental method 1-(1), an artificial gene encoding a mutant protein in which threonine at position 55 was replaced with glycine and aspartic acid at position 524 was replaced with asparagine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 55 and 524 was named "O1+K2". The amino acid sequence and nucleotide sequence of the protein are shown in SEQ ID NOs: 9 and 19.

(14) Preparation of MMLV Reverse Transcriptase Mutant C3+K2 (T55G+A54P+D524N)

According to Experimental method 1-(1), an artificial gene encoding a mutant protein in which alanine at position 54 was replaced with proline, threonine at position 55 was replaced with glycine, and aspartic acid at position 524 was replaced with asparagine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 54, 55 and 524 was named "C3+K2". The amino acid sequence and nucleotide sequence of the protein are shown in SEQ ID NOs: 43 and 49.

(15) Preparation of MMLV Reverse Transcriptase Mutant K3 (D524A)

According to Experimental method 1-(1), an artificial gene encoding a mutant protein in which aspartic acid at position 524 was replaced with alanine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutation at position 524 was named "K3". The amino acid sequence and nucleotide sequence of the protein are shown in SEQ ID NOs: 30 and 36.

(16) Preparation of MMLV reverse transcriptase mutant O1+K3 (T55G+D524A)

According to Experimental method 1-(1), an artificial gene encoding a mutant protein in which threonine at position 55 was replaced with glycine and aspartic acid at position 524 was replaced with alanine in the wild-type amino acid sequence of MMLV reverse transcriptase was prepared. Using the artificial gene thus obtained, protein expression and purification were performed according to Experimental method 1-(1). As used herein, a reverse transcriptase variant having the replacement mutations at positions 55 and 524 was named "O1+K3". The amino acid sequence and nucleotide sequence of the protein are shown in SEQ ID NOs: 8 and 18.

(17) Preparation of MMLV Reverse Transcriptase Mutant C3+K3 (T55G+A54P+D524A)

According to Experimental method 1-(1), an artificial gene encoding a mutant protein in which alanine at position 54 was replaced with proline, threonine at position 55 was replaced with glycine and aspartic acid at position 524 was replaced with alanine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 54, 55 and 524 was named "C3+K3". The amino acid sequence and nucleotide sequence of the protein are shown in SEQ ID NOs: 42 and 48.

(18) Preparation of MMLV Reverse Transcriptase Mutant K4 (T306K)

According to Experimental method 1-(1), an artificial gene encoding a mutant protein in which threonine at position 306 was replaced with lysine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutation at position 306 was named "K4". The amino acid sequence and nucleotide sequence of the protein are shown in SEQ ID NOs: 2.9 and 35.

(19) Preparation of MMLV Reverse Transcriptase Mutant O1+K4 (T55G+T306K)

According to Experimental method 1-(1), an artificial gene encoding a mutant protein in which threonine at position 55 was replaced with glycine and threonine at position 306 was replaced with lysine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 55 and 306 was named "O1+K4". The amino acid sequence and nucleotide sequence of the protein are shown in SEQ ID NOs: 7 and 17.

(20) Preparation of MMLV Reverse Transcriptase Mutant C3+K4 (T55G+A54P+T306K)

According to Experimental method 1-(1), an artificial gene encoding a mutant protein in which alanine at position 54 was replaced with proline, threonine at position 55 was replaced with glycine and threonine in position 306 was replaced with lysine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 54, 55 and 306 was named "C3+K4". The amino acid sequence and nucleotide sequence of the protein are shown in SEQ ID NOs: 41 and 47.

(21) Preparation of MMLV Reverse Transcriptase Mutant C5 (D209P+I212A)

According to Experimental method 1-(1), an artificial gene encoding a mutant protein in which aspartic acid at position 209 was replaced with proline and isoleucine at position 212 was replaced with alanine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 209 and 212 was named "C5". The amino acid sequence and nucleotide sequence of the protein are shown in SEQ ID NOs: 51 and 53.

(22) Preparation of MMLV Reverse Transcriptase Mutant C3+C5 (T55G+A54P+D209P+I212A)

According to Experimental method 1-(1), an artificial gene encoding a mutant protein in which alanine at position 54 was replaced with proline, threonine at position 55 was replaced with glycine, aspartic acid at position 209 was replaced with proline and isoleucine at position 212 was replaced with alanine in the wild-type amino acid sequence of MMLV reverse transcriptase was prepared. Using the artificial gene thus obtained, protein expression and purification were performed according to Experimental method 1-(1). As used herein, a reverse transcriptase mutant having the replacement mutations at positions 54, 55, 209 and 212 was named "C3+C5". The amino acid sequence and nucleotide sequence of the protein are shown in SEQ ID NOs: 52 and 54.

Example 2: Heat-Resistance Evaluation Test-1 of Reverse Transcriptase Mutant

The reverse transcriptase mutants prepared in Example 1-(1) and the wild-type reverse transcriptase were tested for heat resistance according to Experimental method 1-(2). Results are shown in Table 1.

TABLE 1

| Types of mutations | Residual activity (%) | | |
|---|---|---|---|
| | Unheated | Heated, 44° C., 15 min. | Heated, 50° C., 15 min. |
| No mutation, wild-type | 100 | 24.8 | 2.2 |
| O1 T55G | 100 | 43.7 | 9.5 |
| O3 T55S | 100 | 32.3 | 2.1 |
| P12 T55D | 100 | 32.7 | 9.1 |
| P13 T55K | 100 | 27.9 | 2.2 |
| C3 A54P + T55G | 100 | 38.9 | 10.4 |

As shown in Table 1, mutants 01, P12 and C3 particularly had 1.3 to 4.7 times higher residual activity than the reverse transcriptase having the wild-type amino acid sequence after heating treatment at 44° C. and 50° C. for 15 minutes. Mutants 03 and P13 had 1.1 to 1.3 times higher residual activity than the wild-type reverse transcriptase after heating treatment at 44° C. for 15 minutes.

Example 3: Heat-resistance Evaluation Test-2 of Reverse Transcriptase Mutant

Combination of the amino acid replacements of the present invention with known mutations that had been reported to be involved in heat resistance or novel mutations that was found to be involved in heat resistance for the first time in the present invention were examined. Specifically, the reverse transcriptase mutants prepared in Example 1-(3) and (5), Example 1-(6) and (8), Example 1-(9) and (11), Example 1-(12) and (14), Example 1-(15) and (17), Example 1-(18) and (20), and Example 1-(21) and (22) were tested for heat resistance according to Experimental method 1-(2). Results are shown in Table 2.

TABLE 2

| Types of mutations | Residual activity (%) | | |
|---|---|---|---|
| | Unheated | Heated, 44° C., 15 min. | Heated, 50° C., 15 min. |
| D1 | 100 | 100 | 11 |
| C3 + D1 | 100 | 101 | 72 |
| LT | 100 | 60 | 29 |
| C3 + LT | 100 | 98 | 54 |
| K1 | 100 | 74 | 5 |
| C3 + K1 | 100 | 102 | 64 |
| K2 | 100 | 61 | 3 |
| C3 + K2 | 100 | 77 | 35 |
| K3 | 100 | 71 | 7 |
| C3 + K3 | 100 | 98 | 57 |
| K4 | 100 | 69 | 10 |
| C3 + K4 | 100 | 115 | 68 |

As shown in Table 2, any combination of mutations D1, LT, K2, K3 and K4, which had been reported to be involved in heat resistance, with amino acid replacement C3 of the present invention increased the residual activity after heating treatment at 44° C. or 50° C. for 15 minutes by 1.3 to 11.7 times. The combination of mutation K1, which was found to be involved in heat resistance for the first time in the present invention, with amino acid replacement C3 of the present invention increased the residual activity after heating treatment at 44° C. or 50° C. for 15 minutes by 1.4 to 12.8 times. Furthermore, the combination of mutation C5 with amino acid replacement C3 showed the similar results. These results show that the present invention further increases the heat resistance of a reverse transcriptase mutant having increased heat resistance.

Example 4: Heat-Resistance Evaluation Test-3 of Reverse Transcriptase Mutant Combinations of the amino acid replacements of the present invention with known mutations that had been reported to be involved in heat resistance or novel mutations that was found to be involved in heat resistance for the first time in the present invention were examined. Specifically, the reverse transcriptase mutants prepared in Example 1-(9) and (10), Example 1-(15) and (16), and Example 1-(18) and (19) were tested for heat resistance according to Experimental method 1-(2).

As a result, it was found that any combination of mutations K3 and K4, which had been reported to be involved in heat resistance, with amino acid replacement O1 of the present invention had increased residual activity after heating treatment at 50° C. for 15 minutes. Specifically, the combination of O1+K3 had 4.2 times higher residual activity than K3 and the combination of O1+K4 had 4.8 times higher residual activity than K4. The combination of mutation K1, which was found to be involved in heat resistance for the first time in the present invention, with amino acid replacement O1 of the present invention increased the remaining activity after heating treatment at 50° C. for 15 minutes by 4 times when K1 and O1+K1 were compared. These results show that amino acid replacement O1 of the present invention further increases the heat resistance of a reverse transcriptase mutant having increased heat resistance, similarly to amino acid replacement C3 as shown in Example 3. In addition, amino acid replacement O1 of the present invention can further increase the heat resistance when combined with any of mutations D1, LT, K2 and C5.

Example 5: Preparation-2 of Reverse Transcriptase Mutant (1) Preparation of MMLV Reverse Transcriptase Mutant P12+D1 (T55D+T287K)

According to Experimental method 2-(1), an artificial gene encoding a mutant protein in which threonine at position 55 was replaced with aspartic acid threonine at position 287 was replaced with lysine in the wild-type amino acid sequence of MMLV reverse transcriptase was prepared. Using the artificial gene thus obtained, protein expression and purification were performed according to Experimental method 2-(1). As used herein, a reverse transcriptase mutant having the replacement mutations at positions 55 and 287 was named "P12+D1". The amino acid sequence and nucleotide sequence of the protein are shown in SEQ ID NOs: 55 and 63.

(2) Preparation of MMLV Reverse Transcriptase Mutant P12+LT (T55D+H204R+M289L+T306K+F309N)

According to Experimental method 2-(1), an artificial gene encoding a mutant protein in which threonine at position 55 was replaced with aspartic acid, histidine at position 204 was replaced with arginine, methionine at position 289 was replaced with leucine, threonine at position 306 was replaced with lysine, and phenylalanine at position 309 was replaced with asparagine in the wild-type amino acid sequence of MMLV reverse transcriptase was prepared. Using the artificial gene thus obtained, protein expression and purification were performed according to Experimental method 2-(1). As used herein, a reverse transcriptase mutant having the replacement mutations at positions 55, 204, 289, 306 and 309 was named "P12+LT". The amino acid sequence and nucleotide sequence of the protein are shown in SEQ ID NOs: 56 and 64.

(3) Preparation of MMLV Reverse Transcriptase Mutant P12+K1 (T55D+Q291K)

According to Experimental method 2-(1), an artificial gene encoding a mutant protein in which threonine at position 55 was replaced with aspartic acid and glutamine at position 291 was replaced with lysine in the wild-type amino acid sequence of MMLV reverse transcriptase was prepared. Using the artificial gene thus obtained, protein expression and purification were performed according to Experimental method 2-(1). As used herein, a reverse transcriptase mutant having the replacement mutations at positions 55 and 291 was named "P12+K1". The amino acid sequence and nucleotide sequence of the protein are shown in SEQ ID NOs: 57 and 65.

(4) Preparation of MMLV Reverse Transcriptase Mutant P12+K2 (T55D+D524N)

According to Experimental method 2-(1), an artificial gene encoding a mutant protein in which threonine at position 55 was replaced with aspartic acid and aspartic acid at position 524 was replaced with asparagine in the wild-type amino acid sequence of MMLV reverse transcriptase was prepared. Using the artificial gene thus obtained, protein expression and purification were performed according to Experimental method 2-(1). As used herein, a reverse transcriptase mutant having the replacement mutations at positions 55 and 524 was named "P12+K2". The amino acid sequence and nucleotide sequence of the protein are shown in SEQ ID NOs: 58 and 66.

(5) Preparation of MMLV Reverse Transcriptase Mutant P12+K3 (T55D+D524A)

According to Experimental method 2-(1), an artificial gene encoding a mutant protein in which threonine at position 55 was replaced with aspartic acid and aspartic acid at position 524 was replaced with alanine in the wild-type amino acid sequence of MMLV reverse transcriptase was prepared. Using the artificial gene thus obtained, protein expression and purification were performed according to Experimental method 2-(1). As used herein, a reverse transcriptase mutant having the replacement mutations at positions 55 and 524 was named "P12+K3". The amino acid sequence and nucleotide sequence of the protein are shown in SEQ ID NOs: 59 and 67.

(6) Preparation of MMLV Reverse Transcriptase Mutant P12+K4 (T55D+T306K)

According to Experimental method 2-(1), an artificial gene encoding a mutant protein in which threonine at position 55 was replaced with aspartic acid and threonine at position 306 was replaced with lysine in the wild-type amino acid sequence of MMLV reverse transcriptase was prepared. Using the artificial gene thus obtained, protein expression and purification were performed according to Experimental method 2-(1). As used herein, a reverse transcriptase mutant having the replacement mutations at positions 55 and 306 was named "P12+K4". The amino acid sequence and nucleotide sequence of the protein are shown in SEQ ID NOs: 60 and 68.

(7) Preparation of MMLV Reverse Transcriptase Mutant O1+C5 (T55G+D209P+I212A)

According to Experimental method 2-(1), an artificial gene encoding a mutant protein in which threonine at position 55 was replaced with glycine, aspartic acid at position 209 was replaced with proline, and isoleucine at position 212 was replaced with alanine in the wild-type amino acid sequence of MMLV reverse transcriptase was prepared. Using the artificial gene thus obtained, protein expression and purification were performed according to Experimental method 2-(1). As used herein, a reverse transcriptase mutant having the replacement mutations at positions 55, 209 and 212 was named "O1+C5". The amino acid sequence and nucleotide sequence of the protein are shown in SEQ ID NOs: 61 and 69.

(8) Preparation of MMLV Reverse Transcriptase Mutant P12+C5 (T55D+D209P+I212A)

According to Experimental method 2-(1), an artificial gene encoding a mutant protein in which threonine at position 55 was replaced with aspartic acid, aspartic acid at position 209 was replaced with proline, and isoleucine at position 212 was replaced with alanine in the wild-type amino acid sequence of MMLV reverse transcriptase was prepared. Using the artificial gene thus obtained, protein expression and purification were performed according to Experimental method 2-(1). As used herein, a reverse transcriptase mutant having the replacement mutations at positions 55, 209 and 212 was named "P12+C5". The amino acid sequence and nucleotide sequence of the protein are shown in SEQ ID NOs: 62 and 70.

Example 6: Heat-Resistance Evaluation Test-4 of Reverse Transcriptase Mutant

Combinations of the amino acid replacements of the present invention with known mutations that had been reported to be involved in heat resistance or novel mutations that was found to be involved in heat resistance for the first time in the present invention were examined. Specifically, the reverse transcriptase mutants prepared in Example 1-(3), Example 1-(4) and Example 5-(1); Example 1-(6), Example 1-(7) and Example 5-(2); Example 1-(9), Example 1-(10) and Example 5-(3); Example 1-(12), Example 1-(13) and Example 5-(4); Example 1-(15), Example 1-(16) and Example 5-(5); Example 1-(18), Example 1-(19) and Example 5-(6); Example 1-(21) and Example 5-(7); and Example 1-(22) and Example 5-(8) were tested for heat resistance according to Experimental method 2-(2). Results are shown in Tables 3 and 4.

TABLE 3

| Types of mutations | Residual activity (%) | |
|---|---|---|
|  | Unheated | Heated, 55° C., 15 min. |
| D1 | 100 | 9 |
| O1 + D1 | 100 | 58 |
| P12 + D1 | 100 | 33 |
| LT | 100 | 61 |
| O1 + LT | 100 | 76 |
| P12 + LT | 100 | 78 |
| K1 | 100 | 5 |
| O1 + K1 | 100 | 42 |
| P12 + K1 | 100 | 15 |
| K2 | 100 | 12 |
| O1 + K2 | 100 | 20 |
| P12 + K2 | 100 | 14 |
| K3 | 100 | 7 |
| O1 + K3 | 100 | 50 |
| P12 + K3 | 100 | 12 |
| K4 | 100 | 7 |
| O1 + K4 | 100 | 42 |
| P12 + K4 | 100 | 15 |

As shown in Table 3, any combination of mutations D1, LT, K2, K3 and K4, which had been reported to be involved in heat resistance, with amino acid replacements O1 and P12 of the present invention greatly increased the residual activity after heating treatment at 55° C. for 15 minutes by 1.3 to 7.1 times.

The combinations of mutation K1, which was found to be involved in heat resistance for the first time in the present invention, with amino acid replacements O1 and P12 of the present invention greatly increased the residual activity after heating treatment at 55° C. for 15 minutes by 3.0 to 8.4 times.

These results show that the present invention further increases the heat resistance of a reverse transcriptase mutant having increased heat resistance.

TABLE 4

| Types of mutations | Residual activity (%) | |
|---|---|---|
|  | Unheated | Heated, 55° C., 15 min. |
| C5 | 100 | 4 |
| O1 + C5 | 100 | 31 |
| P12 + C5 | 100 | 8 |
| C3 + C5 | 100 | 36 |

As shown in Table 4, any combination of mutation C5, which was found to be involved in heat resistance for the first time in the present invention, with amino acid replacements O1 and P12 of the present invention greatly increased the residual activity after heating treatment at 55° C. for 15 minutes by 2.0 to 9.0 times. The combination of amino acid replacements C5 and C3 also showed the similar result.

These results show that the present invention further increases the heat resistance of a reverse transcriptase mutant having increased heat resistance.

Example 7: Heat-Resistance Evaluation Test-5 of Reverse Transcriptase Mutant

Combinations of the amino acid replacements of the present invention with known mutations that had been reported to be involved in heat resistance or novel mutations that was found to be involved in heat resistance for the first time in the present invention were examined. Specifically, the reverse transcriptase mutants prepared in Example 1-(7) and Example 5-(2) were tested for heat resistance according to Experimental method 2-(2).

As a result, it was found that the combination of O1+LT, wherein mutation LT had been reported to be involved in heat resistance and O1 was the amino acid replacement of the present invention, had 6.7 times higher residual activity after heating treatment at 60° C. for 15 minutes, 1.9 times higher residual activity after heating treatment at 65° C. for 15 minutes, and 1.9 times higher residual activity after heating treatment at 70° C. for 15 minutes as compared with LT. In addition, it was found that the combination of P12+LT, wherein P12 was the amino acid replacement of the present invention, had 2.4 times higher residual activity after heating treatment at 60° C. for 15 minutes, 1.9 times higher residual activity after heating treatment at 65° C. for 15 minutes, and 1.9 times higher residual activity after heating treatment at 70° C. for 15 minutes as compared with LT.

These results show that the present invention further increases the heat resistance of a reverse transcriptase mutant having increased heat resistance.

INDUSTRIAL APPLICABILITY

According to the present invention, a heat-resistant reverse transcriptase mutant is provided. Use of the reverse transcriptase mutant enables cDNA synthesis from a template RNA having strong secondary structure, though reverse transcriptase reaction of such RNA was difficult hitherto. The heat-resistant reverse transcriptase mutant is useful in a wide range of fields such as genetic engineering, biology, medicine, agriculture and the like.

SEQUENCE LISTING FREE TEXT

SEQ ID NO: 1: Moloney Murine Leukemia Virus reverse transcriptase amino acid sequence
SEQ ID NO: 2: Reverse transcriptase mutant O1(T55G) amino acid sequence
SEQ ID NO: 3: Reverse transcriptase mutant P12(T55D) amino acid sequence
SEQ ID NO: 4: Reverse transcriptase mutant C3(T55G+A54P) amino acid sequence
SEQ ID NO: 5: Reverse transcriptase mutant O1+D1 (T55G+T287K) amino acid sequence
SEQ ID NO: 6: Reverse transcriptase mutant O1+K1 (T55G+Q291K) amino acid sequence
SEQ ID NO: 7: Reverse transcriptase mutant O1+K4 (T55G+T306K) amino acid sequence
SEQ ID NO: 8: Reverse transcriptase mutant O1+K3 (T55G+D524A) amino acid sequence
SEQ ID NO: 9: Reverse transcriptase mutant O1+K2 (T55G+D524N) amino acid sequence
SEQ ID NO: 10: Reverse transcriptase mutant O1+LT (T55G+H204R+M289L+T306K+F309N) amino acid sequence
SEQ ID NO: 11: Moloney Murine Leukemia Virus reverse transcriptase nucleic acid sequence
SEQ ID NO: 12: Reverse transcriptase mutant O1(T55G) nucleic acid sequence
SEQ ID NO: 13: Reverse transcriptase mutant P12(T55D) nucleic acid sequence
SEQ ID NO: 14: Reverse transcriptase mutant C3(T55G+A54P) nucleic acid sequence
SEQ ID NO: 15: Reverse transcriptase mutant O1+D1 (T55G+T287K) nucleic acid sequence
SEQ ID NO: 16: Reverse transcriptase mutant O1+K1 (T55G+Q291K) nucleic acid sequence
SEQ ID NO: 17: Reverse transcriptase mutant O1+K4 (T55G+T306K) nucleic acid sequence
SEQ ID NO: 18: Reverse transcriptase mutant O1+K3 (T55G+D524A) nucleic acid sequence
SEQ ID NO: 19: Reverse transcriptase mutant O1+K2 (T55G+D524N) nucleic acid sequence
SEQ ID NO: 20: Reverse transcriptase mutant O1+LT (T55G+H204R+M289L+T306K+F309N) nucleic acid sequence
SEQ ID NO: 21: Reverse transcriptase mutant 02(T55A) amino acid sequence
SEQ ID NO: 22: Reverse transcriptase mutant 03(T55S) amino acid sequence
SEQ ID NO: 23: Reverse transcriptase mutant P13(T55K) amino acid sequence
SEQ ID NO: 24: Reverse transcriptase mutant 02(T55A) nucleic acid sequence
SEQ ID NO: 25: Reverse transcriptase mutant 03(T55S) nucleic acid sequence
SEQ ID NO: 26: Reverse transcriptase mutant P13(T55K) nucleic acid sequence
SEQ ID NO: 27: Reverse transcriptase mutant D1(T287K) amino acid sequence
SEQ ID NO: 28: Reverse transcriptase mutant K1(Q291K) amino acid sequence
SEQ ID NO: 29: Reverse transcriptase mutant K4(T306K) amino acid sequence
SEQ ID NO: 30: Reverse transcriptase mutant K3(D524A) amino acid sequence
SEQ ID NO: 31: Reverse transcriptase mutant K2(D524N) amino acid sequence
SEQ ID NO: 32: Reverse transcriptase mutant LT(H204R+M289L+T306K+F309N) amino acid sequence
SEQ ID NO: 33: Reverse transcriptase mutant D1(T287K) nucleic acid sequence
SEQ ID NO: 34: Reverse transcriptase mutant K1(Q291K) nucleic acid sequence
SEQ ID NO: 35: Reverse transcriptase mutant K4(T306K) nucleic acid sequence
SEQ ID NO: 36: Reverse transcriptase mutant K3(D524A) nucleic acid sequence
SEQ ID NO: 37: Reverse transcriptase mutant K2(D524N) nucleic acid sequence
SEQ ID NO: 38: Reverse transcriptase mutant LT(H204R+M289L+T306K+F309N) nucleic acid sequence
SEQ ID NO: 39: Reverse transcriptase mutant C3+D1 amino acid sequence
SEQ ID NO: 40: Reverse transcriptase mutant C3+K1 amino acid sequence
SEQ ID NO: 41: Reverse transcriptase mutant C3+K4 amino acid sequence
SEQ ID NO: 42: Reverse transcriptase mutant C3+K3 amino acid sequence
SEQ ID NO: 43: Reverse transcriptase mutant C3+K2 amino acid sequence
SEQ ID NO: 44: Reverse transcriptase mutant C3+LT amino acid sequence
SEQ ID NO: 45: Reverse transcriptase mutant C3+D1 nucleic acid sequence
SEQ ID NO: 46: Reverse transcriptase mutant C3+K1 nucleic acid sequence
SEQ ID NO: 47: Reverse transcriptase mutant C3+K4 nucleic acid sequence
SEQ ID NO: 48: Reverse transcriptase mutant C3+K3 nucleic acid sequence
SEQ ID NO: 49: Reverse transcriptase mutant C3+K2 nucleic acid sequence
SEQ ID NO: 50: Reverse transcriptase mutant C3+LT nucleic acid sequence
SEQ ID NO: 51: Reverse transcriptase mutant C5(D209P+I212A) amino acid sequence
SEQ ID NO: 52: Reverse transcriptase mutant C3+C5 amino acid sequence
SEQ ID NO: 53: Reverse transcriptase mutant C5 nucleic acid sequence
SEQ ID NO: 54: Reverse transcriptase mutant C3+C5 nucleic acid sequence
SEQ ID NO: 55: Reverse transcriptase mutant P12+D1 amino acid sequence
SEQ ID NO: 56: Reverse transcriptase mutant P12+LT amino acid sequence
SEQ ID NO: 57: Reverse transcriptase mutant P12+K1 amino acid sequence
SEQ ID NO: 58: Reverse transcriptase mutant P12+K2 amino acid sequence
SEQ ID NO: 59: Reverse transcriptase mutant P12+K3 amino acid sequence
SEQ ID NO: 60: Reverse transcriptase mutant P12+K4 amino acid sequence
SEQ ID NO: 61: Reverse transcriptase mutant O1+C5 amino acid sequence
SEQ ID NO: 62: Reverse transcriptase mutant P12+C5 amino acid sequence SEQ ID NO: 63: Reverse transcriptase mutant P12+D1 nucleic acid sequence
SEQ ID NO: 64: Reverse transcriptase mutant P12+LT nucleic acid sequence
SEQ ID NO: 65: Reverse transcriptase mutant P12+K1 nucleic acid sequence
SEQ ID NO: 66: Reverse transcriptase mutant P12+K2 nucleic acid sequence
SEQ ID NO: 67: Reverse transcriptase mutant P12+K3 nucleic acid sequence
SEQ ID NO: 68: Reverse transcriptase mutant P12+K4 nucleic acid sequence
SEQ ID NO: 69: Reverse transcriptase mutant O1+C5 nucleic acid sequence
SEQ ID NO: 70: Reverse transcriptase mutant P12+C5 nucleic acid sequence

The invention claimed is:

1. A reverse transcriptase mutant comprising an amino acid sequence having at least 90% sequence identity to a wild-type Moloney murine leukemia virus (MMLV) reverse transcriptase of SEQ ID NO: 1, wherein an amino acid mutation at a position corresponding to position 55 of SEQ ID NO: 1 is a replacement of threonine with glycine or amino acids having polar acidic functional group side chains, wherein the reverse transcriptase mutant has increased heat resistance.

2. The reverse transcriptase mutant according to claim 1, wherein the mutation is T55D.

3. The reverse transcriptase mutant according to claim 1, further comprising one or more amino acid replacements selected from the group consisting of (1) to (8):

(1) A54P,
(2) T287K,
(3) Q291K,
(4) T306K,
(5) D524A,
(6) D524N,
(7) H204R, M289L, T306K and F309N, and
(8) D209P and I212A.

4. The reverse transcriptase mutant according to claim 1, which lacks ribonuclease H activity.

5. A composition comprising the reverse transcriptase mutant according to claim 1.

6. A kit comprising the reverse transcriptase mutant according to claim 1.

* * * * *

SEQUENCE LISTING

```
<160> NUMBER OF SEQ ID NOS: 70

<210> SEQ ID NO 1
<211> LENGTH: 673
<212> TYPE: PRT
<213> ORGANISM: Moloney murine leukemia virus

<400> SEQUENCE: 1

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300
```

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
            325                 330                 335

Trp Gly Pro Asp Gln Gln Lys Ala Tyr Gln Glu Ile Lys Gln Ala Leu
        340                 345                 350

Leu Thr Ala Pro Ala Leu Gly Leu Pro Asp Leu Thr Lys Pro Phe Glu
    355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
        420                 425                 430

Leu Val Ile Leu Ala Pro His Ala Val Glu Ala Leu Val Lys Gln Pro
    435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
        500                 505                 510

Gln Pro Leu Pro Asp Ala Asp His Thr Trp Tyr Thr Asp Gly Ser Ser
    515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
        580                 585                 590

His Ile His Gly Glu Ile Tyr Arg Arg Arg Gly Leu Leu Thr Ser Glu
    595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
        660                 665                 670

Ile

<210> SEQ ID NO 2
<211> LENGTH: 673
<212> TYPE: PRT
<213> ORGANISM: Artificial Seuence
<220> FEATURE:
<223> OTHER INFORMATION: Reverse transcriptase variant O1(T55G) amino acid sequence

<400> SEQUENCE: 2

```
Met Thr Leu Asn Ile Glu Asp Glu His Arg Leu His Glu Thr Ser Lys
 1               5                  10                  15
Glu Pro Asp Val Ser Leu Gly Ser Thr Trp Leu Ser Asp Phe Pro Gln
            20                  25                  30
Ala Trp Ala Glu Thr Gly Gly Met Gly Leu Ala Val Arg Gln Ala Pro
        35                  40                  45
Leu Ile Ile Pro Leu Lys Ala Gly Ser Thr Pro Val Ser Ile Lys Gln
    50                  55                  60
Tyr Pro Met Ser Gln Glu Ala Arg Leu Gly Ile Lys Pro His Ile Gln
65                  70                  75                  80
Arg Leu Leu Asp Gln Gly Ile Leu Val Pro Cys Gln Ser Pro Trp Asn
                85                  90                  95
Thr Pro Leu Leu Pro Val Lys Lys Pro Gly Thr Asn Asp Tyr Arg Pro
            100                 105                 110
Val Gln Asp Leu Arg Glu Val Asn Lys Arg Val Glu Asp Ile His Pro
        115                 120                 125
Thr Val Pro Asn Pro Tyr Asn Leu Leu Ser Gly Leu Pro Pro Ser His
    130                 135                 140
Gln Trp Tyr Thr Val Leu Asp Leu Lys Asp Ala Phe Phe Cys Leu Arg
145                 150                 155                 160
Leu His Pro Thr Ser Gln Pro Leu Phe Ala Phe Glu Trp Arg Asp Pro
                165                 170                 175
Glu Met Gly Ile Ser Gly Gln Leu Thr Trp Thr Arg Leu Pro Gln Gly
            180                 185                 190
Phe Lys Asn Ser Pro Thr Leu Phe Asp Glu Ala Leu His Arg Asp Leu
        195                 200                 205
Ala Asp Phe Arg Ile Gln His Pro Asp Leu Ile Leu Leu Gln Tyr Val
    210                 215                 220
Asp Asp Leu Leu Leu Ala Ala Thr Ser Glu Leu Asp Cys Gln Gln Gly
225                 230                 235                 240
Thr Arg Ala Leu Leu Gln Thr Leu Gly Asn Leu Gly Tyr Arg Ala Ser
                245                 250                 255
Ala Lys Lys Ala Gln Ile Cys Gln Lys Gln Val Lys Tyr Leu Gly Tyr
            260                 265                 270
Leu Leu Lys Glu Gly Gln Arg Trp Leu Thr Glu Ala Arg Lys Glu Thr
        275                 280                 285
Val Met Gly Gln Pro Thr Pro Lys Thr Pro Arg Gln Leu Arg Glu Phe
    290                 295                 300
Leu Gly Thr Ala Gly Phe Cys Arg Leu Trp Ile Pro Gly Phe Ala Glu
305                 310                 315                 320
Met Ala Ala Pro Leu Tyr Pro Leu Thr Lys Thr Gly Thr Leu Phe Asn
                325                 330                 335
Trp Gly Pro Asp Gln Gln Lys Ala Tyr Gln Glu Ile Lys Gln Ala Leu
            340                 345                 350
Leu Thr Ala Pro Ala Leu Gly Leu Pro Asp Leu Thr Lys Pro Phe Glu
        355                 360                 365
Leu Phe Val Asp Glu Lys Gln Gly Tyr Ala Lys Gly Val Leu Thr Gln
    370                 375                 380
Lys Leu Gly Pro Trp Arg Arg Pro Val Ala Tyr Leu Ser Lys Lys Leu
385                 390                 395                 400
```

```
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
            420                 425                 430
Leu Val Ile Leu Ala Pro His Ala Val Glu Ala Leu Val Lys Gln Pro
        435                 440                 445
Pro Asp Arg Trp Leu Ser Asn Ala Arg Met Thr His Tyr Gln Ala Leu
450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
            500                 505                 510
Gln Pro Leu Pro Asp Ala Asp His Thr Trp Tyr Thr Asp Gly Ser Ser
        515                 520                 525
Leu Leu Gln Glu Gly Gln Arg Lys Ala Gly Ala Ala Val Thr Thr Glu
530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Lys Met Ala Glu Gly
                565                 570                 575
Lys Lys Leu Asn Val Tyr Thr Asp Ser Arg Tyr Ala Phe Ala Thr Ala
            580                 585                 590
His Ile His Gly Glu Ile Tyr Arg Arg Arg Gly Leu Leu Thr Ser Glu
        595                 600                 605
Gly Lys Glu Ile Lys Asn Lys Asp Glu Ile Leu Ala Leu Leu Lys Ala
610                 615                 620
Leu Phe Leu Pro Lys Arg Leu Ser Ile Ile His Cys Pro Gly His Gln
625                 630                 635                 640
Lys Gly His Ser Ala Glu Ala Arg Gly Asn Arg Met Ala Asp Gln Ala
                645                 650                 655
Ala Arg Lys Ala Ala Ile Thr Glu Thr Pro Asp Thr Ser Thr Leu Leu
            660                 665                 670
Ile

<210> SEQ ID NO 3
<211> LENGTH: 673
<212> TYPE: PRT
<213> ORGANISM: Artificial Seuence
<220> FEATURE:
<223> OTHER INFORMATION: Reverse transcriptase variant P12(T55D) amino
      acid sequence

<400> SEQUENCE: 3

Met Thr Leu Asn Ile Glu Asp Glu His Arg Leu His Glu Thr Ser Lys
1               5                   10                  15
Glu Pro Asp Val Ser Leu Gly Ser Thr Trp Leu Ser Asp Phe Pro Gln
                20                  25                  30
Ala Trp Ala Glu Thr Gly Gly Met Gly Leu Ala Val Arg Gln Ala Pro
            35                  40                  45
Leu Ile Ile Pro Leu Lys Ala Asp Ser Thr Pro Val Ser Ile Lys Gln
        50                  55                  60
Tyr Pro Met Ser Gln Glu Ala Arg Leu Gly Ile Lys Pro His Ile Gln
65                  70                  75                  80
```

```
Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
        290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
```

```
                500             505             510
Gln Pro Leu Pro Asp Ala Asp His Thr Trp Tyr Thr Asp Gly Ser Ser
            515                 520                 525
Leu Leu Gln Glu Gly Gln Arg Lys Ala Gly Ala Ala Val Thr Thr Glu
            530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Lys Met Ala Glu Gly
                565                 570                 575
Lys Lys Leu Asn Val Tyr Thr Asp Ser Arg Tyr Ala Phe Ala Thr Ala
            580                 585                 590
His Ile His Gly Glu Ile Tyr Arg Arg Arg Gly Leu Leu Thr Ser Glu
            595                 600                 605
Gly Lys Glu Ile Lys Asn Lys Asp Glu Ile Leu Ala Leu Leu Lys Ala
            610                 615                 620
Leu Phe Leu Pro Lys Arg Leu Ser Ile Ile His Cys Pro Gly His Gln
625                 630                 635                 640
Lys Gly His Ser Ala Glu Ala Arg Gly Asn Arg Met Ala Asp Gln Ala
                645                 650                 655
Ala Arg Lys Ala Ala Ile Thr Glu Thr Pro Asp Thr Ser Thr Leu Leu
            660                 665                 670
Ile
```

<210> SEQ ID NO 4
<211> LENGTH: 673
<212> TYPE: PRT
<213> ORGANISM: Artificial Seuence
<220> FEATURE:
<223> OTHER INFORMATION: Reverse transcriptase variant C3(T55G+A54P) amino acid sequence

<400> SEQUENCE: 4

```
Met Thr Leu Asn Ile Glu Asp Glu His Arg Leu His Glu Thr Ser Lys
1               5                   10                  15
Glu Pro Asp Val Ser Leu Gly Ser Thr Trp Leu Ser Asp Phe Pro Gln
                20                  25                  30
Ala Trp Ala Glu Thr Gly Gly Met Gly Leu Ala Val Arg Gln Ala Pro
            35                  40                  45
Leu Ile Ile Pro Leu Lys Pro Gly Ser Thr Pro Val Ser Ile Lys Gln
        50                  55                  60
Tyr Pro Met Ser Gln Glu Ala Arg Leu Gly Ile Lys Pro His Ile Gln
65                  70                  75                  80
Arg Leu Leu Asp Gln Gly Ile Leu Val Pro Cys Gln Ser Pro Trp Asn
                85                  90                  95
Thr Pro Leu Leu Pro Val Lys Lys Pro Gly Thr Asn Asp Tyr Arg Pro
            100                 105                 110
Val Gln Asp Leu Arg Glu Val Asn Lys Arg Val Glu Asp Ile His Pro
        115                 120                 125
Thr Val Pro Asn Pro Tyr Asn Leu Leu Ser Gly Leu Pro Pro Ser His
    130                 135                 140
Gln Trp Tyr Thr Val Leu Asp Leu Lys Asp Ala Phe Phe Cys Leu Arg
145                 150                 155                 160
Leu His Pro Thr Ser Gln Pro Leu Phe Ala Phe Glu Trp Arg Asp Pro
                165                 170                 175
Glu Met Gly Ile Ser Gly Gln Leu Thr Trp Thr Arg Leu Pro Gln Gly
```

```
                180                 185                 190
    Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
    225                 230                 235                 240

Thr Arg Ala Leu Leu Gln Thr Leu Gly Asn Leu Gly Tyr Arg Ala Ser
                    245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Gln Pro Thr Pro Lys Thr Pro Arg Gln Leu Arg Glu Phe
            290                 295                 300

Leu Gly Thr Ala Gly Phe Cys Arg Leu Trp Ile Pro Gly Phe Ala Glu
    305                 310                 315                 320

Met Ala Ala Pro Leu Tyr Pro Leu Thr Lys Thr Gly Thr Leu Phe Asn
                    325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
    385                 390                 395                 400

Asp Pro Val Ala Ala Gly Trp Pro Pro Cys Leu Arg Met Val Ala Ala
                    405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
    465                 470                 475                 480

Pro Ala Thr Leu Leu Pro Leu Pro Glu Glu Gly Leu Gln His Asn Cys
                    485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
                515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
    545                 550                 555                 560

Arg Ala Glu Leu Ile Ala Leu Thr Gln Ala Leu Lys Met Ala Glu Gly
                    565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Arg Gly Leu Leu Thr Ser Glu
                595                 600                 605
```

-continued

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
        660                 665                 670

Ile

<210> SEQ ID NO 5
<211> LENGTH: 673
<212> TYPE: PRT
<213> ORGANISM: Artificial Seuence
<220> FEATURE:
<223> OTHER INFORMATION: Reverse transcriptase variant O1+D1(T55G+T287K)
      amino acid sequence

<400> SEQUENCE: 5

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Gly Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Lys
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile

<210> SEQ ID NO 6
<211> LENGTH: 673
<212> TYPE: PRT

<213> ORGANISM: Artificial Seuence
<220> FEATURE:
<223> OTHER INFORMATION: Reverse transcriptase variant O1+K1(T55G+Q291K) amino acid sequence

<400> SEQUENCE: 6

| | | | | | | | | | | | | | | |
|---|---|---|---|---|---|---|---|---|---|---|---|---|---|---|
| Met | Thr | Leu | Asn | Ile | Glu | Asp | Glu | His | Arg | Leu | His | Glu | Thr | Ser | Lys |
| 1 | | | | 5 | | | | | 10 | | | | | 15 | |
| Glu | Pro | Asp | Val | Ser | Leu | Gly | Ser | Thr | Trp | Leu | Ser | Asp | Phe | Pro | Gln |
| | | | 20 | | | | | 25 | | | | | 30 | | |
| Ala | Trp | Ala | Glu | Thr | Gly | Gly | Met | Gly | Leu | Ala | Val | Arg | Gln | Ala | Pro |
| | | 35 | | | | | 40 | | | | | 45 | | | |
| Leu | Ile | Ile | Pro | Leu | Lys | Ala | Gly | Ser | Thr | Pro | Val | Ser | Ile | Lys | Gln |
| 50 | | | | | 55 | | | | | 60 | | | | | |
| Tyr | Pro | Met | Ser | Gln | Glu | Ala | Arg | Leu | Gly | Ile | Lys | Pro | His | Ile | Gln |
| 65 | | | | 70 | | | | | 75 | | | | | 80 | |
| Arg | Leu | Leu | Asp | Gln | Gly | Ile | Leu | Val | Pro | Cys | Gln | Ser | Pro | Trp | Asn |
| | | | 85 | | | | | 90 | | | | | 95 | | |
| Thr | Pro | Leu | Leu | Pro | Val | Lys | Lys | Pro | Gly | Thr | Asn | Asp | Tyr | Arg | Pro |
| | | | 100 | | | | | 105 | | | | | 110 | | |
| Val | Gln | Asp | Leu | Arg | Glu | Val | Asn | Lys | Arg | Val | Glu | Asp | Ile | His | Pro |
| | | | 115 | | | | | 120 | | | | | 125 | | |
| Thr | Val | Pro | Asn | Pro | Tyr | Asn | Leu | Leu | Ser | Gly | Leu | Pro | Pro | Ser | His |
| 130 | | | | | 135 | | | | | 140 | | | | | |
| Gln | Trp | Tyr | Thr | Val | Leu | Asp | Leu | Lys | Asp | Ala | Phe | Phe | Cys | Leu | Arg |
| 145 | | | | 150 | | | | | 155 | | | | | 160 | |
| Leu | His | Pro | Thr | Ser | Gln | Pro | Leu | Phe | Ala | Phe | Glu | Trp | Arg | Asp | Pro |
| | | | | 165 | | | | | 170 | | | | | 175 | |
| Glu | Met | Gly | Ile | Ser | Gly | Gln | Leu | Thr | Trp | Thr | Arg | Leu | Pro | Gln | Gly |
| | | | 180 | | | | | 185 | | | | | 190 | | |
| Phe | Lys | Asn | Ser | Pro | Thr | Leu | Phe | Asp | Glu | Ala | Leu | His | Arg | Asp | Leu |
| | | | 195 | | | | | 200 | | | | | 205 | | |
| Ala | Asp | Phe | Arg | Ile | Gln | His | Pro | Asp | Leu | Ile | Leu | Leu | Gln | Tyr | Val |
| 210 | | | | | 215 | | | | | 220 | | | | | |
| Asp | Asp | Leu | Leu | Leu | Ala | Ala | Thr | Ser | Glu | Leu | Asp | Cys | Gln | Gln | Gly |
| 225 | | | | | 230 | | | | | 235 | | | | | 240 |
| Thr | Arg | Ala | Leu | Leu | Gln | Thr | Leu | Gly | Asn | Leu | Gly | Tyr | Arg | Ala | Ser |
| | | | | 245 | | | | | 250 | | | | | 255 | |
| Ala | Lys | Lys | Ala | Gln | Ile | Cys | Gln | Lys | Gln | Val | Lys | Tyr | Leu | Gly | Tyr |
| | | | 260 | | | | | 265 | | | | | 270 | | |
| Leu | Leu | Lys | Glu | Gly | Gln | Arg | Trp | Leu | Thr | Glu | Ala | Arg | Lys | Glu | Thr |
| | | 275 | | | | | 280 | | | | | 285 | | | |
| Val | Met | Gly | Lys | Pro | Thr | Pro | Lys | Thr | Pro | Arg | Gln | Leu | Arg | Glu | Phe |
| 290 | | | | | 295 | | | | | 300 | | | | | |
| Leu | Gly | Thr | Ala | Gly | Phe | Cys | Arg | Leu | Trp | Ile | Pro | Gly | Phe | Ala | Glu |
| 305 | | | | | 310 | | | | | 315 | | | | | 320 |
| Met | Ala | Ala | Pro | Leu | Tyr | Pro | Leu | Thr | Lys | Thr | Gly | Thr | Leu | Phe | Asn |
| | | | | 325 | | | | | 330 | | | | | 335 | |
| Trp | Gly | Pro | Asp | Gln | Gln | Lys | Ala | Tyr | Gln | Glu | Ile | Lys | Gln | Ala | Leu |
| | | | 340 | | | | | 345 | | | | | 350 | | |
| Leu | Thr | Ala | Pro | Ala | Leu | Gly | Leu | Pro | Asp | Leu | Thr | Lys | Pro | Phe | Glu |
| | | 355 | | | | | 360 | | | | | 365 | | | |
| Leu | Phe | Val | Asp | Glu | Lys | Gln | Gly | Tyr | Ala | Lys | Gly | Val | Leu | Thr | Gln |
| 370 | | | | | 375 | | | | | 380 | | | | | |

```
Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Leu Leu Thr Ser Glu
            595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
            660                 665                 670

Ile

<210> SEQ ID NO 7
<211> LENGTH: 673
<212> TYPE: PRT
<213> ORGANISM: Artificial Seuence
<220> FEATURE:
<223> OTHER INFORMATION: Reverse transcriptase variant O1+K4
      (T55G+T306K) amino acid sequence

<400> SEQUENCE: 7

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
            35                  40                  45

Leu Ile Ile Pro Leu Lys Ala Gly Ser Thr Pro Val Ser Ile Lys Gln
            50                  55                  60
```

```
Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
                 85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
```

```
                    485                 490                 495
Leu Asp Ile Leu Ala Glu Ala His Gly Thr Arg Pro Asp Leu Thr Asp
                500                 505                 510
Gln Pro Leu Pro Asp Ala Asp His Thr Trp Tyr Thr Asp Gly Ser Ser
                515                 520                 525
Leu Leu Gln Glu Gly Gln Arg Lys Ala Gly Ala Val Thr Thr Glu
        530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Lys Met Ala Glu Gly
                565                 570                 575
Lys Lys Leu Asn Val Tyr Thr Asp Ser Arg Tyr Ala Phe Ala Thr Ala
                580                 585                 590
His Ile His Gly Glu Ile Tyr Arg Arg Arg Gly Leu Leu Thr Ser Glu
                595                 600                 605
Gly Lys Glu Ile Lys Asn Lys Asp Glu Ile Leu Ala Leu Leu Lys Ala
                610                 615                 620
Leu Phe Leu Pro Lys Arg Leu Ser Ile Ile His Cys Pro Gly His Gln
625                 630                 635                 640
Lys Gly His Ser Ala Glu Ala Arg Gly Asn Arg Met Ala Asp Gln Ala
                645                 650                 655
Ala Arg Lys Ala Ala Ile Thr Glu Thr Pro Asp Thr Ser Thr Leu Leu
                660                 665                 670
Ile

<210> SEQ ID NO 8
<211> LENGTH: 673
<212> TYPE: PRT
<213> ORGANISM: Artificial Seuence
<220> FEATURE:
<223> OTHER INFORMATION: Reverse transcriptase variant O1+K3
      (T55G+D524A) amino acid sequence

<400> SEQUENCE: 8

Met Thr Leu Asn Ile Glu Asp Glu His Arg Leu His Glu Thr Ser Lys
1               5                   10                  15
Glu Pro Asp Val Ser Leu Gly Ser Thr Trp Leu Ser Asp Phe Pro Gln
                20                  25                  30
Ala Trp Ala Glu Thr Gly Gly Met Gly Leu Ala Val Arg Gln Ala Pro
            35                  40                  45
Leu Ile Ile Pro Leu Lys Ala Gly Ser Thr Pro Val Ser Ile Lys Gln
        50                  55                  60
Tyr Pro Met Ser Gln Glu Ala Arg Leu Gly Ile Lys Pro His Ile Gln
65                  70                  75                  80
Arg Leu Leu Asp Gln Gly Ile Leu Val Pro Cys Gln Ser Pro Trp Asn
                85                  90                  95
Thr Pro Leu Leu Pro Val Lys Lys Pro Gly Thr Asn Asp Tyr Arg Pro
                100                 105                 110
Val Gln Asp Leu Arg Glu Val Asn Lys Arg Val Glu Asp Ile His Pro
            115                 120                 125
Thr Val Pro Asn Pro Tyr Asn Leu Leu Ser Gly Leu Pro Pro Ser His
        130                 135                 140
Gln Trp Tyr Thr Val Leu Asp Leu Lys Asp Ala Phe Phe Cys Leu Arg
145                 150                 155                 160
Leu His Pro Thr Ser Gln Pro Leu Phe Ala Phe Glu Trp Arg Asp Pro
```

-continued

```
                165                 170                 175
Glu Met Gly Ile Ser Gly Gln Leu Thr Trp Thr Arg Leu Pro Gln Gly
            180                 185                 190
Phe Lys Asn Ser Pro Thr Leu Phe Asp Glu Ala Leu His Arg Asp Leu
        195                 200                 205
Ala Asp Phe Arg Ile Gln His Pro Asp Leu Ile Leu Leu Gln Tyr Val
    210                 215                 220
Asp Asp Leu Leu Leu Ala Ala Thr Ser Glu Leu Asp Cys Gln Gln Gly
225                 230                 235                 240
Thr Arg Ala Leu Leu Gln Thr Leu Gly Asn Leu Gly Tyr Arg Ala Ser
                245                 250                 255
Ala Lys Lys Ala Gln Ile Cys Gln Lys Gln Val Lys Tyr Leu Gly Tyr
            260                 265                 270
Leu Leu Lys Glu Gly Gln Arg Trp Leu Thr Glu Ala Arg Lys Glu Thr
        275                 280                 285
Val Met Gly Gln Pro Thr Pro Lys Thr Pro Arg Gln Leu Arg Glu Phe
    290                 295                 300
Leu Gly Thr Ala Gly Phe Cys Arg Leu Trp Ile Pro Gly Phe Ala Glu
305                 310                 315                 320
Met Ala Ala Pro Leu Tyr Pro Leu Thr Lys Thr Gly Thr Leu Phe Asn
                325                 330                 335
Trp Gly Pro Asp Gln Gln Lys Ala Tyr Gln Glu Ile Lys Gln Ala Leu
            340                 345                 350
Leu Thr Ala Pro Ala Leu Gly Leu Pro Asp Leu Thr Lys Pro Phe Glu
        355                 360                 365
Leu Phe Val Asp Glu Lys Gln Gly Tyr Ala Lys Gly Val Leu Thr Gln
    370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
            420                 425                 430
Leu Val Ile Leu Ala Pro His Ala Val Glu Ala Leu Val Lys Gln Pro
        435                 440                 445
Pro Asp Arg Trp Leu Ser Asn Ala Arg Met Thr His Tyr Gln Ala Leu
    450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
            500                 505                 510
Gln Pro Leu Pro Asp Ala Asp His Thr Trp Tyr Thr Ala Gly Ser Ser
        515                 520                 525
Leu Leu Gln Glu Gly Gln Arg Lys Ala Gly Ala Ala Val Thr Thr Glu
    530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Lys Met Ala Glu Gly
                565                 570                 575
Lys Lys Leu Asn Val Tyr Thr Asp Ser Arg Tyr Ala Phe Ala Thr Ala
            580                 585                 590
```

His Ile His Gly Glu Ile Tyr Arg Arg Gly Leu Leu Thr Ser Glu
            595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile

<210> SEQ ID NO 9
<211> LENGTH: 673
<212> TYPE: PRT
<213> ORGANISM: Artificial Seuence
<220> FEATURE:
<223> OTHER INFORMATION: Reverse transcriptase variant O1+K2
      (T55G+D524N) amino acid sequence

<400> SEQUENCE: 9

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Gly Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

```
Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asn Gly Ser Ser
            515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Arg Gly Leu Leu Thr Ser Glu
            595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile
```

<210> SEQ ID NO 10
<211> LENGTH: 673
<212> TYPE: PRT
<213> ORGANISM: Artificial Seuence
<220> FEATURE:
<223> OTHER INFORMATION: Reverse transcriptase variant O1+LT (T55G+H204R+M289L+T306K+F309N) amino acid sequence

<400> SEQUENCE: 10

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Gly Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu Arg Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Leu Gly Gln Pro Thr Pro Lys Thr Pro Arg Gln Leu Arg Glu Phe
    290                 295                 300

Leu Gly Lys Ala Gly Asn Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365
```

```
Leu Phe Val Asp Glu Lys Gln Gly Tyr Ala Lys Gly Val Leu Thr Gln
                370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                    405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                    485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
                515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                    565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                    645                 650                 655

Ala Arg Lys Ala Ala Ile Thr Glu Thr Pro Asp Thr Ser Thr Leu Leu
                660                 665                 670

Ile

<210> SEQ ID NO 11
<211> LENGTH: 2019
<212> TYPE: DNA
<213> ORGANISM: Moloney murine leukemia virus

<400> SEQUENCE: 11
atgaccctaa atatagaaga tgagcatcgg ctacatgaga cctcaaaaga gccagatgtt      60
tctctagggt ccacatggct gtctgatttt cctcaggcct gggcggaaac cggggggcatg    120 ggactggcag ttcgccaagc tcctctgatc atacctctga agcaacctc tacccccgtg      180 tccataaaac aatacccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
```

```
aagcgggtgg aagacatcca ccccaccgtg cccaaccctt acaacctctt gagcgggctc    420
ccaccgtccc accagtggta cactgtgctt gatttaaagg atgccttttt ctgcctgaga    480
ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaaagaggg tcagagatgg    840
ctgactgagg ccagaaaaga gactgtgatg gggcagccta ctccgaagac ccctcgacaa    900
ctaagggagt tcctagggac ggcaggcttc tgtcgcctct ggatccctgg gtttgcagaa    960
atggcagccc ccttgtaccc tctcaccaaa acggggactc tgtttaattg gggcccagac   1020
caacaaaagg cctatcaaga aatcaagcaa gctcttctaa ctgccccagc cctggggttg   1080
ccagatttga ctaagccctt tgaactcttt gtcgacgaga agcagggcta cgccaaaggt   1140
gtcctaacgc aaaaactggg accttggcgt cggccggtgg cctacctgtc caaaaagcta   1200
gacccagtag cagctgggtg gccccccttgc ctacggatgg tagcagccat tgccgtactg   1260
acaaaggatg caggcaagct aaccatggga cagccactag tcattctggc cccccatgca   1320
gtagaggcac tagtcaaaca accccccgac cgctggcttt ccaacgcccg gatgactcac   1380
tatcaggcct gcttttgga cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggatggaag cagtctctta aagagggac agcgtaaggc gggagctgcg   1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca gcgccgaggc tagaggcaac cggatggctg accaagcggc ccgaaaggca   1980
gccatcacag agactccaga cacctctacc ctcctcata                          2019
```

<210> SEQ ID NO 12
<211> LENGTH: 2019
<212> TYPE: DNA
<213> ORGANISM: Artificial Seuence
<220> FEATURE:
<223> OTHER INFORMATION: Reverse transcriptase variant O1(T55G) nucleic
      acid sequence

<400> SEQUENCE: 12

```
atgaccctaa atatagaaga tgagcatcgg ctacatgaga cctcaaaaga gccagatgtt     60
tctctagggt ccacatggct gtctgatttt cctcaggcct gggcggaaac cgggggcatg    120
ggactggcag ttcgccaagc tcctctgatc atacctctga agcaggttc tacccccgtg    180 tccataaaac aatacccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
```

```
aagcgggtgg aagacatcca ccccaccgtg cccaacccTT acaacctctt gagcgggctc    420
ccaccgtccc accagtggta cactgtgctt gatttaaagg atgcctttTT ctgcctgaga    480
ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaagagggg tcagagatgg    840
ctgactgagg ccagaaaaga gactgtgatg gggcagccta ctccgaagac ccctcgacaa    900
ctaagggagt tcctagggac ggcaggcttc tgtcgcctct ggatccctgg gtttgcagaa    960
atggcagccc ccttgtaccc tctcaccaaa acggggactc tgtttaattg gggcccagac   1020
caacaaaagg cctatcaaga aatcaagcaa gctcttctaa ctgccccagc cctgggggttg   1080 ccagatttga ctaagccctt tgaactcttt gtcgacgaga gcagggcta cgccaaaggt   1140 gtcctaacgc aaaaactggg accttggcgt cggccggtgg cctacctgtc caaaaagcta   1200
gacccagtag cagctgggtg gccccccttgc ctacggatgg tagcagccat tgccgtactg   1260
acaaaggatg caggcaagct aaccatggga cagccactag tcattctggc cccccatgca   1320
gtagaggcac tagtcaaaca ccccccgac cgctggcttt ccaacgcccg gatgactcac   1380
tatcaggcct gcttttgga cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggatggaag cagtctctta caagagggac agcgtaaggc gggagctgcg   1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca cgccgaggc tagaggcaac cggatggctg accaagcggc ccgaaaggca   1980
gccatcacag agactccaga cacctctacc ctcctcata                          2019
```

<210> SEQ ID NO 13
<211> LENGTH: 2019
<212> TYPE: DNA
<213> ORGANISM: Artificial Seuence
<220> FEATURE:
<223> OTHER INFORMATION: Reverse transcriptase variant P12(T55D) nucleic acid sequence

<400> SEQUENCE: 13

```
atgaccctaa atatagaaga tgagcatcgg ctacatgaga cctcaaaaga gccagatgtt     60
tctctagggt ccacatggct gtctgattTT cctcaggcct gggcggaaac cggggggcatg    120 ggactggcag ttcgccaagc tcctctgatc atacctctga agcagactc taccccccgtg    180 tccataaaac aataccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
```

```
aagcgggtgg aagacatcca ccccaccgtg cccaacccct acaacctctt gagcgggctc    420
ccaccgtccc accagtggta cactgtgctt gatttaaagg atgccttttt ctgcctgaga    480
ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaaagaggg tcagagatgg    840
ctgactgagg ccagaaaaga gactgtgatg ggcagccta ctccgaagac ccctcgacaa     900
ctaagggagt cctagggac ggcaggcttc tgtcgcctct ggatccctgg gtttgcagaa      960
atggcagccc ccttgtaccc tctcaccaaa acggggactc tgtttaattg gggcccagac   1020
caacaaaagg cctatcaaga aatcaagcaa gctcttctaa ctgccccagc cctgggggttg  1080 ccagatttga ctaagcccct tgaactcttt gtcgacgaga agcagggcta cgccaaaggt   1140
gtcctaacgc aaaaactggg accttggcgt cggccggtgg cctacctgtc caaaaagcta   1200
gacccagtag cagctgggtg gccccttgc ctacggatgg tagcagccat tgccgtactg    1260
acaaaggatg caggcaagct aaccatggga cagccactag tcattctggc cccccatgca   1320
gtagaggcac tagtcaaaca ccccccgac cgctggcttt ccaacgcccg gatgactcac    1380
tatcaggcct gcttttgga cacggaccgg gtccagttcg gaccggtggt agccctgaac    1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggatggaag cagtctctta aagagggac agcgtaaggc gggagctgcg    1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca cgcgccgaggc tagaggcaac cggatggctg accaagcggc ccgaaaggca   1980
gccatcacag agactccaga cacctctacc ctcctcata                           2019
```

<210> SEQ ID NO 14
<211> LENGTH: 2019
<212> TYPE: DNA
<213> ORGANISM: Artificial Seuence
<220> FEATURE:
<223> OTHER INFORMATION: Reverse transcriptase variant C3(T55G+A54P)
    nucleic acid sequence

<400> SEQUENCE: 14

```
atgaccctaa atatagaaga tgagcatcgg ctacatgaga cctcaaaaga gccagatgtt     60
tctctagggt ccacatggct gtctgatttt cctcaggcct gggcggaaac cggggggcatg   120 ggactggcag ttcgccaagc tcctctgatc atacctctga aaccgggttc tacccccgtg    180
tccataaaac aatacccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
```

```
aagcgggtgg aagacatcca ccccaccgtg cccaacccct acaacctctt gagcgggctc    420
ccaccgtccc accagtggta cactgtgctt gatttaaagg atgccttttt ctgcctgaga    480
ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaaagaggg tcagagatgg    840
ctgactgagg ccagaaaaga gactgtgatg gggcagccta ctccgaagac ccctcgacaa    900
ctaagggagt tcctagggac ggcaggcttc tgtcgcctct ggatccctgg gtttgcagaa    960
atggcagccc ccttgtaccc tctcaccaaa acggggactc tgtttaattg gggcccagac   1020
caacaaaagg cctatcaaga aatcaagcaa gctcttctaa ctgccccagc cctggggttg   1080
ccagatttga ctaagccctt tgaactcttt gtcgacgaga agcagggcta cgccaaaggt   1140
gtcctaacgc aaaaactggg accttggcgt cggccggtgg cctacctgtc caaaaagcta   1200
gacccagtag cagctgggtg gccccccttgc ctacggatgg tagcagccat tgccgtactg   1260
acaaaggatg caggcaagct aaccatggga cagccactag tcattctggc cccccatgca   1320
gtagaggcac tagtcaaaca ccccccgac cgctggcttt ccaacgcccg gatgactcac   1380
tatcaggcct gcttttgga cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggatggaag cagtctctta aagagggac agcgtaaggc gggagctgcg   1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca gcgccgaggc tagaggcaac cggatggctg accaagcggc ccgaaaggca   1980
gccatcacag agactccaga cacctctacc ctcctcata                          2019
```

<210> SEQ ID NO 15
<211> LENGTH: 2019
<212> TYPE: DNA
<213> ORGANISM: Artificial Seuence
<220> FEATURE:
<223> OTHER INFORMATION: Reverse transcriptase variant O1+D1(T55G+T287K)
      nucleic acid sequence

<400> SEQUENCE: 15

```
atgaccctaa atatagaaga tgagcatcgg ctacatgaga cctcaaaaga gccagatgtt     60
tctctagggt ccacatggct gtctgatttt cctcaggcct gggcggaaac cgggggcatg    120
ggactggcag ttcgccaagc tcctctgatc atacctctga aagcaggttc taccccccgtg    180 tccataaaac aataccccat gtcacaagaa gccagactgg ggatcaagcc cacatacag     240 agactgttgg accagggaat actggtaccc tgccagtccc cctggaacac gcccctgcta    300
cccgttaaga aaccagggac taatgattat aggcctgtcc aggatctgag agaagtcaac    360
```

| | |
|---|---|
| aagcgggtgg aagacatcca ccccaccgtg cccaaccctt acaacctctt gagcgggctc | 420 |
| ccaccgtccc accagtggta cactgtgctt gatttaaagg atgccttttt ctgcctgaga | 480 |
| ctccacccca ccagtcagcc tctcttcgcc tttgagtgga gagatccaga gatgggaatc | 540 |
| tcaggacaat tgacctggac cagactccca cagggtttca aaaacagtcc caccctgttt | 600 |
| gatgaggcac tgcacagaga cctagcagac ttccggatcc agcacccaga cttgatcctg | 660 |
| ctacagtacg tggatgactt actgctggcc gccacttctg agctagactg ccaacaaggt | 720 |
| actcgggccc tgttacaaac cctagggaac ctcgggtatc gggcctcggc caagaaagcc | 780 |
| caaatttgcc agaaacaggt caagtatctg gggtatcttc taaaagaggg tcagagatgg | 840 |
| ctgactgagg ccagaaaaga gaaagtgatg gggcagccta ctccgaagac ccctcgacaa | 900 |
| ctaagggagt cctagggac ggcaggcttc tgtcgcctct ggatccctgg gtttgcagaa | 960 |
| atggcagccc ccttgtaccc tctcaccaaa acggggactc tgtttaattg gggcccagac | 1020 |
| caacaaaagg cctatcaaga aatcaagcaa gctcttctaa ctgccccagc cctggggttg | 1080 |
| ccagatttga ctaagcccct tgaactcttt gtcgacgaga agcagggcta cgccaaaggt | 1140 |
| gtcctaacgc aaaaactggg accttggcgt cggccggtgg cctacctgtc caaaaagcta | 1200 |
| gacccagtag cagctgggtg gccccttgc ctacggatgg tagcagccat tgccgtactg | 1260 |
| acaaaggatg caggcaagct aaccatggga cagccactag tcattctggc cccccatgca | 1320 |
| gtagaggcac tagtcaaaca ccccccgac cgctggcttt ccaacgcccg gatgactcac | 1380 |
| tatcaggcct gcttttgga cacggaccgg gtccagttcg gaccggtggt agccctgaac | 1440 |
| ccggctacgc tgctcccact gcctgaggaa gggctgcaac acaactgcct tgatatcctg | 1500 |
| gccgaagccc acggaacccg acccgaccta acggaccagc cgctcccaga cgccgaccac | 1560 |
| acctggtaca cggatggaag cagtctctta aagagggac agcgtaaggc gggagctgcg | 1620 |
| gtgaccaccg agaccgaggt aatctgggct aaagccctgc cagccgggac atccgctcag | 1680 |
| cgggctgaac tgatagcact cacccaggcc ctaaagatgg cagaaggtaa gaagctaaat | 1740 |
| gtttatactg atagccgtta tgcttttgct actgcccata tccatggaga aatatacaga | 1800 |
| aggcgtgggt tgctcacatc agaaggcaaa gagatcaaaa ataaagacga gatcttggcc | 1860 |
| ctactaaaag ccctctttct gcccaaaaga cttagcataa tccattgtcc aggacatcaa | 1920 |
| aagggacaca cgccgaggc tagaggcaac cggatggctg accaagcggc ccgaaaggca | 1980 |
| gccatcacag agactccaga cacctctacc ctcctcata | 2019 |

<210> SEQ ID NO 16
<211> LENGTH: 2019
<212> TYPE: DNA
<213> ORGANISM: Artificial Seuence
<220> FEATURE:
<223> OTHER INFORMATION: Reverse transcriptase variant O1+K1(T55G+Q291K)
      nucleic acid sequence

<400> SEQUENCE: 16

| | |
|---|---|
| atgaccctaa atatagaaga tgagcatcgg ctacatgaga cctcaaaaga gccagatgtt | 60 |
| tctctagggt ccacatggct gtctgatttt cctcaggcct gggcggaaac cggggggcatg | 120 |
| ggactggcag ttcgccaagc tcctctgatc atacctctga aagcaggttc tacccccgtg | 180 |
| tccataaaac aatacccccat gtcacaagaa gccagactgg ggatcaagcc ccacatacag | 240 |
| agactgttgg accagggaat actggtaccc tgccagtccc cctggaacac gcccctgcta | 300 |
| cccgttaaga aaccagggac taatgattat aggcctgtcc aggatctgag agaagtcaac | 360 |

```
aagcgggtgg aagacatcca cccccaccgtg cccaacccctt acaacctctt gagcgggctc    420
ccaccgtccc accagtggta cactgtgctt gatttaaagg atgccttttt ctgcctgaga    480 ctccaccccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaaagaggg tcagagatgg    840
ctgactgagg ccagaaaaga gactgtgatg gggaaaccta ctccgaagac ccctcgacaa    900
ctaagggagt tcctagggac ggcaggcttc tgtcgcctct ggatccctgg gtttgcagaa    960
atggcagccc ccttgtaccc tctcaccaaa acggggactc tgtttaattg gggcccagac   1020
caacaaaagg cctatcaaga aatcaagcaa gctcttctaa ctgccccagc cctggggttg   1080
ccagatttga ctaagcccctt tgaactcttt gtcgacgaga agcagggcta cgccaaaggt   1140
gtcctaacgc aaaaactggg accttggcgt cggccggtgg cctacctgtc caaaaagcta   1200
gacccagtag cagctgggtg gccccccttgc ctacggatgg tagcagccat tgccgtactg   1260
acaaaggatg caggcaagct aaccatggga cagccactag tcattctggc ccccccatgca   1320 gtagaggcac tagtcaaaca accccccgac cgctggcttt ccaacgcccg gatgactcac   1380
tatcaggcct gcttttgga cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggatggaag cagtctctta aagagggac agcgtaaggc gggagctgcg   1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca cgcgccgaggc tagaggcaac cggatggctg accaagcggc ccgaaaggca   1980
gccatcacag agactccaga cacctctacc ctcctcata                          2019
```

<210> SEQ ID NO 17
<211> LENGTH: 2019
<212> TYPE: DNA
<213> ORGANISM: Artificial Seuence
<220> FEATURE:
<223> OTHER INFORMATION: Reverse transcriptase variant O1+K4
      (T55G+T306K) nucleic acid sequence

<400> SEQUENCE: 17

```
atgacccctaa atatagaaga tgagcatcgg ctacatgaga cctcaaaaga gccagatgtt     60
tctctagggt ccacatggct gtctgatttt cctcaggcct gggcggaaac cggggggcatg    120 ggactggcag ttcgccaagc tcctctgatc atacctctga agcaggttc tacccccgtg    180 tccataaaac aatacccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
```

```
aagcgggtgg aagacatcca ccccaccgtg cccaaccctt acaacctctt gagcgggctc    420
ccaccgtccc accagtggta cactgtgctt gatttaaagg atgcctttt  ctgcctgaga    480 ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaaagaggg tcagagatgg    840
ctgactgagg ccagaaaaga gactgtgatg gggcagccta ctccgaagac ccctcgacaa    900
ctaagggagt tcctagggaa gcaggcttc  tgtcgcctct ggatccctgg gtttgcagaa    960
atggcagccc ccttgtaccc tctcaccaaa acggggactc tgtttaattg gggcccagac   1020
caacaaaagg cctatcaaga aatcaagcaa gctcttctaa ctgccccagc cctggggttg   1080
ccagatttga ctaagccctt tgaactcttt gtcgacgaga agcagggcta cgccaaaggt   1140
gtcctaacgc aaaaactggg accttggcgt cggccggtgg cctacctgtc caaaaagcta   1200
gacccagtag cagctgggtg gccccttgc  ctacggatgg tagcagccat tgccgtactg   1260
acaaaggatg caggcaagct aaccatggga cagccactag tcattctggc cccccatgca   1320
gtagaggcac tagtcaaaca ccccccgac  cgctggcttt ccaacgcccg gatgactcac   1380
tatcaggcct gcttttgga  cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggatggaag cagtctctta aagagggaca gcgtaaggc  gggagctgcg   1620 gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca cgcgccgaggc tagaggcaac cggatggctg accaagcggc ccgaaaggca   1980
gccatcacag agactccaga cacctctacc ctcctcata                          2019
```

<210> SEQ ID NO 18
<211> LENGTH: 2019
<212> TYPE: DNA
<213> ORGANISM: Artificial Seuence
<220> FEATURE:
<223> OTHER INFORMATION: Reverse transcriptase variant O1+K3
       (T55G+D524A) nucleic acid sequence

<400> SEQUENCE: 18

```
atgaccctaa atatagaaga tgagcatcgg ctacatgaga cctcaaaaga gccagatgtt     60
tctctagggt ccacatggct gtctgatttt cctcaggcct gggcggaaac cggggggcatg    120 ggactggcag ttcgccaagc tcctctgatc ataccttga  agcaggttc  tacccccgtg    180 tccataaaac aatacccat  gtcacaagaa gccagactgg ggatcaagcc cacatacag     240 agactgttgg accagggaat actggtaccc tgccagtccc cctggaacac gcccctgcta    300
cccgttaaga aaccagggac taatgattat aggcctgtcc aggatctgag agaagtcaac    360
```

```
aagcgggtgg aagacatcca ccccaccgtg cccaacccct tcaacctctt gagcgggctc    420
ccaccgtccc accagtggta cactgtgctt gatttaaagg atgcctttt  ctgcctgaga    480 ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaaagaggg tcagagatgg    840
ctgactgagg ccagaaaaga gactgtgatg gggcagccta ctccgaagac ccctcgacaa    900
ctaagggagt tcctagggac ggcaggcttc tgtcgcctct ggatccctgg gtttgcagaa    960
atggcagccc ccttgtaccc tctcaccaaa acggggactc tgtttaattg gggcccagac   1020
caacaaaagg cctatcaaga aatcaagcaa gctcttctaa ctgccccagc cctggggttg   1080
ccagatttga ctaagcccct tgaactcttt gtcgacgaga agcagggcta cgccaaaggt   1140
gtcctaacgc aaaaactggg accttggcgt cggccggtgg cctacctgtc caaaaagcta   1200
gacccagtag cagctgggtg gccccctgc  ctacggatgg tagcagccat tgccgtactg   1260
acaaaggatg caggcaagct aaccatggga cagccactag tcattctggc ccccatgca    1320 gtagaggcac tagtcaaaca ccccccgac  cgctggcttt ccaacgcccg gatgactcac   1380
tatcaggcct gcttttgga  cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggctggaag cagtctctta aagagggac  agcgtaaggc gggagctgcg   1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca gcgccgaggc tagaggcaac cggatggctg accaagcggc ccgaaaggca   1980
gccatcacag agactccaga cacctctacc ctcctcata                           2019

<210> SEQ ID NO 19
<211> LENGTH: 2019
<212> TYPE: DNA
<213> ORGANISM: Artificial Seuence
<220> FEATURE:
<223> OTHER INFORMATION: Reverse transcriptase variant O1+K2
      (T55G+D524N) nucleic acid sequence

<400> SEQUENCE: 19
atgaccctaa atatagaaga tgagcatcgg ctacatgaga cctcaaaaga gccagatgtt     60
tctctagggt ccacatggct gtctgatttt cctcaggcct gggcggaaac cgggggcatg    120
ggactggcag ttcgccaagc tcctctgatc ataccttga  aagcaggttc taccccgtg     180 tccataaaac aataccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
```

```
aagcgggtgg aagacatcca ccccaccgtg cccaacccctt acaacctctt gagcgggctc    420
ccaccgtccc accagtggta cactgtgctt gatttaaagg atgccttttt ctgcctgaga    480
ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaaagaggg tcagagatgg    840
ctgactgagg ccagaaaaga gactgtgatg gggcagccta ctccgaagac ccctcgacaa    900
ctaagggagt tcctagggac ggcaggcttc tgtcgcctct ggatccctgg gtttgcagaa    960
atggcagccc ccttgtaccc tctcaccaaa acggggactc tgtttaattg gggcccagac   1020
caacaaaagg cctatcaaga aatcaagcaa gctcttctaa ctgccccagc cctgggggttg   1080 ccagatttga ctaagcccctt tgaactcttt gtcgacgaga agcagggcta cgccaaaggt   1140
gtcctaacgc aaaaactggg accttggcgt cggccggtgg cctacctgtc caaaaagcta   1200
gacccagtag cagctgggtg gccccccttgc ctacggatgg tagcagccat tgccgtactg   1260
acaaaggatg caggcaagct aaccatggga cagccactag tcattctggc cccccatgca   1320
gtagaggcac tagtcaaaca ccccccgac cgctggcttt ccaacgcccg gatgactcac   1380
tatcaggcct gcttttggga cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cgaacggaag cagtctctta aagagggac agcgtaaggc gggagctgcg   1620
gtgaccaccg agaccgaggt aatctgggct aaagcccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca cgcgccgaggc tagaggcaac cggatggctg accaagcggc ccgaaaggca   1980
gccatcacag agactccaga cacctctacc ctcctcata                           2019

<210> SEQ ID NO 20
<211> LENGTH: 2019
<212> TYPE: DNA
<213> ORGANISM: Artificial Seuence
<220> FEATURE:
<223> OTHER INFORMATION: Reverse transcriptase variant O1+LT
      (T55G+H204R+M289L+T306K+F309N) nucleic acid sequence

<400> SEQUENCE: 20
atgaccctaa atatagaaga tgagcatcgg ctacatgaga cctcaaaaga gccagatgtt     60
tctctagggt ccacatggct gtctgatttt cctcaggcct gggcggaaac cgggggcatg    120
ggactggcag ttcgccaagc tcctctgatc atacctctga aagcaggttc tacccccgtg    180
tccataaaac aatacccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
```

| | |
|---|---|
| aagcgggtgg aagacatcca ccccaccgtg cccaacccct acaacctctt gagcgggctc | 420 |
| ccaccgtccc accagtggta cactgtgctt gatttaaagg atgcctttt ctgcctgaga | 480 |
| ctccacccca ccagtcagcc tctcttcgcc tttgagtgga gagatccaga gatgggaatc | 540 |
| tcaggacaat tgacctggac cagactccca cagggtttca aaaacagtcc caccctgttt | 600 |
| gatgaggcac tgcgcagaga cctagcagac ttccggatcc agcacccaga cttgatcctg | 660 |
| ctacagtacg tggatgactt actgctggcc gccacttctg agctagactg ccaacaaggt | 720 |
| actcgggccc tgttacaaac cctagggaac ctcgggtatc gggcctcggc caagaaagcc | 780 |
| caaatttgcc agaaacaggt caagtatctg gggtatcttc taaaagaggg tcagagatgg | 840 |
| ctgactgagg ccagaaaaga gactgtgctg gggcagccta ctccgaagac ccctcgacaa | 900 |
| ctaagggagt tcctagggaa agcaggcaac tgtcgcctct ggatccctgg gtttgcagaa | 960 |
| atggcagccc ccttgtaccc tctcaccaaa acggggactc tgtttaattg gggcccagac | 1020 |
| caacaaaagg cctatcaaga aatcaagcaa gctcttctaa ctgccccagc cctggggttg | 1080 |
| ccagatttga ctaagccctt tgaactcttt gtcgacgaga agcagggcta cgccaaaggt | 1140 |
| gtcctaacgc aaaaactggg accttggcgt cggccggtgg cctacctgtc caaaaagcta | 1200 |
| gacccagtag cagctgggtg gccccccttgc ctacggatgg tagcagccat tgccgtactg | 1260 |
| acaaaggatg caggcaagct aaccatggga cagccactag tcattctggc cccccatgca | 1320 |
| gtagaggcac tagtcaaaca accccccgac cgctggcttt ccaacgcccg gatgactcac | 1380 |
| tatcaggcct gcttttgga cacggaccgg gtccagttcg gaccggtggt agccctgaac | 1440 |
| ccggctacgc tgctcccact gcctgaggaa gggctgcaac acaactgcct tgatatcctg | 1500 |
| gccgaagccc acggaacccg acccgaccta acggaccagc cgctcccaga cgccgaccac | 1560 |
| acctggtaca cggatggaag cagtctctta aagagggac agcgtaaggc gggagctgcg | 1620 |
| gtgaccaccg agaccgaggt aatctgggct aaagccctgc cagccgggac atccgctcag | 1680 |
| cgggctgaac tgatagcact cacccaggcc ctaaagatgg cagaaggtaa gaagctaaat | 1740 |
| gtttatactg atagccgtta tgcttttgct actgcccata tccatggaga aatatacaga | 1800 |
| aggcgtgggt tgctcacatc agaaggcaaa gagatcaaaa ataaagacga gatcttggcc | 1860 |
| ctactaaaag ccctctttct gcccaaaaga cttagcataa tccattgtcc aggacatcaa | 1920 |
| aagggacaca cgcgccgaggc tagaggcaac cggatggctg accaagcggc ccgaaaggca | 1980 |
| gccatcacag agactccaga cacctctacc ctcctcata | 2019 |

<210> SEQ ID NO 21
<211> LENGTH: 673
<212> TYPE: PRT
<213> ORGANISM: Artificial Seuence
<220> FEATURE:
<223> OTHER INFORMATION: Reverse transcriptase variant O2(T55A) amino acid sequence

<400> SEQUENCE: 21

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Ala Ser Thr Pro Val Ser Ile Lys Gln
    50                  55                  60

```
Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
                 85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
```

```
                        485                 490                 495
Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile

<210> SEQ ID NO 22
<211> LENGTH: 673
<212> TYPE: PRT
<213> ORGANISM: Artificial Seuence
<220> FEATURE:
<223> OTHER INFORMATION: Reverse transcriptase variant O3(T55S) amino
      acid sequence

<400> SEQUENCE: 22

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Ser Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
```

```
            165                 170                 175
Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
            210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
            290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
            325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
            370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
            580                 585                 590
```

His Ile His Gly Glu Ile Tyr Arg Arg Gly Leu Leu Thr Ser Glu
            595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
        660                 665                 670

Ile

<210> SEQ ID NO 23
<211> LENGTH: 673
<212> TYPE: PRT
<213> ORGANISM: Artificial Seuence
<220> FEATURE:
<223> OTHER INFORMATION: Reverse transcriptase variant P13(T55K) amino
      acid sequence

<400> SEQUENCE: 23

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Lys Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
            85                  90                  95

Thr Pro Leu Leu Pro Val Lys Lys Pro Gly Thr Asn Asp Tyr Arg Pro
        100                 105                 110

Val Gln Asp Leu Arg Glu Val Asn Lys Arg Val Glu Asp Ile His Pro
    115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
            165                 170                 175

Glu Met Gly Ile Ser Gly Gln Leu Thr Trp Thr Arg Leu Pro Gln Gly
        180                 185                 190

Phe Lys Asn Ser Pro Thr Leu Phe Asp Glu Ala Leu His Arg Asp Leu
    195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
        260                 265                 270

-continued

```
Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile
```

```
<210> SEQ ID NO 24
<211> LENGTH: 2019
<212> TYPE: DNA
<213> ORGANISM: Artificial Seuence
<220> FEATURE:
<223> OTHER INFORMATION: Reverse transcriptase variant O2(T55A) nucleic
      acid sequence

<400> SEQUENCE: 24
```

| | | | | | |
|---|---|---|---|---|---|
| atgaccctaa | atatagaaga | tgagcatcgg | ctacatgaga | cctcaaaaga | gccagatgtt | 60 |
| tctctagggt | ccacatggct | gtctgatttt | cctcaggcct | gggcggaaac | cggggggcatg | 120 |
| ggactggcag | ttcgccaagc | tcctctgatc | atacctctga | aagcagcttc | taccccgtg | 180 |
| tccataaaac | aatacccat | gtcacaagaa | gccagactgg | ggatcaagcc | ccacatacag | 240 |
| agactgttgg | accagggaat | actggtaccc | tgccagtccc | cctggaacac | gccctgcta | 300 |
| cccgttaaga | aaccagggac | taatgattat | aggcctgtcc | aggatctgag | agaagtcaac | 360 |
| aagcgggtgg | aagacatcca | ccccaccgtg | cccaaccctt | acaacctctt | gagcgggctc | 420 |
| ccaccgtccc | accagtggta | cactgtgctt | gatttaaagg | atgcttttt | ctgcctgaga | 480 |
| ctccacccca | ccagtcagcc | tctcttcgcc | tttgagtgga | gagatccaga | gatgggaatc | 540 |
| tcaggacaat | tgacctggac | cagactccca | cagggtttca | aaaacagtcc | caccctgttt | 600 |
| gatgaggcac | tgcacagaga | cctagcagac | ttccggatcc | agcacccaga | cttgatcctg | 660 |
| ctacagtacg | tggatgactt | actgctggcc | gccacttctg | agctagactg | ccaacaaggt | 720 |
| actcgggccc | tgttacaaac | cctagggaac | ctcgggtatc | gggcctcggc | caagaaagcc | 780 |
| caaatttgcc | agaaacaggt | caagtatctg | gggtatcttc | taaaagaggg | tcagagatgg | 840 |
| ctgactgagg | ccagaaaaga | gactgtgatg | gggcagccta | ctccgaagac | ccctcgacaa | 900 |
| ctaagggagt | tcctagggac | ggcaggcttc | tgtcgcctct | ggatccctgg | gtttgcagaa | 960 |
| atggcagccc | ccttgtaccc | tctcaccaaa | acggggactc | tgtttaattg | ggcccagac | 1020 |
| caacaaaagg | cctatcaaga | aatcaagcaa | gctcttctaa | ctgccccagc | cctggggttg | 1080 |
| ccagatttga | ctaagccctt | tgaactcttt | gtcgacgaga | agcagggcta | cgccaaaggt | 1140 |
| gtcctaacgc | aaaaactggg | accttggcgt | cggccggtgg | cctacctgtc | caaaaagcta | 1200 |
| gacccagtag | cagctgggtg | gccccttgc | ctacggatgg | tagcagccat | tgccgtactg | 1260 |
| acaaaggatg | caggcaagct | aaccatggga | cagccactag | tcattctggc | ccccatgca | 1320 |
| gtagaggcac | tagtcaaaca | accccccgac | cgctggcttt | ccaacgcccg | gatgactcac | 1380 |
| tatcaggcct | tgcttttgga | cacggaccgg | gtccagttcg | gaccggtggt | agccctgaac | 1440 |
| ccggctacgc | tgctcccact | gcctgaggaa | gggctgcaac | acaactgcct | tgatatcctg | 1500 |
| gccgaagccc | acggaaccg | acccgaccta | acggaccagc | cgctcccaga | cgccgaccac | 1560 |
| acctggtaca | cggatggaag | cagtctctta | caagagggac | agcgtaaggc | gggagctgcg | 1620 |
| gtgaccaccg | agaccgaggt | aatctgggct | aaagccctgc | cagccgggac | atccgctcag | 1680 |
| cgggctgaac | tgatagcact | cacccaggcc | ctaaagatgg | cagaaggtaa | gaagctaaat | 1740 |
| gtttatactg | atagccgtta | tgcttttgct | actgcccata | tccatggaga | aatatacaga | 1800 |
| aggcgtgggt | tgctcacatc | agaaggcaaa | gagatcaaaa | ataaagacga | gatcttggcc | 1860 |
| ctactaaaag | ccctctttct | gcccaaaaga | cttagcataa | tccattgtcc | aggacatcaa | 1920 |
| aagggacaca | gcgccgaggc | tagaggcaac | cggatggctg | accaagcggc | ccgaaaggca | 1980 |
| gccatcacag | agactccaga | cacctctacc | ctcctcata | | | 2019 |

<210> SEQ ID NO 25
<211> LENGTH: 2019
<212> TYPE: DNA
<213> ORGANISM: Artificial Seuence
<220> FEATURE:
<223> OTHER INFORMATION: Reverse transcriptase variant O3(T55S) nucleic acid sequence

<400> SEQUENCE: 25

```
atgaccctaa atatagaaga tgagcatcgg ctacatgaga cctcaaaaga gccagatgtt      60
tctctagggt ccacatggct gtctgatttt cctcaggcct gggcggaaac cgggggcatg     120
ggactggcag ttcgccaagc tcctctgatc atacctctga agcatcttc taccccgtg      180
tccataaaac aatacccat gtcacaagaa gccagactgg ggatcaagcc ccacatacag     240
agactgttgg accagggaat actggtaccc tgccagtccc cctggaacac gcccctgcta     300
cccgttaaga accagggac taatgattat aggcctgtcc aggatctgag agaagtcaac     360
aagcgggtgg aagacatcca ccccaccgtg cccaaccctt acaacctctt gagcgggctc     420
ccaccgtccc accagtggta cactgtgctt gatttaaagg atgccttttt ctgcctgaga     480
ctccaccca ccagtcagcc tctcttcgcc tttgagtgga gagatccaga tgggaatc      540
tcaggacaat tgacctggac cagactccca cagggtttca aaaacagtcc caccctgttt     600
gatgaggcac tgcacagaga cctagcagac ttccggatcc agcacccaga cttgatcctg     660
ctacagtacg tggatgactt actgctggcc gccacttctg agctagactg ccaacaaggt     720
actcgggccc tgttacaaac cctagggaac ctcgggtatc gggcctcggc caagaaagcc     780
caaatttgcc agaaacaggt caagtatctg gggtatcttc taaaagaggg tcagagatgg     840
ctgactgagg ccagaaaaga gactgtgatg gggcagccta ctccgaagac ccctcgacaa     900
ctaagggagt cctagggac ggcaggcttc tgtcgcctct ggatccctgg gtttgcagaa     960
atggcagccc ccttgtaccc tctcaccaaa acggggactc tgtttaattg gggcccagac    1020
caacaaaagg cctatcaaga aatcaagcaa gctcttctaa ctgccccagc cctgggttg     1080
ccagatttga ctaagcccctt tgaactcttt gtcgacgaga agcagggcta cgccaaaggt    1140
gtcctaacgc aaaaactggg accttggcgt cggccggtgg cctacctgtc caaaaagcta    1200
gacccagtag cagctgggtg gccccccttgc ctacggatgg tagcagccat tgccgtactg    1260
acaaaggatg caggcaagct aaccatggga cagccactag tcattctggc cccccatgca    1320
gtagaggcac tagtcaaaca accccccgac cgctggcttt ccaacgcccg gatgactcac    1380
tatcaggcct tgcttttgga cacggaccgg gtccagttcg accggtggt agccctgaac    1440
ccggctacgc tgctcccact gcctgaggaa gggctgcaac acaactgcct tgatatcctg    1500
gccgaagccc acggaacccg acccgaccta acggaccagc cgctcccaga cgccgaccac    1560
acctggtaca cggatggaag cagtctctta caagagggac agcgtaaggc gggagctgcg    1620
gtgaccaccg agaccgaggt aatctgggct aaagccctgc cagccgggac atccgctcag    1680
cgggctgaac tgatagcact cacccaggcc ctaaagatgg cagaaggtaa gaagctaaat    1740
gtttatactg atagccgtta tgcttttgct actgcccata tccatggaga aatatacaga    1800
aggcgtgggt tgctcacatc agaaggcaaa gagatcaaaa ataaagacga gatcttggcc    1860
ctactaaaag ccctctttct gcccaaaaga cttagcataa tccattgtcc aggacatcaa    1920
aagggacaca gcgccgaggc tagaggcaac cggatggctg accaagcggc ccgaaaggca    1980
gccatcacag agactccaga cacctctacc ctcctcata                           2019
```

<210> SEQ ID NO 26
<211> LENGTH: 2019
<212> TYPE: DNA
<213> ORGANISM: Artificial Seuence
<220> FEATURE:
<223> OTHER INFORMATION: Reverse transcriptase variant P13(T55K) nucleic acid sequence

<400> SEQUENCE: 26

```
atgaccctaa atatagaaga tgagcatcgg ctacatgaga cctcaaaaga gccagatgtt      60
tctctagggt ccacatggct gtctgatttt cctcaggcct gggcggaaac cggggggcatg    120
ggactggcag ttcgccaagc tcctctgatc atacctctga agcaaaaatc taccccgtg      180
tccataaaac aataccccat gtcacaagaa gccagactgg ggatcaagcc ccacatacag     240
agactgttgg accagggaat actggtaccc tgccagtccc cctggaacac gcccctgcta    300
cccgttaaga aaccagggac taatgattat aggcctgtcc aggatctgag agaagtcaac    360
aagcgggtgg aagacatcca ccccaccgtg cccaaccctt acaacctctt gagcgggctc    420
ccaccgtccc accagtggta cactgtgctt gatttaaagg atgcctttt ctgcctgaga     480
ctccacccca ccagtcagcc tctcttcgcc tttgagtgga gagatccaga tgggaatc      540
tcaggacaat tgacctggac cagactccca cagggtttca aaaacagtcc caccctgttt   600
gatgaggcac tgcacagaga cctagcagac ttccggatcc agcacccaga cttgatcctg   660
ctacagtacg tggatgactt actgctggcc gccacttctg agctagactg ccaacaaggt   720
actcgggccc tgttacaaac cctagggaac ctcgggtatc gggcctcggc caagaaagcc  780
caaatttgcc agaaacaggt caagtatctg gggtatcttc taaaagaggg tcagagatgg  840
ctgactgagg ccagaaaaga ctgtgatg gggcagccta ctccgaagac ccctcgacaa     900
ctaagggagt cctagggac ggcaggcttc tgtcgcctct ggatccctgg gtttgcagaa    960
atggcagccc ccttgtaccc tctcaccaaa acggggactc tgtttaattg gggcccagac  1020
caacaaaagg cctatcaaga aatcaagcaa gctcttctaa ctgccccagc cctgggggttg 1080
ccagatttga ctaagcccctt tgaactcttt gtcgacgaga agcagggcta cgccaaaggt  1140
gtcctaacgc aaaaactggg accttggcgt cggccggtgg cctacctgtc caaaaagcta  1200
gacccagtag cagctgggtg gccccctggc ctacggatgg tagcagccat tgccgtactg 1260
acaaaggatg caggcaagct aaccatggga cagccactag tcattctggc cccccatgca 1320
gtagaggcac tagtcaaaca accccccgac cgctggcttt ccaacgcccg gatgactcac 1380
tatcaggcct tgcttttgga cacggaccgg gtccagttcg gaccggtggt agccctgaac 1440
ccggctacgc tgctcccact gcctgaggaa gggctgcaac acaactgcct tgatatcctg 1500
gccgaagccc acggaacccg acccgaccta acggaccagc cgctcccaga cgccgaccac 1560
acctggtaca cggatggaag cagtctctta caagagggac agcgtaaggc gggagctgcg 1620
gtgaccaccg agaccgaggt aatctgggct aaagccctgc cagccgggac atccgctcag 1680
cgggctgaac tgatagcact cacccaggcc ctaaagatgg cagaaggtaa gaagctaaat 1740
gtttatactg atagccgtta tgcttttgct actgcccata tccatggaga aatatacaga 1800
aggcgtgggt tgctcacatc agaaggcaaa gagatcaaaa ataaagacga gatcttggcc 1860
ctactaaaag ccctctttct gcccaaaaga cttagcataa tccattgtcc aggacatcaa 1920
aagggacaca gcgccgaggc tagaggcaac cggatggctg accaagcggc ccgaaaggca 1980
gccatcacag agactccaga cacctctacc ctcctcata                         2019
```

<210> SEQ ID NO 27
<211> LENGTH: 673
<212> TYPE: PRT
<213> ORGANISM: Artificial Seuence
<220> FEATURE:
<223> OTHER INFORMATION: Reverse transcriptase variant D1(T287K) amino acid sequence

<400> SEQUENCE: 27

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Lys
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365
```

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Arg Gly Leu Leu Thr Ser Glu
            595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile

<210> SEQ ID NO 28
<211> LENGTH: 673
<212> TYPE: PRT
<213> ORGANISM: Artificial Seuence
<220> FEATURE:
<223> OTHER INFORMATION: Reverse transcriptase variant K1(Q291K) amino
      acid sequence

<400> SEQUENCE: 28

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

-continued

```
Leu Ile Ile Pro Leu Lys Ala Thr Ser Thr Pro Val Ser Ile Lys Gln
 50                  55                  60

Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
                 85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
                115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
                210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Lys Pro Thr Pro Lys Thr Pro Arg Gln Leu Arg Glu Phe
                290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
                370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
```

```
              465                 470                 475                 480
    Pro Ala Thr Leu Leu Pro Leu Pro Glu Glu Gly Leu Gln His Asn Cys
                    485                 490                 495

Leu Asp Ile Leu Ala Glu Ala His Gly Thr Arg Pro Asp Leu Thr Asp
                    500                 505                 510

Gln Pro Leu Pro Asp Ala Asp His Thr Trp Tyr Thr Asp Gly Ser Ser
                    515                 520                 525

Leu Leu Gln Glu Gly Gln Arg Lys Ala Gly Ala Val Thr Thr Glu
                530                 535                 540

Thr Glu Val Ile Trp Ala Lys Ala Leu Pro Ala Gly Thr Ser Ala Gln
    545                 550                 555                 560

Arg Ala Glu Leu Ile Ala Leu Thr Gln Ala Leu Lys Met Ala Glu Gly
                    565                 570                 575

Lys Lys Leu Asn Val Tyr Thr Asp Ser Arg Tyr Ala Phe Ala Thr Ala
                    580                 585                 590

His Ile His Gly Glu Ile Tyr Arg Arg Arg Gly Leu Leu Thr Ser Glu
                    595                 600                 605

Gly Lys Glu Ile Lys Asn Lys Asp Glu Ile Leu Ala Leu Leu Lys Ala
                    610                 615                 620

Leu Phe Leu Pro Lys Arg Leu Ser Ile Ile His Cys Pro Gly His Gln
    625                 630                 635                 640

Lys Gly His Ser Ala Glu Ala Arg Gly Asn Arg Met Ala Asp Gln Ala
                    645                 650                 655

Ala Arg Lys Ala Ala Ile Thr Glu Thr Pro Asp Thr Ser Thr Leu Leu
                    660                 665                 670

Ile

<210> SEQ ID NO 29
<211> LENGTH: 673
<212> TYPE: PRT
<213> ORGANISM: Artificial Seuence
<220> FEATURE:
<223> OTHER INFORMATION: Reverse transcriptase variant K4(T306K) amino
      acid sequence

<400> SEQUENCE: 29

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
```

-continued

```
            145                 150                 155                 160
        Leu His Pro Thr Ser Gln Pro Leu Phe Ala Phe Glu Trp Arg Asp Pro
                        165                 170                 175
        Glu Met Gly Ile Ser Gly Gln Leu Thr Trp Thr Arg Leu Pro Gln Gly
                        180                 185                 190
        Phe Lys Asn Ser Pro Thr Leu Phe Asp Glu Ala Leu His Arg Asp Leu
                        195                 200                 205
        Ala Asp Phe Arg Ile Gln His Pro Asp Leu Ile Leu Leu Gln Tyr Val
                        210                 215                 220
        Asp Asp Leu Leu Leu Ala Ala Thr Ser Glu Leu Asp Cys Gln Gln Gly
        225                 230                 235                 240
        Thr Arg Ala Leu Leu Gln Thr Leu Gly Asn Leu Gly Tyr Arg Ala Ser
                        245                 250                 255
        Ala Lys Lys Ala Gln Ile Cys Gln Lys Gln Val Lys Tyr Leu Gly Tyr
                        260                 265                 270
        Leu Leu Lys Glu Gly Gln Arg Trp Leu Thr Glu Ala Arg Lys Glu Thr
                        275                 280                 285
        Val Met Gly Gln Pro Thr Pro Lys Thr Pro Arg Gln Leu Arg Glu Phe
                        290                 295                 300
        Leu Gly Lys Ala Gly Phe Cys Arg Leu Trp Ile Pro Gly Phe Ala Glu
        305                 310                 315                 320
        Met Ala Ala Pro Leu Tyr Pro Leu Thr Lys Thr Gly Thr Leu Phe Asn
                        325                 330                 335
        Trp Gly Pro Asp Gln Gln Lys Ala Tyr Gln Glu Ile Lys Gln Ala Leu
                        340                 345                 350
        Leu Thr Ala Pro Ala Leu Gly Leu Pro Asp Leu Thr Lys Pro Phe Glu
                        355                 360                 365
        Leu Phe Val Asp Glu Lys Gln Gly Tyr Ala Lys Gly Val Leu Thr Gln
                        370                 375                 380
        Lys Leu Gly Pro Trp Arg Arg Pro Val Ala Tyr Leu Ser Lys Lys Leu
        385                 390                 395                 400
        Asp Pro Val Ala Ala Gly Trp Pro Pro Cys Leu Arg Met Val Ala Ala
                        405                 410                 415
        Ile Ala Val Leu Thr Lys Asp Ala Gly Lys Leu Thr Met Gly Gln Pro
                        420                 425                 430
        Leu Val Ile Leu Ala Pro His Ala Val Glu Ala Leu Val Lys Gln Pro
                        435                 440                 445
        Pro Asp Arg Trp Leu Ser Asn Ala Arg Met Thr His Tyr Gln Ala Leu
        450                 455                 460
        Leu Leu Asp Thr Asp Arg Val Gln Phe Gly Pro Val Val Ala Leu Asn
        465                 470                 475                 480
        Pro Ala Thr Leu Leu Pro Leu Pro Glu Glu Gly Leu Gln His Asn Cys
                        485                 490                 495
        Leu Asp Ile Leu Ala Glu Ala His Gly Thr Arg Pro Asp Leu Thr Asp
                        500                 505                 510
        Gln Pro Leu Pro Asp Ala Asp His Thr Trp Tyr Thr Asp Gly Ser Ser
                        515                 520                 525
        Leu Leu Gln Glu Gly Gln Arg Lys Ala Gly Ala Ala Val Thr Thr Glu
                        530                 535                 540
        Thr Glu Val Ile Trp Ala Lys Ala Leu Pro Ala Gly Thr Ser Ala Gln
        545                 550                 555                 560
        Arg Ala Glu Leu Ile Ala Leu Thr Gln Ala Leu Lys Met Ala Glu Gly
                        565                 570                 575
```

```
Lys Lys Leu Asn Val Tyr Thr Asp Ser Arg Tyr Ala Phe Ala Thr Ala
            580                 585                 590

His Ile His Gly Glu Ile Tyr Arg Arg Gly Leu Leu Thr Ser Glu
            595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                    645                 650                 655

Ala Arg Lys Ala Ala Ile Thr Glu Thr Pro Asp Thr Ser Thr Leu Leu
            660                 665                 670

Ile

<210> SEQ ID NO 30
<211> LENGTH: 673
<212> TYPE: PRT
<213> ORGANISM: Artificial Seuence
<220> FEATURE:
<223> OTHER INFORMATION: Reverse transcriptase variant K3(D524A) amino
      acid sequence

<400> SEQUENCE: 30

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
            50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                    85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
            130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                    165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
            210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                    245                 250                 255
```

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
            290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
            325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
            370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Ala Gly Ser Ser
            515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Leu Leu Thr Ser Glu
            595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
            660                 665                 670

Ile

<210> SEQ ID NO 31
<211> LENGTH: 673
<212> TYPE: PRT
<213> ORGANISM: Artificial Seuence
<220> FEATURE:
<223> OTHER INFORMATION: Reverse transcriptase variant K2(D524N) amino
      acid sequence

<400> SEQUENCE: 31

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350
```

```
Leu Thr Ala Pro Ala Leu Gly Leu Pro Asp Leu Thr Lys Pro Phe Glu
            355                 360                 365
Leu Phe Val Asp Glu Lys Gln Gly Tyr Ala Lys Gly Val Leu Thr Gln
370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
            420                 425                 430
Leu Val Ile Leu Ala Pro His Ala Val Glu Ala Leu Val Lys Gln Pro
            435                 440                 445
Pro Asp Arg Trp Leu Ser Asn Ala Arg Met Thr His Tyr Gln Ala Leu
            450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
            500                 505                 510
Gln Pro Leu Pro Asp Ala Asp His Thr Trp Tyr Thr Asn Gly Ser Ser
            515                 520                 525
Leu Leu Gln Glu Gly Gln Arg Lys Ala Gly Ala Ala Val Thr Thr Glu
            530                 535                 540
Thr Glu Val Ile Trp Ala Lys Ala Leu Pro Ala Gly Thr Ser Ala Gln
545                 550                 555                 560
Arg Ala Glu Leu Ile Ala Leu Thr Gln Ala Leu Lys Met Ala Glu Gly
                565                 570                 575
Lys Lys Leu Asn Val Tyr Thr Asp Ser Arg Tyr Ala Phe Ala Thr Ala
            580                 585                 590
His Ile His Gly Glu Ile Tyr Arg Arg Arg Gly Leu Leu Thr Ser Glu
            595                 600                 605
Gly Lys Glu Ile Lys Asn Lys Asp Glu Ile Leu Ala Leu Leu Lys Ala
610                 615                 620
Leu Phe Leu Pro Lys Arg Leu Ser Ile Ile His Cys Pro Gly His Gln
625                 630                 635                 640
Lys Gly His Ser Ala Glu Ala Arg Gly Asn Arg Met Ala Asp Gln Ala
                645                 650                 655
Ala Arg Lys Ala Ala Ile Thr Glu Thr Pro Asp Thr Ser Thr Leu Leu
            660                 665                 670
Ile
```

<210> SEQ ID NO 32
<211> LENGTH: 673
<212> TYPE: PRT
<213> ORGANISM: Artificial Seuence
<220> FEATURE:
<223> OTHER INFORMATION: Reverse transcriptase variant
      LT(H204R+M289L+T306K+F309N) amino acid sequence

<400> SEQUENCE: 32

```
Met Thr Leu Asn Ile Glu Asp Glu His Arg Leu His Glu Thr Ser Lys
1               5                   10                  15
Glu Pro Asp Val Ser Leu Gly Ser Thr Trp Leu Ser Asp Phe Pro Gln
            20                  25                  30
```

-continued

```
Ala Trp Ala Glu Thr Gly Gly Met Gly Leu Ala Val Arg Gln Ala Pro
         35                  40                  45

Leu Ile Ile Pro Leu Lys Ala Thr Ser Thr Pro Val Ser Ile Lys Gln
 50                  55                  60

Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
                 85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu Arg Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Leu Gly Gln Pro Thr Pro Lys Thr Pro Arg Gln Leu Arg Glu Phe
    290                 295                 300

Leu Gly Lys Ala Gly Asn Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
```

```
                450             455             460
Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
            610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670
Ile

<210> SEQ ID NO 33
<211> LENGTH: 2019
<212> TYPE: DNA
<213> ORGANISM: Artificial Seuence
<220> FEATURE:
<223> OTHER INFORMATION: Reverse transcriptase variant D1(T287K) nucleic
      acid sequence

<400> SEQUENCE: 33
atgaccctaa atatagaaga tgagcatcgg ctacatgaga cctcaaaaga gccagatgtt      60
tctctagggt ccacatggct gtctgatttt cctcaggcct gggcggaaac cggggggcatg    120 ggactggcag ttcgccaagc tcctctgatc atacctctga agcaacctc tacccccgtg     180 tccataaaac aataccccat gtcacaagaa gccagactgg ggatcaagcc ccacatacag     240
agactgttgg accagggaat actggtaccc tgccagtccc cctggaacac gcccctgcta     300
cccgttaaga aaccagggac taatgattat aggcctgtcc aggatctgag agaagtcaac     360
aagcgggtgg aagacatcca ccccaccgtg cccaaccctt acaacctctt gagcgggctc     420
ccaccgtccc accagtggta cactgtgctt gatttaaagg atgccttttt ctgcctgaga     480
ctccacccca ccagtcagcc tctcttcgcc tttgagtgga gagatccaga gatgggaatc     540
tcaggacaat tgacctggac cagactccca cagggtttca aaacagtcc caccctgttt     600 gatgaggcac tgcacagaga cctagcagac ttcggatcc agcacccaga cttgatcctg     660
ctacagtacg tggatgactt actgctggcc gccacttctg agctagactg ccaacaaggt     720
actcgggccc tgttacaaac cctagggaac ctcgggtatc gggcctcggc caagaaagcc     780
```

```
caaatttgcc agaaacaggt caagtatctg gggtatcttc taaaagaggg tcagagatgg    840
ctgactgagg ccagaaaaga gaaagtgatg gggcagccta ctccgaagac ccctcgacaa    900
ctaagggagt tcctagggac ggcaggcttc tgtcgcctct ggatccctgg gtttgcagaa    960
atggcagccc ccttgtaccc tctcaccaaa acggggactg tgtttaattg gggcccagac   1020
caacaaaagg cctatcaaga aatcaagcaa gctcttctaa ctgccccagc cctggggttg   1080
ccagatttga ctaagccctt tgaactcttt gtcgacgaga agcagggcta cgccaaaggt   1140
gtcctaacgc aaaaactggg accttggcgt cggccggtgg cctacctgtc aaaaagcta   1200 gacccagtag cagctgggtg gccccttgc ctacggatgg tagcagccat tgccgtactg   1260
acaaaggatg caggcaagct aaccatggga cagccactag tcattctggc cccccatgca   1320
gtagaggcac tagtcaaaca ccccccgac cgctggcttt ccaacgcccg gatgactcac   1380
tatcaggcct tgcttttgga cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggatggaag cagtctctta caagagggac agcgtaaggc gggagctgcg   1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca gcgccgaggc tagaggcaac cggatggctg accaagcggc ccgaaaggca   1980
gccatcacag agactccaga cacctctacc ctcctcata                          2019
```

<210> SEQ ID NO 34
<211> LENGTH: 2019
<212> TYPE: DNA
<213> ORGANISM: Artificial Seuence
<220> FEATURE:
<223> OTHER INFORMATION: Reverse transcriptase variant K1(Q291K) nucleic
      acid sequence

<400> SEQUENCE: 34

```
atgaccctaa atatagaaga tgagcatcgg ctacatgaga cctcaaaaga gccagatgtt     60
tctctagggt ccacatggct gtctgatttt cctcaggcct gggcggaaac cgggggcatg    120
ggactggcag ttcgccaagc tcctctgatc atacctctga agcaacctc taccccgtg    180 tccataaaac aataccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
aagcgggtgg aagacatcca ccccaccgtg cccaacccctt acaacctctt gagcgggctc    420
ccaccgtccc accagtggta cactgtgctt gatttaaagg atgcctttt ctgcctgaga    480 ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttcggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
```

```
caaatttgcc agaaacaggt caagtatctg gggtatcttc taaaagaggg tcagagatgg      840
ctgactgagg ccagaaaaga gactgtgatg gggaaaccta ctccgaagac ccctcgacaa      900
ctaagggagt tcctagggac ggcaggcttc tgtcgcctct ggatccctgg gtttgcagaa      960
atggcagccc ccttgtaccc tctcaccaaa acggggactg tgtttaattg gggcccagac     1020
caacaaaagg cctatcaaga aatcaagcaa gctcttctaa ctgccccagc cctggggttg     1080
ccagatttga ctaagccctt tgaactcttt gtcgacgaga agcagggcta cgccaaaggt     1140
gtcctaacgc aaaaactggg accttggcgt cggccggtgg cctacctgtc aaaaagcta     1200 gacccagtag cagctgggtg ccccccttgc ctacggatgg tagcagccat tgccgtactg     1260
acaaaggatg caggcaagct aaccatggga cagccactag tcattctggc ccccatgca     1320 gtagaggcac tagtcaaaca ccccccgac cgctggcttt ccaacgcccg gatgactcac     1380
tatcaggcct tgcttttgga cacggaccgg gtccagttcg gaccggtggt agccctgaac     1440
ccggctacgc tgctcccact gcctgaggaa gggctgcaac acaactgcct tgatatcctg     1500
gccgaagccc acggaacccg acccgaccta acggaccagc cgctcccaga cgccgaccac     1560
acctggtaca cggatggaag cagtctctta aagagggaca agcgtaaggc gggagctgcg     1620
gtgaccaccg agaccgaggt aatctgggct aaagccctgc cagccgggac atccgctcag     1680
cgggctgaac tgatagcact cacccaggcc ctaaagatgg cagaaggtaa gaagctaaat     1740
gtttatactg atagccgtta tgcttttgct actgcccata tccatggaga aatatacaga     1800
aggcgtgggt tgctcacatc agaaggcaaa gagatcaaaa ataaagacga gatcttggcc     1860
ctactaaaag ccctctttct gcccaaaaga cttagcataa tccattgtcc aggacatcaa     1920
aagggacaca cgccgaggc tagaggcaac cggatggctg accaagcggc ccgaaaggca     1980
gccatcacag agactccaga cacctctacc ctcctcata                            2019

<210> SEQ ID NO 35
<211> LENGTH: 2019
<212> TYPE: DNA
<213> ORGANISM: Artificial Seuence
<220> FEATURE:
<223> OTHER INFORMATION: Reverse transcriptase variant K4(T306K) nucleic
      acid sequence

<400> SEQUENCE: 35
atgaccctaa atatagaaga tgagcatcgg ctacatgaga cctcaaaaga gccagatgtt       60
tctctagggt ccacatggct gtctgatttt cctcaggcct gggcgaaaac cgggggcatg      120
ggactggcag ttcgccaagc tcctctgatc atacctctga agcaacctc taccccgtg       180 tccataaaac aataccccat gtcacaagaa gccagactgg ggatcaagcc ccacatacag      240
agactgttgg accagggaat actggtaccc tgccagtccc cctggaacac gccctgcta      300 cccgttaaga aaccagggac taatgattat aggcctgtcc aggatctgag agaagtcaac      360
aagcgggtgg aagacatcca ccccaccgtg cccaaccctt acaacctctt gagcgggctc      420
ccaccgtccc accagtggta cactgtgctt gatttaaagg atgccttttt ctgcctgaga      480
ctccacccca ccagtcagcc tctcttcgcc tttgagtgga gagatccaga gatgggaatc      540
tcaggacaat tgacctggac cagactccca cagggtttca aaacagtcc caccctgttt      600 gatgaggcac tgcacagaga cctagcagac ttcggatcc agcacccaga cttgatcctg      660
ctacagtacg tggatgactt actgctggcc gccacttctg agctagactg ccaacaaggt      720
actcgggccc tgttacaaac cctagggaac ctcgggtatc gggcctcggc caagaaagcc      780
```

```
caaatttgcc agaaacaggt caagtatctg gggtatcttc taaaagaggg tcagagatgg      840
ctgactgagg ccagaaaaga gactgtgatg gggcagccta ctccgaagac ccctcgacaa      900
ctaagggagt tcctagggaa agcaggcttc tgtcgcctct ggatccctgg gtttgcagaa      960
atggcagccc ccttgtaccc tctcaccaaa acggggactc tgtttaattg gggcccagac     1020
caacaaaagg cctatcaaga aatcaagcaa gctcttctaa ctgccccagc cctggggttg     1080
ccagatttga ctaagccctt tgaactcttt gtcgacgaga agcagggcta cgccaaaggt     1140
gtcctaacgc aaaaactggg accttggcgt cggccggtgg cctacctgtc caaaaagcta     1200
gacccagtag cagctgggtg ccccccttgc ctacggatgg tagcagccat tgccgtactg     1260
acaaaggatg caggcaagct aaccatggga cagccactag tcattctggc cccccatgca     1320
gtagaggcac tagtcaaaca ccccccgac cgctggcttt ccaacgcccg gatgactcac     1380
tatcaggcct tgcttttgga cacggaccgg gtccagttcg gaccggtggt agccctgaac     1440
ccggctacgc tgctcccact gcctgaggaa gggctgcaac acaactgcct tgatatcctg     1500
gccgaagccc acggaacccg acccgaccta acggaccagc cgctcccaga cgccgaccac     1560
acctggtaca cggatggaag cagtctctta aagagggac agcgtaaggc gggagctgcg     1620
gtgaccaccg agaccgaggt aatctgggct aaagccctgc cagccgggac atccgctcag     1680
cgggctgaac tgatagcact caccccaggcc ctaaagatgg cagaaggtaa gaagctaaat     1740
gtttatactg atagccgtta tgcttttgct actgcccata tccatggaga aatatacaga     1800
aggcgtgggt tgctcacatc agaaggcaaa gagatcaaaa ataaagacga gatcttggcc     1860
ctactaaaag ccctctttct gcccaaaaga cttagcataa tccattgtcc aggacatcaa     1920
aagggacaca gcgccgaggc tagaggcaac cggatggctg accaagcggc ccgaaaggca     1980
gccatcacag agactccaga cacctctacc ctcctcata                            2019
```

<210> SEQ ID NO 36
<211> LENGTH: 2019
<212> TYPE: DNA
<213> ORGANISM: Artificial Seuence
<220> FEATURE:
<223> OTHER INFORMATION: Reverse transcriptase variant K3(D524A) nucleic acid sequence

<400> SEQUENCE: 36

```
atgaccctaa atatagaaga tgagcatcgg ctacatgaga cctcaaaaga gccagatgtt       60
tctctagggt ccacatggct gtctgatttt cctcaggcct gggcggaaac cgggggcatg      120
ggactggcag ttcgccaagc tcctctgatc atacctctga agcaacctc taccccgtg        180 tccataaaac aatacccat gtcacaagaa gccagactgg ggatcaagcc ccacatacag       240
agactgttgg accagggaat actggtaccc tgccagtccc cctggaacac gcccctgcta      300
cccgttaaga aaccagggac taatgattat aggcctgtcc aggatctgag agaagtcaac      360
aagcgggtgg aagacatcca ccccaccgtg cccaacccct acaacctctt gagcgggctc      420
ccaccgtccc accagtggta cactgtgctt gatttaaagg atgccttttt ctgcctgaga      480
ctccacccca ccagtcagcc tctcttcgcc tttgagtgga gagatccaga gatgggaatc      540
tcaggacaat tgacctggac cagactccca cagggtttca aaacagtcc cacctgtttt      600 gatgaggcac tgcacagaga cctagcagac ttcggatccc agcaccagga cttgatcctg      660
ctacagtacg tggatgactt actgctggcc gccacttctg agctagactg ccaacaaggt      720
actcgggccc tgttacaaac cctagggaac ctcgggtatc gggcctcggc caagaaagcc      780
```

```
caaatttgcc agaaacaggt caagtatctg gggtatcttc taaaagaggg tcagagatgg    840
ctgactgagg ccagaaaaga gactgtgatg gggcagccta ctccgaagac ccctcgacaa    900
ctaagggagt tcctagggac ggcaggcttc tgtcgcctct ggatccctgg gtttgcagaa    960
atggcagccc ccttgtaccc tctcaccaaa acggggactg tgtttaattg gggcccagac   1020
caacaaaagg cctatcaaga aatcaagcaa gctcttctaa ctgccccagc cctggggttg   1080
ccagatttga ctaagccctt tgaactcttt gtcgacgaga agcagggcta cgccaaaggt   1140
gtcctaacgc aaaaactggg accttggcgt cggccggtgg cctacctgtc caaaaagcta   1200
gacccagtag cagctgggtg ccccccttgc ctacggatgg tagcagccat tgccgtactg   1260
acaaaggatg caggcaagct aaccatggga cagccactag tcattctggc cccccatgca   1320
gtagaggcac tagtcaaaca ccccccgac cgctggcttt ccaacgcccg gatgactcac   1380
tatcaggcct tgcttttgga cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggctggaag cagtctctta caagagggac agcgtaaggc gggagctgcg   1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca gcgccgaggc tagaggcaac cggatggctg accaagcggc ccgaaaggca   1980
gccatcacag agactccaga cacctctacc ctcctcata                          2019
```

<210> SEQ ID NO 37
<211> LENGTH: 2019
<212> TYPE: DNA
<213> ORGANISM: Artificial Seuence
<220> FEATURE:
<223> OTHER INFORMATION: Reverse transcriptase variant K2(D524N) nucleic acid sequence

<400> SEQUENCE: 37

```
atgaccctaa atatagaaga tgagcatcgg ctacatgaga cctcaaaaga gccagatgtt     60
tctctagggt ccacatggct gtctgatttt cctcaggcct gggcgaaaac cgggggcatg    120
ggactggcag ttcgccaagc tcctctgatc atacctctga agcaacctc taccccgtg     180 tccataaaac aataccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
aagcgggtgg aagacatcca ccccaccgtg cccaaccctt acaacctctt gagcgggctc    420
ccaccgtccc accagtggta cactgtgctt gatttaaagg atgccttttt ctgcctgaga    480
ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
```

```
caaatttgcc agaaacaggt caagtatctg gggtatcttc taaaagaggg tcagagatgg      840
ctgactgagg ccagaaaaga gactgtgatg gggcagccta ctccgaagac ccctcgacaa      900
ctaagggagt tcctagggac ggcaggcttc tgtcgcctct ggatccctgg gtttgcagaa      960
atggcagccc ccttgtaccc tctcaccaaa acggggactg tgtttaattg gggcccagac     1020
caacaaaagg cctatcaaga aatcaagcaa gctcttctaa ctgccccagc cctggggttg     1080
ccagatttga ctaagccctt tgaactcttt gtcgacgaga agcagggcta cgccaaaggt     1140
gtcctaacgc aaaaactggg accttggcgt cggccggtgg cctacctgtc caaaaagcta     1200
gacccagtag cagctgggtg ccccccttgc ctacggatgg tagcagccat tgccgtactg     1260
acaaaggatg caggcaagct aaccatggga cagccactag tcattctggc cccccatgca     1320
gtagaggcac tagtcaaaca ccccccgac cgctggcttt ccaacgcccg gatgactcac      1380
tatcaggcct tgcttttgga cacggaccgg gtccagttcg gaccggtggt agccctgaac     1440
ccggctacgc tgctcccact gcctgaggaa gggctgcaac acaactgcct tgatatcctg     1500
gccgaagccc acggaacccg acccgaccta acggaccagc cgctcccaga cgccgaccac     1560
acctggtaca cgaacggaag cagtctctta caagagggac agcgtaaggc gggagctgcg     1620
gtgaccaccg agaccgaggt aatctgggct aaagccctgc cagccgggac atccgctcag     1680
cgggctgaac tgatagcact cacccaggcc ctaaagatgg cagaaggtaa gaagctaaat     1740
gtttatactg atagccgtta tgcttttgct actgcccata tccatggaga aatatacaga     1800
aggcgtgggt tgctcacatc agaaggcaaa gagatcaaaa ataaagacga gatcttggcc     1860
ctactaaaag ccctctttct gcccaaaaga cttagcataa tccattgtcc aggacatcaa     1920
aagggacaca cgcgccgaggc tagaggcaac cggatggctg accaagcggc ccgaaaggca     1980
gccatcacag agactccaga cacctctacc ctcctcata                           2019

<210> SEQ ID NO 38
<211> LENGTH: 2019
<212> TYPE: DNA
<213> ORGANISM: Artificial Seuence
<220> FEATURE:
<223> OTHER INFORMATION: Reverse transcriptase variant
      LT(H204R+M289L+T306K+F309N) nucleic acid sequence

<400> SEQUENCE: 38
atgaccctaa atatagaaga tgagcatcgg ctacatgaga cctcaaaaga gccagatgtt       60
tctctagggt ccacatggct gtctgatttt cctcaggcct gggcggaaac cgggggcatg      120
ggactggcag ttcgccaagc tcctctgatc atacctctga agcaacctc tacccccgtg       180 tccataaaac aataccccat gtcacaagaa gccagactgg ggatcaagcc ccacatacag      240
agactgttgg accagggaat actggtaccc tgccagtccc cctggaacac gcccctgcta      300
cccgttaaga aaccagggac taatgattat aggcctgtcc aggatctgag agaagtcaac      360
aagcgggtgg aagacatcca ccccaccgtg cccaacccct tacaacctctt gagcgggctc      420 ccaccgtccc accagtggta cactgtgctt gatttaaagg atgcctttttt ctgcctgaga     480 ctccacccca ccagtcagcc tctcttcgcc tttgagtgga gagatccaga gatgggaatc      540
tcaggacaat tgacctggac cagactccca cagggtttca aaaacagtcc caccctgttt     600
gatgaggcac tgcgcagaga cctagcagac ttccggatcc agcacccaga cttgatcctg      660
ctacagtacg tggatgactt actgctggcc gccacttctg agctagactg ccaacaaggt      720
actcgggccc tgttacaaac cctagggaac ctcgggtatc gggcctcggc caagaaagcc      780
```

```
caaatttgcc agaaacaggt caagtatctg gggtatcttc taaaagaggg tcagagatgg    840
ctgactgagg ccagaaaaga gactgtgctg gggcagccta ctccgaagac ccctcgacaa    900
ctaagggagt tcctagggaa agcaggcaac tgtcgcctct ggatccctgg gtttgcagaa    960
atggcagccc ccttgtaccc tctcaccaaa acggggactc tgtttaattg gggcccagac   1020
caacaaaagg cctatcaaga aatcaagcaa gctcttctaa ctgccccagc cctggggttg   1080
ccagatttga ctaagccctt tgaactcttt gtcgacgaga agcagggcta cgccaaaggt   1140
gtcctaacgc aaaaactggg accttggcgt cggccggtgg cctacctgtc caaaaagcta   1200
gacccagtag cagctgggtg gccccccttgc ctacggatgg tagcagccat tgccgtactg   1260
acaaaggatg caggcaagct aaccatggga cagccactag tcattctggc cccccatgca   1320
gtagaggcac tagtcaaaca accccccgac cgctggcttt ccaacgcccg gatgactcac   1380
tatcaggcct tgcttttgga cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggatggaag cagtctctta caagagggga agcgtaaggc gggagctgcg   1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca gcgccgaggc tagaggcaac cggatggctg accaagcggc ccgaaaggca   1980
gccatcacag agactccaga cacctctacc ctcctcata                          2019
```

<210> SEQ ID NO 39
<211> LENGTH: 673
<212> TYPE: PRT
<213> ORGANISM: Artificial Seuence
<220> FEATURE:
<223> OTHER INFORMATION: Reverse transcriptase variant C3+D1 amino acid
      sequence

<400> SEQUENCE: 39

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Pro Gly Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
```

```
               130                 135                 140
Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
            210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Lys
            275                 280                 285

Val Met Gly Gln Pro Thr Pro Lys Thr Pro Arg Gln Leu Arg Glu Phe
            290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
            370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
                515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560
```

```
Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
        580                 585                 590

His Ile His Gly Glu Ile Tyr Arg Arg Arg Gly Leu Leu Thr Ser Glu
    595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile

<210> SEQ ID NO 40
<211> LENGTH: 673
<212> TYPE: PRT
<213> ORGANISM: Artificial Seuence
<220> FEATURE:
<223> OTHER INFORMATION: Reverse transcriptase variant C3+K1 amino acid
      sequence

<400> SEQUENCE: 40

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Pro Gly Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240
```

```
Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Lys Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655
```

Ala Arg Lys Ala Ala Ile Thr Glu Thr Pro Asp Thr Ser Thr Leu Leu
            660                 665                 670

Ile

<210> SEQ ID NO 41
<211> LENGTH: 673
<212> TYPE: PRT
<213> ORGANISM: Artificial Seuence
<220> FEATURE:
<223> OTHER INFORMATION: Reverse transcriptase variant C3+K4 amino acid
      sequence

<400> SEQUENCE: 41

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Pro Gly Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

```
Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile
```

<210> SEQ ID NO 42
<211> LENGTH: 673
<212> TYPE: PRT
<213> ORGANISM: Artificial Seuence
<220> FEATURE:
<223> OTHER INFORMATION: Reverse transcriptase variant C3+K3 amino acid
      sequence

<400> SEQUENCE: 42

```
Met Thr Leu Asn Ile Glu Asp Glu His Arg Leu His Glu Thr Ser Lys
1               5                   10                  15
```

```
Glu Pro Asp Val Ser Leu Gly Ser Thr Trp Leu Ser Asp Phe Pro Gln
             20                  25                  30

Ala Trp Ala Glu Thr Gly Gly Met Gly Leu Ala Val Arg Gln Ala Pro
         35                  40                  45

Leu Ile Ile Pro Leu Lys Pro Gly Ser Thr Pro Val Ser Ile Lys Gln
 50                  55                  60

Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
             85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
        210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
        290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
```

```
                 435                 440                 445
Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Ala Gly Ser Ser
            515                 520                 525

Leu Leu Gln Glu Gly Gln Arg Lys Ala Gly Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Gly Leu Leu Thr Ser Glu
            595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile

<210> SEQ ID NO 43
<211> LENGTH: 673
<212> TYPE: PRT
<213> ORGANISM: Artificial Seuence
<220> FEATURE:
<223> OTHER INFORMATION: Reverse transcriptase variant C3+K2 amino acid
      sequence

<400> SEQUENCE: 43

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Pro Gly Ser Thr Pro Val Ser Ile Lys Gln
        50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
```

-continued

```
            115                 120                 125
Thr Val Pro Asn Pro Tyr Asn Leu Leu Ser Gly Leu Pro Pro Ser His
            130                 135                 140
Gln Trp Tyr Thr Val Leu Asp Leu Lys Asp Ala Phe Phe Cys Leu Arg
145                 150                 155                 160
Leu His Pro Thr Ser Gln Pro Leu Phe Ala Phe Glu Trp Arg Asp Pro
                    165                 170                 175
Glu Met Gly Ile Ser Gly Gln Leu Thr Trp Thr Arg Leu Pro Gln Gly
                180                 185                 190
Phe Lys Asn Ser Pro Thr Leu Phe Asp Glu Ala Leu His Arg Asp Leu
            195                 200                 205
Ala Asp Phe Arg Ile Gln His Pro Asp Leu Ile Leu Leu Gln Tyr Val
        210                 215                 220
Asp Asp Leu Leu Leu Ala Ala Thr Ser Glu Leu Asp Cys Gln Gln Gly
225                 230                 235                 240
Thr Arg Ala Leu Leu Gln Thr Leu Gly Asn Leu Gly Tyr Arg Ala Ser
                    245                 250                 255
Ala Lys Lys Ala Gln Ile Cys Gln Lys Gln Val Lys Tyr Leu Gly Tyr
                260                 265                 270
Leu Leu Lys Glu Gly Gln Arg Trp Leu Thr Glu Ala Arg Lys Glu Thr
            275                 280                 285
Val Met Gly Gln Pro Thr Pro Lys Thr Pro Arg Gln Leu Arg Glu Phe
        290                 295                 300
Leu Gly Thr Ala Gly Phe Cys Arg Leu Trp Ile Pro Gly Phe Ala Glu
305                 310                 315                 320
Met Ala Ala Pro Leu Tyr Pro Leu Thr Lys Thr Gly Thr Leu Phe Asn
                    325                 330                 335
Trp Gly Pro Asp Gln Gln Lys Ala Tyr Gln Glu Ile Lys Gln Ala Leu
                340                 345                 350
Leu Thr Ala Pro Ala Leu Gly Leu Pro Asp Leu Thr Lys Pro Phe Glu
            355                 360                 365
Leu Phe Val Asp Glu Lys Gln Gly Tyr Ala Lys Gly Val Leu Thr Gln
        370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                    405                 410                 415
Ile Ala Val Leu Thr Lys Asp Ala Gly Lys Leu Thr Met Gly Gln Pro
                420                 425                 430
Leu Val Ile Leu Ala Pro His Ala Val Glu Ala Leu Val Lys Gln Pro
            435                 440                 445
Pro Asp Arg Trp Leu Ser Asn Ala Arg Met Thr His Tyr Gln Ala Leu
        450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                    485                 490                 495
Leu Asp Ile Leu Ala Glu Ala His Gly Thr Arg Pro Asp Leu Thr Asp
                500                 505                 510
Gln Pro Leu Pro Asp Ala Asp His Thr Trp Tyr Thr Asn Gly Ser Ser
            515                 520                 525
Leu Leu Gln Glu Gly Gln Arg Lys Ala Gly Ala Ala Val Thr Thr Glu
        530                 535                 540
```

```
Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Gly Leu Leu Thr Ser Glu
            595                 600                 605

Gly Lys Glu Ile Lys Asn Lys Asp Glu Ile Leu Ala Leu Leu Lys Ala
                610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile

<210> SEQ ID NO 44
<211> LENGTH: 673
<212> TYPE: PRT
<213> ORGANISM: Artificial Seuence
<220> FEATURE:
<223> OTHER INFORMATION: Reverse transcriptase variant C3+LT amino acid
      sequence

<400> SEQUENCE: 44

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Pro Gly Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu Arg Arg Asp Leu
        195                 200                 205

Ala Asp Phe Arg Ile Gln His Pro Asp Leu Ile Leu Leu Gln Tyr Val
210                 215                 220
```

-continued

```
Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
            275                 280                 285

Val Leu Gly Gln Pro Thr Pro Lys Thr Pro Arg Gln Leu Arg Glu Phe
        290                 295                 300

Leu Gly Lys Ala Gly Asn Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640
```

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
        660                 665                 670

Ile

<210> SEQ ID NO 45
<211> LENGTH: 2019
<212> TYPE: DNA
<213> ORGANISM: Artificial Seuence
<220> FEATURE:
<223> OTHER INFORMATION: Reverse transcriptase variant C3+D1 nucleic
      acid sequence

<400> SEQUENCE: 45

| | | | |
|---|---|---|---|
| atgaccctaa | atatagaaga | tgagcatcgg | ctacatgaga cctcaaaaga gccagatgtt | 60 |
| tctctagggt | ccacatggct | gtctgatttt | cctcaggcct gggcggaaac cgggggcatg | 120 |
| ggactggcag | ttcgccaagc | tcctctgatc | atacctctga aaccgggttc taccccgtg | 180 |
| tccataaaac | aataccccat | gtcacaagaa | gccagactgg ggatcaagcc ccacatacag | 240 |
| agactgttgg | accagggaat | actggtaccc | tgccagtccc cctggaacac gccctgcta | 300 |
| cccgttaaga | aaccagggac | taatgattat | aggcctgtcc aggatctgag agaagtcaac | 360 |
| aagcgggtgg | aagacatcca | ccccaccgtg | cccaaccctt acaacctctt gagcgggctc | 420 |
| ccaccgtccc | accagtggta | cactgtgctt | gatttaaagg atgcctttt ctgcctgaga | 480 |
| ctccacccca | ccagtcagcc | tctcttcgcc | tttgagtgga gagatccaga gatgggaatc | 540 |
| tcaggacaat | tgacctggac | cagactccca | cagggtttca aaaacagtcc cacctgttt | 600 |
| gatgaggcac | tgcacagaga | cctagcagac | ttccggatcc agcacccaga cttgatcctg | 660 |
| ctacagtacg | tggatgactt | actgctggcc | gccacttctg agctagactg ccaacaaggt | 720 |
| actcgggccc | tgttacaaac | cctagggaac | ctcgggtatc gggcctcggc caagaaagcc | 780 |
| caaatttgcc | agaaacaggt | caagtatctg | gggtatcttc taaaagaggg tcagagatgg | 840 |
| ctgactgagg | ccagaaaaga | gaaagtgatg | gggcagccta ctccgaagac ccctcgacaa | 900 |
| ctaagggagt | tcctagggac | ggcaggcttc | tgtcgcctct ggatccctgg gtttgcagaa | 960 |
| atggcagccc | ccttgtaccc | tctcaccaaa | acggggactc tgtttaattg gggcccagac | 1020 |
| caacaaaagg | cctatcaaga | aatcaagcaa | gctcttctaa ctgccccagc cctggggttg | 1080 |
| ccagatttga | ctaagccctt | tgaactcttt | gtcgacgaga gcagggcta cgccaaaggt | 1140 |
| gtcctaacgc | aaaaactggg | accttggcgt | cggccggtgg cctacctgtc caaaaagcta | 1200 |
| gacccagtag | cagctgggtg | gccccttgc | ctacggatgg tagcagccat tgccgtactg | 1260 |
| acaaaggatg | caggcaagct | aaccatggga | cagccactag tcattctggc ccccatgca | 1320 |
| gtagaggcac | tagtcaaaca | accccccgac | cgctggcttt ccaacgcccg gatgactcac | 1380 |
| tatcaggcct | tgcttttgga | cacgaccgg | gtccagttcg accggtggt agccctgaac | 1440 |
| ccggctacgc | tgctcccact | gcctgaggaa | gggctgcaac acaactgcct tgatatcctg | 1500 |
| gccgaagccc | acggaacccg | acccgaccta | acgaccagc cgctcccaga cgccgaccac | 1560 |
| acctggtaca | cggatggaag | cagtctctta | caagagggac agcgtaaggc gggagctgcg | 1620 |
| gtgaccaccg | agaccgaggt | aatctgggct | aaagccctgc cagccgggac atccgctcag | 1680 |
| cgggctgaac | tgatagcact | cacccaggcc | ctaaagatgg cagaaggtaa gaagctaaat | 1740 |
| gtttatactg | atagccgtta | tgcttttgct | actgcccata tccatggaga aatatacaga | 1800 |

| | |
|---|---|
| aggcgtgggt tgctcacatc agaaggcaaa gagatcaaaa ataaagacga gatcttggcc | 1860 |
| ctactaaaag ccctctttct gcccaaaaga cttagcataa tccattgtcc aggacatcaa | 1920 |
| aagggacaca gcgccgaggc tagaggcaac cggatggctg accaagcggc ccgaaaggca | 1980 |
| gccatcacag agactccaga cacctctacc ctcctcata | 2019 |

<210> SEQ ID NO 46
<211> LENGTH: 2019
<212> TYPE: DNA
<213> ORGANISM: Artificial Seuence
<220> FEATURE:
<223> OTHER INFORMATION: Reverse transcriptase variant C3+K1 nucleic acid sequence

<400> SEQUENCE: 46

| | |
|---|---|
| atgaccctaa atatagaaga tgagcatcgg ctacatgaga cctcaaaaga gccagatgtt | 60 |
| tctctagggt ccacatggct gtctgatttt cctcaggcct gggcggaaac cggggggcatg | 120 |
| ggactggcag ttcgccaagc tcctctgatc atacctctga aaccgggttc taccccgtg | 180 |
| tccataaaac ataccccat gtcacaagaa gccagactgg ggatcaagcc ccacatacag | 240 |
| agactgttgg accagggaat actggtaccc tgccagtccc cctggaacac gcccctgcta | 300 |
| cccgttaaga aaccagggac taatgattat aggcctgtcc aggatctgag agaagtcaac | 360 |
| aagcgggtgg aagacatcca ccccaccgtg cccaacccctt acaacctctt gagcgggctc | 420 |
| ccaccgtccc accagtggta cactgtgctt gatttaaagg atgccttttt ctgcctgaga | 480 |
| ctccacccca ccagtcagcc tctcttcgcc tttgagtgga gagatccaga gatgggaatc | 540 |
| tcaggacaat tgacctggac cagactccca cagggtttca aaaacagtcc caccctgttt | 600 |
| gatgaggcac tgcacagaga cctagcagac ttccggatcc agcacccaga cttgatcctg | 660 |
| ctacagtacg tggatgactt actgctggcc gccacttctg agctagactg ccaacaaggt | 720 |
| actcgggccc tgttacaaac cctagggaac ctcgggtatc gggcctcggc caagaaagcc | 780 |
| caaatttgcc agaaacaggt caagtatctg gggtatcttc taaaagaggg tcagagatgg | 840 |
| ctgactgagg ccagaaaaga actgtgatg gggaaaccta ctccgaagac ccctcgacaa | 900 |
| ctaagggagt tcctagggac ggcaggcttc tgtcgcctct ggatccctgg gtttgcagaa | 960 |
| atggcagccc ccttgtaccc tctcaccaaa acggggactc tgtttaattg gggcccagac | 1020 |
| caacaaaagg cctatcaaga aatcaagcaa gctcttctaa ctgccccagc cctgggttg | 1080 |
| ccagatttga ctaagccctt tgaactcttt gtcgacgaga agcagggcta cgccaaaggt | 1140 |
| gtcctaacgc aaaaactggg accttggcgt cggccggtgg cctacctgtc caaaaagcta | 1200 |
| gacccagtag cagctgggtg gccccttgc ctacggatgg tagcagccat tgccgtactg | 1260 |
| acaaaggatg caggcaagct aaccatggga cagccactag tcattctggc cccccatgca | 1320 |
| gtagaggcac tagtcaaaca accccccgac cgctggcttt ccaacgcccg gatgactcac | 1380 |
| tatcaggcct tgcttttgga cacgaccgg gtccagttcg gaccggtggt agccctgaac | 1440 |
| ccggctacgc tgctcccact gcctgaggaa gggctgcaac acaactgcct tgatatcctg | 1500 |
| gccgaagccc acggaaccccg acccgaccta acgaccagc cgctcccaga cgccgaccac | 1560 |
| acctggtaca cggatggaag cagtctctta caagaggac agcgtaaggc gggagctgcg | 1620 |
| gtgaccaccg agaccgaggt aatctgggct aaagccctgc cagccgggac atccgctcag | 1680 |
| cgggctgaac tgatagcact cacccaggcc ctaaagatgg cagaaggtaa gaagctaaat | 1740 |
| gtttatactg atagccgtta tgcttttgct actgcccata tccatggaga aatatacaga | 1800 |

```
aggcgtgggt tgctcacatc agaaggcaaa gagatcaaaa ataaagacga gatcttggcc    1860
ctactaaaag ccctctttct gcccaaaaga cttagcataa tccattgtcc aggacatcaa    1920
aagggacaca gcgccgaggc tagaggcaac cggatggctg accaagcggc ccgaaaggca    1980
gccatcacag agactccaga cacctctacc ctcctcata                           2019
```

<210> SEQ ID NO 47
<211> LENGTH: 2019
<212> TYPE: DNA
<213> ORGANISM: Artificial Seuence
<220> FEATURE:
<223> OTHER INFORMATION: Reverse transcriptase variant C3+K4 nucleic acid sequence

<400> SEQUENCE: 47

```
atgaccctaa atatagaaga tgagcatcgg ctacatgaga cctcaaaaga gccagatgtt      60
tctctagggt ccacatggct gtctgatttt cctcaggcct gggcggaaac cgggggcatg     120
ggactggcag ttcgccaagc tcctctgatc atacctctga aaccgggttc taccccgtg      180 tccataaaac aataccccat gtcacaagaa gccagactgg ggatcaagcc ccacatacag     240
agactgttgg accagggaat actggtaccc tgccagtccc cctggaacac gcccctgcta     300
cccgttaaga aaccagggac taatgattat aggcctgtcc aggatctgag agaagtcaac     360
aagcgggtgg aagacatcca ccccaccgtg cccaaccctt acaacctctt gagcgggctc     420
ccaccgtccc accagtggta cactgtgctt gatttaaagg atgccttttt ctgcctgaga     480
ctccacccca ccagtcagcc tctcttcgcc tttgagtgga gagatccaga gatgggaatc     540
tcaggacaat tgacctggac cagactccca cagggtttca aaaacagtcc caccctgttt     600
gatgaggcac tgcacagaga cctagcagac ttccggatcc agcacccaga cttgatcctg     660
ctacagtacg tggatgactt actgctggcc gccacttctg agctagactg ccaacaaggt     720
actcgggccc tgttacaaac cctagggaac ctcgggtatc gggcctcggc caagaaagcc     780
caaatttgcc agaaacaggt caagtatctg gggtatcttc taaaagaggg tcagagatgg     840
ctgactgagg ccagaaaaga gactgtgatg gggcagccta ctccgaagac ccctcgacaa     900
ctaagggagt cctagggaa agcaggcttc tgtcgcctct ggatccctgg gtttgcagaa     960
atggcagccc ccttgtaccc tctcaccaaa acggggactc tgtttaattg gggcccagac    1020
caacaaaagg cctatcaaga aatcaagcaa gctcttctaa ctgccccagc cctggggttg    1080
ccagatttga ctaagccctt tgaactcttt gtcgacgaga agcagggcta cgccaaaggt    1140
gtcctaacgc aaaaactggg accttggcgt cggccggtgg cctacctgtc caaaaagcta    1200
gacccagtag cagctgggtg gccccttgc ctacggatgg tagcagccat tgccgtactg    1260
acaaaggatg caggcaagct aaccatggga cagccactag tcattctggc ccccatgca    1320 gtagaggcac tagtcaaaca acccccgac cgctggcttt ccaacgcccg gatgactcac    1380
tatcaggcct gcttttga cacgaccgg gtccagttcg accggtggt agccctgaac    1440 ccggctacgc tgctcccact gcctgaggaa gggctgcaac acaactgcct tgatatcctg    1500
gccgaagccc acggaacccg acccgaccta acgaccagc cgctcccaga cgccgaccac    1560
acctggtaca cggatggaag cagtctctta caagagggac agcgtaaggc gggagctgcg    1620
gtgaccaccg agaccgaggt aatctgggct aaagccctgc cagccgggac atccgctcag    1680
cgggctgaac tgatagcact cacccaggcc ctaaagatgg cagaaggtaa gaagctaaat    1740
gtttatactg atagccgtta tgcttttgct actgcccata tccatggaga aatatacaga    1800
```

-continued

| | |
|---|---|
| aggcgtgggt tgctcacatc agaaggcaaa gagatcaaaa ataaagacga gatcttggcc | 1860 |
| ctactaaaag ccctctttct gcccaaaaga cttagcataa tccattgtcc aggacatcaa | 1920 |
| aagggacaca gcgccgaggc tagaggcaac cggatggctg accaagcggc ccgaaaggca | 1980 |
| gccatcacag agactccaga cacctctacc ctcctcata | 2019 |

<210> SEQ ID NO 48
<211> LENGTH: 2019
<212> TYPE: DNA
<213> ORGANISM: Artificial Seuence
<220> FEATURE:
<223> OTHER INFORMATION: Reverse transcriptase variant C3+K3 nucleic acid sequence

<400> SEQUENCE: 48

| | |
|---|---|
| atgaccctaa atatagaaga tgagcatcgg ctacatgaga cctcaaaaga gccagatgtt | 60 |
| tctctagggt ccacatggct gtctgatttt cctcaggcct gggcggaaac cggggggcatg | 120 |
| ggactggcag ttcgccaagc tcctctgatc atacctctga aaccgggttc taccccgtg | 180 |
| tccataaaac aatacccat gtcacaagaa gccagactgg ggatcaagcc ccacatacag | 240 |
| agactgttgg accagggaat actggtaccc tgccagtccc cctggaacac gcccctgcta | 300 |
| cccgttaaga aaccagggac taatgattat aggcctgtcc aggatctgag agaagtcaac | 360 |
| aagcgggtgg aagacatcca ccccaccgtg cccaacccctt acaacctctt gagcgggctc | 420 |
| ccaccgtccc accagtggta cactgtgctt gatttaaagg atgccttttt ctgcctgaga | 480 |
| ctccacccca ccagtcagcc tctcttcgcc tttgagtgga gagatccaga gatgggaatc | 540 |
| tcaggacaat tgacctggac cagactccca cagggtttca aaaacagtcc caccctgttt | 600 |
| gatgaggcac tgcacagaga cctagcagac ttccggatcc agcacccaga cttgatcctg | 660 |
| ctacagtacg tggatgactt actgctggcc gccacttctg agctagactg ccaacaaggt | 720 |
| actcgggccc tgttacaaac cctagggaac ctcgggtatc gggcctcggc caagaaagcc | 780 |
| caaatttgcc agaaacaggt caagtatctg gggtatcttc taaaagaggg tcagagatgg | 840 |
| ctgactgagg ccagaaaaga dactgtgatg gggcagccta ctccgaagac ccctcgacaa | 900 |
| ctaagggagt tcctagggac ggcaggcttc tgtcgcctct ggatccctgg gtttgcagaa | 960 |
| atggcagccc ccttgtaccc tctcaccaaa acggggactc tgtttaattg gggcccagac | 1020 |
| caacaaaagg cctatcaaga aatcaagcaa gctcttctaa ctgccccagc cctggggttg | 1080 |
| ccagatttga ctaagccctt tgaactcttt gtcgacgaga agcagggcta cgccaaaggt | 1140 |
| gtcctaacgc aaaaactggg accttggcgt cggccggtgg cctacctgtc caaaaagcta | 1200 |
| gacccagtag cagctgggtg gcccccttgc ctacggatgg tagcagccat tgccgtactg | 1260 |
| acaaaggatg caggcaagct aaccatggga cagccactag tcattctggc cccccatgca | 1320 |
| gtagaggcac tagtcaaaca acccccgac cgctggcttt ccaacgcccg gatgactcac | 1380 |
| tatcaggcct tgcttttgga cacgaccgg gtccagttcg accggtggt agccctgaac | 1440 |
| ccggctacgc tgctcccact gcctgaggaa gggctgcaac acaactgcct tgatatcctg | 1500 |
| gccgaagccc acggaacccg accccgaccta acgaccagc cgctcccaga cgccgaccac | 1560 |
| acctggtaca cggctggaag cagtctctta aagagggac agcgtaaggc gggagctgcg | 1620 |
| gtgaccaccg agaccgaggt aatctgggct aaagccctgc cagccgggac atccgctcag | 1680 |
| cgggctgaac tgatagcact cacccaggcc ctaaagatgg cagaaggtaa gaagctaaat | 1740 |
| gtttatactg atagccgtta tgcttttgct actgcccata tccatggaga aatatacaga | 1800 |

| | |
|---|---:|
| aggcgtgggt tgctcacatc agaaggcaaa gagatcaaaa ataaagacga gatcttggcc | 1860 |
| ctactaaaag ccctctttct gcccaaaaga cttagcataa tccattgtcc aggacatcaa | 1920 |
| aagggacaca gcgccgaggc tagaggcaac cggatggctg accaagcggc ccgaaaggca | 1980 |
| gccatcacag agactccaga cacctctacc ctcctcata | 2019 |

<210> SEQ ID NO 49
<211> LENGTH: 2019
<212> TYPE: DNA
<213> ORGANISM: Artificial Seuence
<220> FEATURE:
<223> OTHER INFORMATION: Reverse transcriptase variant C3+K2 nucleic acid sequence

<400> SEQUENCE: 49

| | |
|---|---:|
| atgaccctaa atatagaaga tgagcatcgg ctacatgaga cctcaaaaga gccagatgtt | 60 |
| tctctagggt ccacatggct gtctgatttt cctcaggcct gggcggaaac cgggggcatg | 120 |
| ggactggcag ttcgccaagc tcctctgatc atacctctga accgggttc taccccgtg | 180 |
| tccataaaac ataccccat gtcacaagaa gccagactgg ggatcaagcc ccacatacag | 240 |
| agactgttgg accagggaat actggtaccc tgccagtccc cctggaacac gcccctgcta | 300 |
| cccgttaaga accagggac taatgattat aggcctgtcc aggatctgag agaagtcaac | 360 |
| aagcgggtgg aagacatcca ccccaccgtg cccaaccctt acaacctctt gagcgggctc | 420 |
| ccaccgtccc accagtggta cactgtgctt gatttaaagg atgcctttt ctgcctgaga | 480 |
| ctccacccca ccagtcagcc tctcttcgcc tttgagtgga gagatccaga gatgggaatc | 540 |
| tcaggacaat tgacctggac cagactccca cagggttca aaaacagtcc caccctgttt | 600 |
| gatgaggcac tgcacagaga cctagcagac ttccggatcc agcacccaga cttgatcctg | 660 |
| ctacagtacg tggatgactt actgctggcc gccacttctg agctagactg ccaacaaggt | 720 |
| actcgggccc tgttacaaac cctagggaac ctcgggtatc gggcctcggc caagaaagcc | 780 |
| caaatttgcc agaaacaggt caagtatctg gggtatcttc taaaagaggg tcagagatgg | 840 |
| ctgactgagg ccagaaaaga ctgtgatg gggcagccta ctccgaagac ccctcgacaa | 900 |
| ctaagggagt tcctagggac ggcaggcttc tgtcgcctct ggatccctgg gtttgcagaa | 960 |
| atggcagccc ccttgtaccc tctcaccaaa acggggactc tgtttaattg gggcccagac | 1020 |
| caacaaaagg cctatcaaga aatcaagcaa gctcttctaa ctgccccagc cctggggttg | 1080 |
| ccagatttga ctaagcccct tgaactcttt gtcgacgaga agcagggcta cgccaaggt | 1140 |
| gtcctaacgc aaaaactggg accttggcgt cggccggtgg cctacctgtc caaaaagcta | 1200 |
| gacccagtag cagctgggtg gccccttgc ctacggatgg tagcagccat tgccgtactg | 1260 |
| acaaaggatg caggcaagct aaccatggga cagccactag tcattctggc cccccatgca | 1320 |
| gtagaggcac tagtcaaaca accccccgac cgctggcttt ccaacgcccg gatgactcac | 1380 |
| tatcaggcct tgcttttgga cacgaccgg gtccagttcg accggtggt agccctgaac | 1440 |
| ccggctacgc tgctcccact gcctgaggaa gggctgcaac acaactgcct tgatatcctg | 1500 |
| gccgaagccc acggaacccg acccgaccta acgaccagc cgctcccaga cgccgaccac | 1560 |
| acctggtaca cgaacggaag cagtctctta caagagggac agcgtaaggc gggagctgcg | 1620 |
| gtgaccaccg agaccgaggt aatctgggct aaagccctgc cagccgggac atccgctcag | 1680 |
| cgggctgaac tgatagcact cacccaggcc ctaaagatgg cagaaggtaa gaagctaaat | 1740 |
| gtttatactg atagccgtta tgcttttgct actgcccata tccatggaga aatatacaga | 1800 |

```
aggcgtgggt tgctcacatc agaaggcaaa gagatcaaaa ataaagacga gatcttggcc   1860
ctactaaaag ccctctttct gcccaaaaga cttagcataa tccattgtcc aggacatcaa   1920
aagggacaca gcgccgaggc tagaggcaac cggatggctg accaagcggc ccgaaaggca   1980
gccatcacag agactccaga cacctctacc ctcctcata                          2019
```

<210> SEQ ID NO 50  
<211> LENGTH: 2019  
<212> TYPE: DNA  
<213> ORGANISM: Artificial Seuence  
<220> FEATURE:  
<223> OTHER INFORMATION: Reverse transcriptase variant C3+LT nucleic acid sequence

<400> SEQUENCE: 50

```
atgaccctaa atatagaaga tgagcatcgg ctacatgaga cctcaaaaga gccagatgtt     60
tctctagggt ccacatggct gtctgatttt cctcaggcct gggcggaaac cggggggcatg   120 ggactggcag ttcgccaagc tcctctgatc atacctctga accgggttc taccccgtg     180 tccataaaac aataccccat gtcacaagaa gccagactgg ggatcaagcc ccacatacag   240
agactgttgg accagggaat actggtaccc tgccagtccc cctggaacac gcccctgcta   300
cccgttaaga aaccagggac taatgattat aggcctgtcc aggatctgag agaagtcaac   360
aagcgggtgg aagacatcca ccccaccgtg cccaacccdtt acaacctctt gagcgggctc   420
ccaccgtccc accagtggta cactgtgctt gatttaaagg atgcctttt  ctgcctgaga   480 ctccaccca  ccagtcagcc tctcttcgcc tttgagtgga gagatccaga gatgggaatc   540
tcaggacaat tgacctggac cagactccca cagggtttca aaaacagtcc caccctgttt   600
gatgaggcac tgcgcagaga cctagcagac ttccggatcc agcacccaga cttgatcctg   660
ctacagtacg tggatgactt actgctggcc gccacttctg agctagactg ccaacaaggt   720
actcgggccc tgttacaaac cctagggaac ctcgggtatc gggcctcggc caagaaagcc   780
caaatttgcc agaaacaggt caagtatctg gggtatcttc taaaagaggg tcagagatgg   840
ctgactgagg ccagaaaaga gactgtgctg gggcagccta ctccgaagac ccctcgacaa   900
ctaagggagt tcctagggaa agcaggcaac tgtcgcctct ggatccctgg gtttgcagaa   960
atggcagccc ccttgtaccc tctcaccaaa acggggactc tgtttaattg gggcccagac  1020
caacaaaagg cctatcaaga aatcaagcaa gctcttctaa ctgccccagc cctggggttg  1080
ccagatttga ctaagccctt tgaactcttt gtcgacgaga gcagggcta cgccaaaggt  1140 gtcctaacgc aaaaactggg accttggcgt cggccgtgg cctacctgtc caaaagcta   1200 gacccagtag cagctgggtg gccccttgc ctacggatgg tagcagccat tgccgtactg  1260
acaaaggatg caggcaagct aaccatggga cagccactag tcattctggc ccccatgca   1320 gtagaggcac tagtcaaaca accccccgac cgctggcttt ccaacgcccg gatgactcac  1380
tatcaggcct gcttttgga cacgaccggg tccagttcg accggtggt agccctgaac   1440 ccggctacgc tgctcccact gcctgaggaa gggctgcaac acaactgcct tgatatcctg  1500
gccgaagccc acggaacccg acccgaccta acgaccagc cgctcccaga cgccgaccac  1560
acctggtaca cggatggaag cagtctctta caagaggac agcgtaaggc gggagctgcg  1620
gtgaccaccg agaccgaggt aatctgggct aaagccctgc cagccgggac atccgctcag  1680
cgggctgaac tgatagcact cacccaggcc ctaaagatgg cagaaggtaa gaagctaaat  1740
gtttatactg atagccgtta tgcttttgct actgcccata tccatggaga aatatacaga  1800
```

-continued

```
aggcgtgggt tgctcacatc agaaggcaaa gagatcaaaa ataaagacga gatcttggcc      1860
ctactaaaag ccctctttct gcccaaaaga cttagcataa tccattgtcc aggacatcaa      1920
aagggacaca gcgccgaggc tagaggcaac cggatggctg accaagcggc ccgaaaggca      1980
gccatcacag agactccaga cacctctacc ctcctcata                             2019
```

```
<210> SEQ ID NO 51
<211> LENGTH: 673
<212> TYPE: PRT
<213> ORGANISM: Artificial Seuence
<220> FEATURE:
<223> OTHER INFORMATION: Reverse transcriptase variant C5(D209P+I212A)
      amino acid sequence

<400> SEQUENCE: 51
```

| | | | | | | | | | | | | | | |
|---|---|---|---|---|---|---|---|---|---|---|---|---|---|---|
| Met | Thr | Leu | Asn | Ile | Glu | Asp | Glu | His | Arg | Leu | His | Glu | Thr | Ser | Lys |
| 1 | | | | 5 | | | | | 10 | | | | | 15 | |
| Glu | Pro | Asp | Val | Ser | Leu | Gly | Ser | Thr | Trp | Leu | Ser | Asp | Phe | Pro | Gln |
| | | | 20 | | | | | 25 | | | | | 30 | | |
| Ala | Trp | Ala | Glu | Thr | Gly | Gly | Met | Gly | Leu | Ala | Val | Arg | Gln | Ala | Pro |
| | | 35 | | | | | 40 | | | | | 45 | | | |
| Leu | Ile | Ile | Pro | Leu | Lys | Ala | Thr | Ser | Thr | Pro | Val | Ser | Ile | Lys | Gln |
| 50 | | | | | 55 | | | | | 60 | | | | | |
| Tyr | Pro | Met | Ser | Gln | Glu | Ala | Arg | Leu | Gly | Ile | Lys | Pro | His | Ile | Gln |
| 65 | | | | 70 | | | | | 75 | | | | | 80 | |
| Arg | Leu | Leu | Asp | Gln | Gly | Ile | Leu | Val | Pro | Cys | Gln | Ser | Pro | Trp | Asn |
| | | | | 85 | | | | | 90 | | | | | 95 | |
| Thr | Pro | Leu | Leu | Pro | Val | Lys | Lys | Pro | Gly | Thr | Asn | Asp | Tyr | Arg | Pro |
| | | | 100 | | | | | 105 | | | | | 110 | | |
| Val | Gln | Asp | Leu | Arg | Glu | Val | Asn | Lys | Arg | Val | Glu | Asp | Ile | His | Pro |
| | | 115 | | | | | 120 | | | | | 125 | | | |
| Thr | Val | Pro | Asn | Pro | Tyr | Asn | Leu | Leu | Ser | Gly | Leu | Pro | Pro | Ser | His |
| 130 | | | | | 135 | | | | | 140 | | | | | |
| Gln | Trp | Tyr | Thr | Val | Leu | Asp | Leu | Lys | Asp | Ala | Phe | Phe | Cys | Leu | Arg |
| 145 | | | | 150 | | | | | 155 | | | | | 160 | |
| Leu | His | Pro | Thr | Ser | Gln | Pro | Leu | Phe | Ala | Phe | Glu | Trp | Arg | Asp | Pro |
| | | | | 165 | | | | | 170 | | | | | 175 | |
| Glu | Met | Gly | Ile | Ser | Gly | Gln | Leu | Thr | Trp | Thr | Arg | Leu | Pro | Gln | Gly |
| | | | 180 | | | | | 185 | | | | | 190 | | |
| Phe | Lys | Asn | Ser | Pro | Thr | Leu | Phe | Asp | Glu | Ala | Leu | His | Arg | Asp | Leu |
| | | 195 | | | | | 200 | | | | | 205 | | | |
| Ala | Pro | Phe | Arg | Ala | Gln | His | Pro | Asp | Leu | Ile | Leu | Leu | Gln | Tyr | Val |
| | 210 | | | | | 215 | | | | | 220 | | | | |
| Asp | Asp | Leu | Leu | Leu | Ala | Ala | Thr | Ser | Glu | Leu | Asp | Cys | Gln | Gln | Gly |
| 225 | | | | | 230 | | | | | 235 | | | | | 240 |
| Thr | Arg | Ala | Leu | Leu | Gln | Thr | Leu | Gly | Asn | Leu | Gly | Tyr | Arg | Ala | Ser |
| | | | | 245 | | | | | 250 | | | | | 255 | |
| Ala | Lys | Lys | Ala | Gln | Ile | Cys | Gln | Lys | Gln | Val | Lys | Tyr | Leu | Gly | Tyr |
| | | | 260 | | | | | 265 | | | | | 270 | | |
| Leu | Leu | Lys | Glu | Gly | Gln | Arg | Trp | Leu | Thr | Glu | Ala | Arg | Lys | Glu | Thr |
| | | 275 | | | | | 280 | | | | | 285 | | | |
| Val | Met | Gly | Gln | Pro | Thr | Pro | Lys | Thr | Pro | Arg | Gln | Leu | Arg | Glu | Phe |
| | 290 | | | | | 295 | | | | | 300 | | | | |
| Leu | Gly | Thr | Ala | Gly | Phe | Cys | Arg | Leu | Trp | Ile | Pro | Gly | Phe | Ala | Glu |
| 305 | | | | | 310 | | | | | 315 | | | | | 320 |

Met Ala Ala Pro Leu Tyr Pro Leu Thr Lys Thr Gly Thr Leu Phe Asn
            325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
        370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
        450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile

<210> SEQ ID NO 52
<211> LENGTH: 673
<212> TYPE: PRT
<213> ORGANISM: Artificial Seuence
<220> FEATURE:
<223> OTHER INFORMATION: Reverse transcriptase variant C3+C5 amino acid
      sequence

<400> SEQUENCE: 52

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Pro Gly Ser Thr Pro Val Ser Ile Lys Gln
    50                  55                  60

Tyr Pro Met Ser Gln Glu Ala Arg Leu Gly Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Pro Phe Arg Ala Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
```

```
                420              425              430
Leu Val Ile Leu Ala Pro His Ala Val Glu Ala Leu Val Lys Gln Pro
            435              440              445

Pro Asp Arg Trp Leu Ser Asn Ala Arg Met Thr His Tyr Gln Ala Leu
450              455              460

Leu Leu Asp Thr Asp Arg Val Gln Phe Gly Pro Val Val Ala Leu Asn
465              470              475              480

Pro Ala Thr Leu Leu Pro Leu Pro Glu Glu Gly Leu Gln His Asn Cys
                485              490              495

Leu Asp Ile Leu Ala Glu Ala His Gly Thr Arg Pro Asp Leu Thr Asp
                500              505              510

Gln Pro Leu Pro Asp Ala Asp His Thr Trp Tyr Thr Asp Gly Ser Ser
            515              520              525

Leu Leu Gln Glu Gly Gln Arg Lys Ala Gly Ala Ala Val Thr Thr Glu
            530              535              540

Thr Glu Val Ile Trp Ala Lys Ala Leu Pro Ala Gly Thr Ser Ala Gln
545              550              555              560

Arg Ala Glu Leu Ile Ala Leu Thr Gln Ala Leu Lys Met Ala Glu Gly
                565              570              575

Lys Lys Leu Asn Val Tyr Thr Asp Ser Arg Tyr Ala Phe Ala Thr Ala
                580              585              590

His Ile His Gly Glu Ile Tyr Arg Arg Arg Gly Leu Leu Thr Ser Glu
            595              600              605

Gly Lys Glu Ile Lys Asn Lys Asp Glu Ile Leu Ala Leu Leu Lys Ala
            610              615              620

Leu Phe Leu Pro Lys Arg Leu Ser Ile Ile His Cys Pro Gly His Gln
625              630              635              640

Lys Gly His Ser Ala Glu Ala Arg Gly Asn Arg Met Ala Asp Gln Ala
                645              650              655

Ala Arg Lys Ala Ala Ile Thr Glu Thr Pro Asp Thr Ser Thr Leu Leu
            660              665              670

Ile

<210> SEQ ID NO 53
<211> LENGTH: 2019
<212> TYPE: DNA
<213> ORGANISM: Artificial Seuence
<220> FEATURE:
<223> OTHER INFORMATION: Reverse transcriptase variant C5(D209P+I212A)
      nucleic acid sequence

<400> SEQUENCE: 53
atgaccctaa atatagaaga tgagcatcgg ctacatgaga cctcaaaaga gccagatgtt      60
tctctagggt ccacatggct gtctgatttt cctcaggcct gggcggaaac cggggggcatg    120 ggactggcag ttcgccaagc tcctctgatc atacctctga agcaacctc tacccccgtg     180 tccataaaac aataccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
aagcgggtgg aagacatcca ccccaccgtg cccaacccct caacctcttg agcgggctc     420 ccaccgtccc accagtggta cactgtgctt gatttaaagg atgcctttt ctgcctgaga     480 ctccacccca ccagtcagcc tctcttcgcc tttgagtgga gagatccaga gatgggaatc    540
tcaggacaat tgacctggac cagactccca cagggtttca aaaacagtcc caccctgttt    600
```

```
gatgaggcac tgcacagaga cctagcaccg ttccgggctc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaaagaggg tcagagatgg    840
ctgactgagg ccagaaaaga gactgtgatg gggcagccta ctccgaagac ccctcgacaa    900
ctaagggagt cctagggac ggcaggcttc tgtcgcctct ggatccctgg gtttgcagaa    960
atggcagccc ccttgtaccc tctcaccaaa acggggactc tgtttaattg gggcccagac   1020
caacaaaagg cctatcaaga aatcaagcaa gctcttctaa ctgccccagc cctgggttg    1080 ccagatttga ctaagcccct tgaactcttt gtcgacgaga agcagggcta cgccaaaggt   1140
gtcctaacgc aaaaactggg accttggcgt cggccggtgg cctacctgtc aaaaagcta    1200 gacccagtag cagctgggtg gccccccttgc ctacggatgg tagcagccat tgccgtactg   1260
acaaaggatg caggcaagct aaccatggga cagccactag tcattctggc cccccatgca   1320
gtagaggcac tagtcaaaca acccccgac cgctggcttt ccaacgcccg gatgactcac    1380
tatcaggcct tgcttttgga cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggatggaag cagtctctta caagagggac agcgtaaggc gggagctgcg   1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctctttct gcccaaagga cttagcataa tccattgtcc aggacatcaa   1920
aagggacaca gcgccgaggc tagaggcaac cggatggctg accaagcggc ccgaaaggca   1980
gccatcacag agactccaga cacctctacc ctcctcata                         2019

<210> SEQ ID NO 54
<211> LENGTH: 2019
<212> TYPE: DNA
<213> ORGANISM: Artificial Seuence
<220> FEATURE:
<223> OTHER INFORMATION: Reverse transcriptase variant C3+C5 nucleic
      acid sequence

<400> SEQUENCE: 54
atgaccctaa atatagaaga tgagcatcgg ctacatgaga cctcaaaaga gccagatgtt     60
tctctagggt ccacatggct gtctgatttt cctcaggcct gggcggaaac cggggggcatg   120 ggactggcag ttcgccaagc tcctctgatc atacctctga aaccgggctc tacccccgtg   180
tccataaaac aataccccat gtcacaagaa gccagactgg ggatcaagcc ccacatacag   240
agactgttgg accagggaat actggtaccc tgccagtccc cctggaacac gccctgcta    300 cccgttaaga aaccagggac taatgattat aggcctgtcc aggatctgag agaagtcaac   360
aagcgggtgg aagacatcca ccccaccgtg cccaacccctt acaacctctt gagcgggctc   420
ccaccgtccc accagtggta cactgtgctt gatttaaagg atgccttttt ctgcctgaga   480
ctccacccca ccagtcagcc tctcttcgcc tttgagtgga gagatccaga gatgggaatc   540
tcaggacaat tgacctggac cagactccca caggggtttca aaaacagtcc caccctgttt    600
```

```
gatgaggcac tgcacagaga cctagcaccg ttccgggctc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaaagaggg tcagagatgg    840
ctgactgagg ccagaaaaga gactgtgatg gggcagccta ctccgaagac ccctcgacaa    900
ctaagggagt tcctagggac ggcaggcttc tgtcgcctct ggatccctgg gtttgcagaa    960
atggcagccc ccttgtaccc tctcaccaaa acggggactc tgtttaattg ggcccagac    1020 caacaaaagg cctatcaaga aatcaagcaa gctcttctaa ctgccccagc cctggggttg    1080
ccagatttga ctaagcccct tgaactcttt gtcgacgaga agcagggcta cgccaaaggt    1140
gtcctaacgc aaaaactggg accttggcgt cggccggtgg cctacctgtc caaaaagcta    1200
gacccagtag cagctgggtg gccccctggc ctacggatgg tagcagccat tgccgtactg    1260
acaaaggatg caggcaagct aaccatggga cagccactag tcattctggc cccccatgca    1320
gtagaggcac tagtcaaaca accccccgac cgctggcttt ccaacgcccg gatgactcac    1380
tatcaggcct tgcttttgga cacggaccgg gtccagttcg gaccggtggt agccctgaac    1440
ccggctacgc tgctcccact gcctgaggaa gggctgcaac acaactgcct tgatatcctg    1500
gccgaagccc acggaacccg acccgaccta acgaccagc cgctcccaga cgccgaccac    1560
acctggtaca cggatggaag cagtctctta caagagggac agcgtaaggc gggagctgcg    1620
gtgaccaccg agaccgaggt aatctgggct aaagccctgc cagccgggac atccgctcag    1680
cgggctgaac tgatagcact cacccaggcc ctaaagatgg cagaaggtaa gaagctaaat    1740
gtttatactg atagccgtta tgcttttgct actgccccata tccatggaga aatatacaga    1800
aggcgtgggt tgctcacatc agaaggcaaa gagatcaaaa ataaagacga gatcttggcc    1860
ctactaaaag ccctctttct gcccaaaaga cttagcataa tccattgtcc aggacatcaa    1920
aagggacaca gcgccgaggc tagaggcaac cggatggctg accaagcggc ccgaaaggca    1980
gccatcacag agactccaga cacctctacc ctcctcata                           2019
```

<210> SEQ ID NO 55
<211> LENGTH: 673
<212> TYPE: PRT
<213> ORGANISM: Artificial Seuence
<220> FEATURE:
<223> OTHER INFORMATION: Reverse transcriptase mutant P12+D1 amino acid
      sequence

<400> SEQUENCE: 55

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Asp Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
```

-continued

```
            100                 105                 110
Val Gln Asp Leu Arg Glu Val Asn Lys Arg Val Glu Asp Ile His Pro
            115                 120                 125
Thr Val Pro Asn Pro Tyr Asn Leu Leu Ser Gly Leu Pro Pro Ser His
        130                 135                 140
Gln Trp Tyr Thr Val Leu Asp Leu Lys Asp Ala Phe Phe Cys Leu Arg
145                 150                 155                 160
Leu His Pro Thr Ser Gln Pro Leu Phe Ala Phe Glu Trp Arg Asp Pro
                165                 170                 175
Glu Met Gly Ile Ser Gly Gln Leu Thr Trp Thr Arg Leu Pro Gln Gly
            180                 185                 190
Phe Lys Asn Ser Pro Thr Leu Phe Asp Glu Ala Leu His Arg Asp Leu
        195                 200                 205
Ala Asp Phe Arg Ile Gln His Pro Asp Leu Ile Leu Leu Gln Tyr Val
    210                 215                 220
Asp Asp Leu Leu Leu Ala Ala Thr Ser Glu Leu Asp Cys Gln Gln Gly
225                 230                 235                 240
Thr Arg Ala Leu Leu Gln Thr Leu Gly Asn Leu Gly Tyr Arg Ala Ser
                245                 250                 255
Ala Lys Lys Ala Gln Ile Cys Gln Lys Gln Val Lys Tyr Leu Gly Tyr
            260                 265                 270
Leu Leu Lys Glu Gly Gln Arg Trp Leu Thr Glu Ala Arg Lys Glu Lys
        275                 280                 285
Val Met Gly Gln Pro Thr Pro Lys Thr Pro Arg Gln Leu Arg Glu Phe
    290                 295                 300
Leu Gly Thr Ala Gly Phe Cys Arg Leu Trp Ile Pro Gly Phe Ala Glu
305                 310                 315                 320
Met Ala Ala Pro Leu Tyr Pro Leu Thr Lys Thr Gly Thr Leu Phe Asn
                325                 330                 335
Trp Gly Pro Asp Gln Gln Lys Ala Tyr Gln Glu Ile Lys Gln Ala Leu
            340                 345                 350
Leu Thr Ala Pro Ala Leu Gly Leu Pro Asp Leu Thr Lys Pro Phe Glu
        355                 360                 365
Leu Phe Val Asp Glu Lys Gln Gly Tyr Ala Lys Gly Val Leu Thr Gln
    370                 375                 380
Lys Leu Gly Pro Trp Arg Arg Pro Val Ala Tyr Leu Ser Lys Lys Leu
385                 390                 395                 400
Asp Pro Val Ala Ala Gly Trp Pro Pro Cys Leu Arg Met Val Ala Ala
                405                 410                 415
Ile Ala Val Leu Thr Lys Asp Ala Gly Lys Leu Thr Met Gly Gln Pro
            420                 425                 430
Leu Val Ile Leu Ala Pro His Ala Val Glu Ala Leu Val Lys Gln Pro
        435                 440                 445
Pro Asp Arg Trp Leu Ser Asn Ala Arg Met Thr His Tyr Gln Ala Leu
    450                 455                 460
Leu Leu Asp Thr Asp Arg Val Gln Phe Gly Pro Val Val Ala Leu Asn
465                 470                 475                 480
Pro Ala Thr Leu Leu Pro Leu Pro Glu Glu Gly Leu Gln His Asn Cys
                485                 490                 495
Leu Asp Ile Leu Ala Glu Ala His Gly Thr Arg Pro Asp Leu Thr Asp
            500                 505                 510
Gln Pro Leu Pro Asp Ala Asp His Thr Trp Tyr Thr Asp Gly Ser Ser
        515                 520                 525
```

```
Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Gly Leu Leu Thr Ser Glu
            595                 600                 605

Gly Lys Glu Ile Lys Asn Lys Asp Glu Ile Leu Ala Leu Leu Lys Ala
        610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile
```

<210> SEQ ID NO 56
<211> LENGTH: 673
<212> TYPE: PRT
<213> ORGANISM: Artificial Seuence
<220> FEATURE:
<223> OTHER INFORMATION: Reverse transcriptase mutant P12+LT amino acid sequence

<400> SEQUENCE: 56

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Asp Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu Arg Arg Asp Leu
    195                 200                 205
```

```
Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Leu Gly Gln Pro Thr Pro Lys Thr Pro Arg Gln Leu Arg Glu Phe
290                 295                 300

Leu Gly Lys Ala Gly Asn Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
610                 615                 620
```

-continued

```
Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
        660                 665                 670

Ile

<210> SEQ ID NO 57
<211> LENGTH: 673
<212> TYPE: PRT
<213> ORGANISM: Artificial Seuence
<220> FEATURE:
<223> OTHER INFORMATION: Reverse transcriptase mutant P12+K1 amino acid
      sequence

<400> SEQUENCE: 57

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Asp Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Lys Pro Thr Pro Lys Thr Pro Arg Gln Leu Arg Glu Phe
    290                 295                 300
```

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
            325                 330                 335

Trp Gly Pro Asp Gln Gln Lys Ala Tyr Gln Glu Ile Lys Gln Ala Leu
        340                 345                 350

Leu Thr Ala Pro Ala Leu Gly Leu Pro Asp Leu Thr Lys Pro Phe Glu
    355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
        420                 425                 430

Leu Val Ile Leu Ala Pro His Ala Val Glu Ala Leu Val Lys Gln Pro
    435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
        500                 505                 510

Gln Pro Leu Pro Asp Ala Asp His Thr Trp Tyr Thr Asp Gly Ser Ser
    515                 520                 525

Leu Leu Gln Glu Gly Gln Arg Lys Ala Gly Ala Ala Val Thr Thr Glu
530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
        580                 585                 590

His Ile His Gly Glu Ile Tyr Arg Arg Gly Leu Leu Thr Ser Glu
    595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
            645                 650                 655

Ala Arg Lys Ala Ala Ile Thr Glu Thr Pro Asp Thr Ser Thr Leu Leu
        660                 665                 670

Ile

<210> SEQ ID NO 58
<211> LENGTH: 673
<212> TYPE: PRT
<213> ORGANISM: Artificial Seuence
<220> FEATURE:
<223> OTHER INFORMATION: Reverse transcriptase mutant P12+K2 amino acid
      sequence

<400> SEQUENCE: 58

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Asp Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala

```
                    405                 410                 415
Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asn Gly Ser Ser
                515                 520                 525

Leu Leu Gln Glu Gly Gln Arg Lys Ala Gly Ala Ala Val Thr Thr Glu
                530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
                610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile

<210> SEQ ID NO 59
<211> LENGTH: 673
<212> TYPE: PRT
<213> ORGANISM: Artificial Seuence
<220> FEATURE:
<223> OTHER INFORMATION: Reverse transcriptase mutant P12+K3 amino acid
      sequence

<400> SEQUENCE: 59

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Asp Ser Thr Pro Val Ser Ile Lys Gln
            50                  55                  60

Tyr Pro Met Ser Gln Glu Ala Arg Leu Gly Ile Lys Pro His Ile Gln
65              70                  75                  80

Arg Leu Leu Asp Gln Gly Ile Leu Val Pro Cys Gln Ser Pro Trp Asn
```

```
                    85                  90                  95
Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
                115                 120                 125

Thr Val Pro Asn Pro Tyr Asn Leu Leu Ser Gly Leu Pro Pro Ser His
            130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
                195                 200                 205

Ala Asp Phe Arg Ile Gln His Pro Asp Leu Ile Leu Leu Gln Tyr Val
            210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Gln Pro Thr Pro Lys Thr Pro Arg Gln Leu Arg Glu Phe
290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
            370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510
```

```
Gln Pro Leu Pro Asp Ala Asp His Thr Trp Tyr Thr Ala Gly Ser Ser
            515                 520                 525

Leu Leu Gln Glu Gly Gln Arg Lys Ala Gly Ala Ala Val Thr Thr Glu
        530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Gly Leu Leu Thr Ser Glu
        595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile

<210> SEQ ID NO 60
<211> LENGTH: 673
<212> TYPE: PRT
<213> ORGANISM: Artificial Seuence
<220> FEATURE:
<223> OTHER INFORMATION: Reverse transcriptase mutant P12+K4 amino acid
      sequence

<400> SEQUENCE: 60

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Asp Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190
```

```
Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
210                 215                 220

Asp Asp Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285

Val Met Gly Gln Pro Thr Pro Lys Thr Pro Arg Gln Leu Arg Glu Phe
290                 295                 300

Leu Gly Lys Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
                370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
                450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
                515                 520                 525

Leu Leu Gln Glu Gly Gln Arg Lys Ala Gly Ala Ala Val Thr Thr Glu
                530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Arg Gly Leu Leu Thr Ser Glu
                595                 600                 605
```

```
Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile

<210> SEQ ID NO 61
<211> LENGTH: 673
<212> TYPE: PRT
<213> ORGANISM: Artificial Seuence
<220> FEATURE:
<223> OTHER INFORMATION: Reverse transcriptase mutant O1+C5 amino acid
      sequence

<400> SEQUENCE: 61

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Gly Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asp Glu Ala Leu His Arg Asp Leu
            195                 200                 205

Ala Pro Phe Arg Ala Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Glu Ala Arg Lys Glu Thr
                275                 280                 285
```

Val Met Gly Gln Pro Thr Pro Lys Thr Pro Arg Gln Leu Arg Glu Phe
290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Lys Ala Tyr Gln Glu Ile Lys Gln Ala Leu
                340                 345                 350

Leu Thr Ala Pro Ala Leu Gly Leu Pro Asp Leu Thr Lys Pro Phe Glu
                355                 360                 365

Leu Phe Val Asp Glu Lys Gln Gly Tyr Ala Lys Gly Val Leu Thr Gln
370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
                420                 425                 430

Leu Val Ile Leu Ala Pro His Ala Val Glu Ala Leu Val Lys Gln Pro
                435                 440                 445

Pro Asp Arg Trp Leu Ser Asn Ala Arg Met Thr His Tyr Gln Ala Leu
450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
                500                 505                 510

Gln Pro Leu Pro Asp Ala Asp His Thr Trp Tyr Thr Asp Gly Ser Ser
                515                 520                 525

Leu Leu Gln Glu Gly Gln Arg Lys Ala Gly Ala Ala Val Thr Thr Glu
                530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
                580                 585                 590

His Ile His Gly Glu Ile Tyr Arg Arg Arg Gly Leu Leu Thr Ser Glu
                595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
                660                 665                 670

Ile

<210> SEQ ID NO 62
<211> LENGTH: 673
<212> TYPE: PRT
<213> ORGANISM: Artificial Seuence
<220> FEATURE:
<223> OTHER INFORMATION: Reverse transcriptase mutant P12+C5 amino acid sequence

<400> SEQUENCE: 62

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Asp Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Pro Phe Arg Ala Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
```

```
                385           390           395           400
Asp Pro Val Ala Ala Gly Trp Pro Pro Cys Leu Arg Met Val Ala Ala
                    405               410               415
Ile Ala Val Leu Thr Lys Asp Ala Gly Lys Leu Thr Met Gly Gln Pro
                420               425               430
Leu Val Ile Leu Ala Pro His Ala Val Glu Ala Leu Val Lys Gln Pro
                435               440               445
Pro Asp Arg Trp Leu Ser Asn Ala Arg Met Thr His Tyr Gln Ala Leu
            450               455               460
Leu Leu Asp Thr Asp Arg Val Gln Phe Gly Pro Val Val Ala Leu Asn
465             470               475               480
Pro Ala Thr Leu Leu Pro Leu Glu Glu Gly Leu Gln His Asn Cys
                485               490               495
Leu Asp Ile Leu Ala Glu Ala His Gly Thr Arg Pro Asp Leu Thr Asp
                500               505               510
Gln Pro Leu Pro Asp Ala Asp His Thr Trp Tyr Thr Asp Gly Ser Ser
                515               520               525
Leu Leu Gln Glu Gly Gln Arg Lys Ala Gly Ala Ala Val Thr Thr Glu
                530               535               540
Thr Glu Val Ile Trp Ala Lys Ala Leu Pro Ala Gly Thr Ser Ala Gln
545                 550               555               560
Arg Ala Glu Leu Ile Ala Leu Thr Gln Ala Leu Lys Met Ala Glu Gly
                    565               570               575
Lys Lys Leu Asn Val Tyr Thr Asp Ser Arg Tyr Ala Phe Ala Thr Ala
                580               585               590
His Ile His Gly Glu Ile Tyr Arg Arg Arg Gly Leu Leu Thr Ser Glu
                595               600               605
Gly Lys Glu Ile Lys Asn Lys Asp Glu Ile Leu Ala Leu Leu Lys Ala
                610               615               620
Leu Phe Leu Pro Lys Arg Leu Ser Ile Ile His Cys Pro Gly His Gln
625             630               635               640
Lys Gly His Ser Ala Glu Ala Arg Gly Asn Arg Met Ala Asp Gln Ala
                    645               650               655
Ala Arg Lys Ala Ala Ile Thr Glu Thr Pro Asp Thr Ser Thr Leu Leu
                660               665               670
Ile

<210> SEQ ID NO 63
<211> LENGTH: 2019
<212> TYPE: DNA
<213> ORGANISM: Artificial Seuence
<220> FEATURE:
<223> OTHER INFORMATION: Reverse transcriptase mutant P12+D1 nucleic
      acid sequence

<400> SEQUENCE: 63
atgaccctaa atatagaaga tgagcatcgg ctacatgaga cctcaaaaga gccagatgtt      60
tctctagggt ccacatggct gtctgatttt cctcaggcct gggcggaaac cggggggcatg    120 ggactggcag ttcgccaagc tcctctgatc atacctctga agcagactc taccccgtg       180 tccataaaac aatacccct gtcacaagaa gccagactgg ggatcaagcc ccacatacag     240
agactgttgg accagggaat actggtaccc tgccagtccc cctggaacac gcccctgcta    300
cccgttaaga aaccagggac taatgattat aggcctgtcc aggatctgag agaagtcaac    360
aagcgggtgg aagacatcca ccccaccgtg cccaacccctt acaacctctt gagcgggctc   420
```

```
ccaccgtccc accagtggta cactgtgctt gatttaaagg atgcctttt  ctgcctgaga    480 ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaagagggt cagagatgg     840 ctgactgagg ccagaaaaga gaaagtgatg gggcagccta ctccgaagac ccctcgacaa    900
ctaagggagt tcctagggac ggcaggcttc tgtcgcctct ggatccctgg gtttgcagaa    960
atggcagccc ccttgtaccc tctcaccaaa acggggactc tgtttaattg ggcccagac    1020 caacaaaagg cctatcaaga aatcaagcaa gctcttctaa ctgccccagc cctggggttg   1080
ccagatttga ctaagccctt tgaactcttt gtcgacgaga agcagggcta cgccaaaggt   1140
gtcctaacgc aaaaactggg accttggcgt cggccggtgg cctacctgtc caaaaagcta   1200
gacccagtag cagctgggtg gccccccttgc ctacggatgg tagcagccat tgccgtactg   1260
acaaaggatg caggcaagct aaccatggga cagccactag tcattctggc ccccatgca   1320 gtagaggcac tagtcaaaca ccccccgac cgctggcttt ccaacgcccg gatgactcac   1380
tatcaggcct tgcttttgga cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggatggaag cagtctctta caagagggac agcgtaaggc gggagctgcg   1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740 gttttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctcttct gcccaaaaga cttagcataa tccattgtcc aggacatcaa   1920
aagggacaca cgccgaggc tagaggcaac cggatggctg accaagcggc ccgaaaggca   1980
gccatcacag agactccaga cacctctacc ctcctcata                           2019
```

<210> SEQ ID NO 64
<211> LENGTH: 2019
<212> TYPE: DNA
<213> ORGANISM: Artificial Seuence
<220> FEATURE:
<223> OTHER INFORMATION: Reverse transcriptase mutant P12+LT nucleic
      acid sequence

<400> SEQUENCE: 64

```
atgaccctaa atatagaaga tgagcatcgg ctacatgaga cctcaaaaga gccagatgtt     60
tctctagggt ccacatggct gtctgatttt cctcaggcct gggcggaaac cgggggcatg    120
ggactggcag ttcgccaagc tcctctgatc atacctctga agcagactc taccccgtg     180 tccataaaac aataccccat gtcacaagaa gccagactgg ggatcaagcc ccacatacag    240
agactgttgg accagggaat actggtaccc tgccagtccc cctggaacac gccctgcta    300 cccgttaaga accagggac taatgattat aggcctgtcc aggatctgag agaagtcaac    360
aagcgggtgg aagacatcca ccccaccgtg cccaaccctt acaacctctt gagcgggctc    420
```

```
ccaccgtccc accagtggta cactgtgctt gatttaaagg atgcctttt     ctgcctgaga    480 ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcgcagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaaagaggg tcagagatgg    840
ctgactgagg ccagaaaaga gactgtgctg ggcagccta ctccgaagac ccctcgacaa    900
ctaagggagt tcctagggaa agcaggcaac tgtcgcctct ggatccctgg gtttgcagaa    960
atggcagccc ccttgtaccc tctcaccaaa acggggactc tgtttaattg gggcccagac    1020
caacaaaagg cctatcaaga aatcaagcaa gctcttctaa ctgccccagc cctggggttg    1080
ccagatttga ctaagccctt tgaactcttt gtcgacgaga agcagggcta cgccaaaggt    1140
gtcctaacgc aaaaactggg accttggcgt cggccggtgg cctacctgtc caaaaagcta    1200
gacccagtag cagctgggtg gccccttgc ctacggatgg tagcagccat tgccgtactg    1260
acaaaggatg caggcaagct aaccatggga cagccactag tcattctggc ccccatgca    1320 gtagaggcac tagtcaaaca accccccgac cgctggcttt ccaacgcccg gatgactcac    1380
tatcaggcct tgctttgga cacggaccgg gtccagttcg gaccggtggt agccctgaac    1440
ccggctacgc tgctcccact gcctgaggaa gggctgcaac acaactgcct tgatatcctg    1500
gccgaagccc acggaacccg acccgaccta acggaccagc cgctcccaga cgccgaccac    1560
acctggtaca cggatggaag cagtctctta caagagggac agcgtaaggc gggagctgcg    1620
gtgaccaccg agaccgaggt aatctgggct aaagccctgc cagccgggac atccgctcag    1680
cgggctgaac tgatagcact cacccaggcc ctaaagatgg cagaaggtaa gaagctaaat    1740
gtttatactg atagccgtta tgcttttgct actgcccata tccatggaga aatatacaga    1800
aggcgtgggt tgctcacatc agaaggcaaa gagatcaaaa ataaagacga gatcttggcc    1860
ctactaaaag ccctctttct gcccaaaaga cttagcataa tccattgtcc aggacatcaa    1920
aagggacaca gcgccgaggc tagaggcaac cggatggctg accaagcggc ccgaaaggca    1980
gccatcacag agactccaga cacctctacc ctcctcata                           2019
```

<210> SEQ ID NO 65
<211> LENGTH: 2019
<212> TYPE: DNA
<213> ORGANISM: Artificial Seuence
<220> FEATURE:
<223> OTHER INFORMATION: Reverse transcriptase mutant P12+K1 nucleic acid sequence

<400> SEQUENCE: 65

```
atgaccctaa atatagaaga tgagcatcgg ctacatgaga cctcaaaaga gccagatgtt    60
tctctagggt ccacatggct gtctgatttt cctcaggcct gggcggaaac cggggggcatg    120 ggactggcag ttcgccaagc tcctctgatc atacctctga agcagactc tacccccgtg    180 tccataaaac aataccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
aagcgggtgg aagacatcca ccccaccgtg cccaacccttacaacctctt gagcgggctc    420
```

```
ccaccgtccc accagtggta cactgtgctt gatttaaagg atgccttttt ctgcctgaga      480
ctccacccca ccagtcagcc tctcttcgcc tttgagtgga gagatccaga gatgggaatc      540
tcaggacaat tgacctggac cagactccca cagggtttca aaaacagtcc caccctgttt      600
gatgaggcac tgcacagaga cctagcagac ttccggatcc agcacccaga cttgatcctg      660
ctacagtacg tggatgactt actgctggcc gccacttctg agctagactg ccaacaaggt      720
actcgggccc tgttacaaac cctagggaac ctcgggtatc gggcctcggc caagaaagcc      780
caaatttgcc agaaacaggt caagtatctg gggtatcttc taaaagaggg tcagagatgg      840
ctgactgagg ccagaaaaga gactgtgatg gggaaaccta ctccgaagac ccctcgacaa      900
ctaagggagt tcctagggac ggcaggcttc tgtcgcctct ggatccctgg gtttgcagaa      960
atggcagccc ccttgtaccc tctcaccaaa acggggactc tgtttaattg ggcccagac     1020 caacaaaagg cctatcaaga aatcaagcaa gctcttctaa ctgccccagc cctggggttg     1080
ccagatttga ctaagccctt tgaactcttt gtcgacgaga agcagggcta cgccaaaggt     1140
gtcctaacgc aaaaactggg accttggcgt cggccggtgg cctacctgtc caaaaagcta     1200
gacccagtag cagctgggtg gccccccttgc ctacggatgg tagcagccat tgccgtactg     1260
acaaaggatg caggcaagct aaccatggga cagccactag tcattctggc cccccatgca     1320
gtagaggcac tagtcaaaca ccccccgac cgctggcttt ccaacgcccg gatgactcac     1380
tatcaggcct tgcttttgga cacggaccgg gtccagttcg gaccggtggt agccctgaac     1440
ccggctacgc tgctcccact gcctgaggaa gggctgcaac acaactgcct tgatatcctg     1500
gccgaagccc acggaacccg acccgaccta acggaccagc cgctcccaga cgccgaccac     1560
acctggtaca cggatggaag cagtctctta caagagggac agcgtaaggc gggagctgcg     1620
gtgaccaccg agaccgaggt aatctgggct aaagccctgc cagccgggac atccgctcag     1680
cgggctgaac tgatagcact cacccaggcc ctaaagatgg cagaaggtaa gaagctaaat     1740
gtttatactg atagccgtta tgcttttgct actgcccata tccatggaga aatatacaga     1800
aggcgtgggt tgctcacatc agaaggcaaa gagatcaaaa ataaagacga gatcttggcc     1860
ctactaaaag ccctctttct gcccaaaaga cttagcataa tccattgtcc aggacatcaa     1920
aagggacaca cgcgccgaggc tagaggcaac cggatggctg accaagcggc ccgaaaggca     1980
gccatcacag agactccaga cacctctacc ctcctcata                             2019
```

<210> SEQ ID NO 66
<211> LENGTH: 2019
<212> TYPE: DNA
<213> ORGANISM: Artificial Seuence
<220> FEATURE:
<223> OTHER INFORMATION: Reverse transcriptase mutant P12+K2 nucleic
      acid sequence

<400> SEQUENCE: 66

```
atgaccctaa atatagaaga tgagcatcgg ctacatgaga cctcaaaaga gccagatgtt       60
tctctagggt ccacatggct gtctgatttt cctcaggcct gggcggaaac cggggggcatg    120 ggactggcag ttcgccaagc tcctctgatc atacctctga agcagactc taccccccgtg    180 tccataaaac aataccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac    360
aagcgggtgg aagacatcca ccccaccgtg cccaacccct acaacctctt gagcgggctc    420
```

```
ccaccgtccc accagtggta cactgtgctt gatttaaagg atgccttttt ctgcctgaga      480
ctccacccca ccagtcagcc tctcttcgcc tttgagtgga gagatccaga gatgggaatc      540
tcaggacaat tgacctggac cagactccca cagggtttca aaaacagtcc caccctgttt      600
gatgaggcac tgcacagaga cctagcagac ttccggatcc agcacccaga cttgatcctg      660
ctacagtacg tggatgactt actgctggcc gccacttctg agctagactg ccaacaaggt      720
actcgggccc tgttacaaac cctagggaac ctcgggtatc gggcctcggc caagaaagcc      780
caaatttgcc agaaacaggt caagtatctg gggtatcttc taaaagaggg tcagagatgg      840
ctgactgagg ccagaaaaga gactgtgatg ggcagccta ctccgaagac ccctcgacaa       900
ctaagggagt tcctagggac ggcaggcttc tgtcgcctct ggatccctgg gtttgcagaa      960
atggcagccc ccttgtaccc tctcaccaaa acggggactc tgtttaattg gggcccagac     1020
caacaaaagg cctatcaaga aatcaagcaa gctcttctaa ctgccccagc cctggggttg     1080
ccagatttga ctaagccctt tgaactcttt gtcgacgaga agcagggcta cgccaaaggt     1140
gtcctaacgc aaaaactggg accttggcgt cggccggtgg cctacctgtc caaaaagcta     1200
gacccagtag cagctgggtg gccccttgc ctacggatgg tagcagccat tgccgtactg      1260
acaaaggatg caggcaagct aaccatggga cagccactag tcattctggc ccccatgca     1320 gtagaggcac tagtcaaaca accccccgac cgctggcttt ccaacgcccg gatgactcac     1380
tatcaggcct tgcttttgga cacggaccgg gtccagttcg gaccggtggt agccctgaac     1440
ccggctacgc tgctcccact gcctgaggaa gggctgcaac acaactgcct tgatatcctg     1500
gccgaagccc acggaacccg acccgaccta acggaccagc cgctcccaga cgccgaccac     1560
acctggtaca cgaacggaag cagtctctta caagagggac agcgtaaggc gggagctgcg     1620
gtgaccaccg agaccgaggt aatctgggct aaagccctgc cagccgggac atccgctcag     1680
cgggctgaac tgatagcact cacccaggcc ctaaagatgg cagaaggtaa gaagctaaat     1740
gtttatactg atagccgtta tgcttttgct actgcccata tccatggaga aatatacaga     1800
aggcgtgggt tgctcacatc agaaggcaaa gagatcaaaa ataaagacga gatcttggcc     1860
ctactaaaag ccctctttct gcccaaaaga cttagcataa tccattgtcc aggacatcaa     1920
aagggacaca cgcgccgaggc tagaggcaac cggatggctg accaagcggc ccgaaaggca     1980
gccatcacag agactccaga cacctctacc ctcctcata                             2019
```

<210> SEQ ID NO 67
<211> LENGTH: 2019
<212> TYPE: DNA
<213> ORGANISM: Artificial Seuence
<220> FEATURE:
<223> OTHER INFORMATION: Reverse transcriptase mutant P12+K3 nucleic
      acid sequence

<400> SEQUENCE: 67

```
atgaccctaa atatagaaga tgagcatcgg ctacatgaga cctcaaaaga gccagatgtt       60
tctctagggt ccacatggct gtctgatttt cctcaggcct gggcggaaac cggggggcatg    120 ggactggcag ttcgccaagc tcctctgatc atacctctga aagcagactc taccccgtg      180 tccataaaac aataccccat gtcacaagaa gccagactgg ggatcaagcc ccacatacag     240
agactgttgg accagggaat actggtaccc tgccagtccc cctggaacac gcccctgcta     300
cccgttaaga aaccagggac taatgattat aggcctgtcc aggatctgag agaagtcaac     360
aagcgggtgg aagacatcca ccccaccgtg cccaacccct tacaacctct tgagcgggctc    420
```

```
ccaccgtccc accagtggta cactgtgctt gatttaaagg atgcctttt    480
                                          ctgcctgaga ctccacccca ccagtcagcc tctcttcgcc tttgagtgga gagatccaga   540
                                          gatgggaatc tcaggacaat tgacctggac cagactccca cagggtttca aaaacagtcc   600
                                          caccctgttt gatgaggcac tgcacagaga cctagcagac ttccggatcc agcacccaga   660
                                          cttgatcctg ctacagtacg tggatgactt actgctggcc gccacttctg agctagactg   720
                                          ccaacaaggt actcgggccc tgttacaaac cctagggaac ctcgggtatc gggcctcggc   780
                                          caagaaagcc caaatttgcc agaaacaggt caagtatctg gggtatcttc taaagagggg   840
                                          tcagagatgg ctgactgagg ccagaaaaga gactgtgatg gggcagccta ctccgaagac   900
                                          ccctcgacaa ctaagggagt tcctagggac ggcaggcttc tgtcgcctct ggatccctgg   960
                                          gtttgcagaa atggcagccc ccttgtaccc tctcaccaaa acgggactg tgtttaattg    1020
                                          gggcccagac caacaaaagg cctatcaaga aatcaagcaa gctcttctaa ctgccccagc   1080
                                          cctggggttg ccagatttga ctaagccctt tgaactcttt gtcgacgaga agcagggcta   1140
                                          cgccaaaggt gtcctaacgc aaaaactggg accttggcgt cggccggtgg cctacctgtc   1200
                                          caaaaagcta gacccagtag cagctgggtg gccccttgc ctacggatgg tagcagccat    1260
                                          tgccgtactg acaaaggatg caggcaagct aaccatggga cagccactag tcattctggc   1320
                                          cccccatgca gtagaggcac tagtcaaaca accccccgac cgctggcttt ccaacgcccg   1380
                                          atgactcac tatcaggcct gcttttgga cacggaccgg gtccagttcg gaccggtggt    1440
                                          agccctgaac ccggctacgc tgctcccact gcctgaggaa gggctgcaac acaactgcct   1500
                                          tgatatcctg gccgaagccc acggaacccg acccgaccta acggaccagc cgctcccaga   1560
                                          cgccgaccac acctggtaca cggctggaag cagtctctta caagagggac agcgtaaggc   1620
                                          gggagctgcg gtgaccaccg agaccgaggt aatctgggct aaagccctgc cagccgggac   1680
                                          atccgctcag cgggctgaac tgatagcact cacccaggcc ctaaagatgg cagaaggtaa   1740
                                          gaagctaaat gtttatactg atagccgtta tgcttttgct actgcccata tccatggaga   1800
                                          aatatacaga aggcgtgggt tgctcacatc agaaggcaaa gagatcaaaa ataaagacga   1860
                                          gatcttggcc ctactaaaag ccctctttct gcccaaaaga cttagcataa tccattgtcc   1920
                                          aggacatcaa aagggacaca cgcgccgaggc tagaggcaac cggatggctg accaagcggc   1980
                                          ccgaaaggca gccatcacag agactccaga cacctctacc ctcctcata              2019
```

<210> SEQ ID NO 68
<211> LENGTH: 2019
<212> TYPE: DNA
<213> ORGANISM: Artificial Seuence
<220> FEATURE:
<223> OTHER INFORMATION: Reverse transcriptase mutant P12+K4 nucleic
      acid sequence

<400> SEQUENCE: 68

```
atgaccctaa atatagaaga tgagcatcgg ctacatgaga cctcaaaaga   60
                                          gccagatgtt tctctagggt ccacatggct gtctgatttt cctcaggcct gggcggaaac   120
                                          cggggggcatg ggactggcag ttcgccaagc tcctctgatc atacctctga agcagactc    180
                                          taccccgtg tccataaaac aataccccat gtcacaagaa gccagactgg ggatcaagcc   240
                                          cacatacag agactgttgg accagggaat actggtaccc tgccagtccc cctggaacac   300
                                          gccctgcta cccgttaaga aaccagggac taatgattat aggcctgtcc aggatctgag   360
                                          agaagtcaac aagcgggtgg aagacatcca ccccaccgtg cccaaccctt acaacctctt   420
                                          gagcgggctc
```

```
ccaccgtccc accagtggta cactgtgctt gatttaaagg atgccttttt ctgcctgaga    480
ctccacccca ccagtcagcc tctcttcgcc tttgagtgga gagatccaga gatgggaatc    540
tcaggacaat tgacctggac cagactccca cagggtttca aaaacagtcc caccctgttt    600
gatgaggcac tgcacagaga cctagcagac ttccggatcc agcacccaga cttgatcctg    660
ctacagtacg tggatgactt actgctggcc gccacttctg agctagactg ccaacaaggt    720
actcgggccc tgttacaaac cctagggaac ctcgggtatc gggcctcggc caagaaagcc    780
caaatttgcc agaaacaggt caagtatctg gggtatcttc taaagagggt cagagatgg     840 ctgactgagg ccagaaaaga gactgtgatg gggcagccta ctccgaagac ccctcgacaa    900
ctaagggagt tcctagggaa gcaggcttc tgtcgcctct ggatccctgg gtttgcagaa     960
atggcagccc ccttgtaccc tctcaccaaa acggggactg tgtttaattg gggcccagac   1020
caacaaaagg cctatcaaga aatcaagcaa gctcttctaa ctgccccagc cctggggttg   1080
ccagatttga ctaagccctt tgaactcttt gtcgacgaga gcagggcta cgccaaaggt    1140 gtcctaacgc aaaaactggg accttggcgt cggccggtgg cctacctgtc caaaaagcta   1200
gacccagtag cagctgggtg gccccttgc ctacggatgg tagcagccat tgccgtactg    1260
acaaaggatg caggcaagct aaccatggga cagccactag tcattctggc cccccatgca   1320
gtagaggcac tagtcaaaca ccccccgac cgctggcttt ccaacgcccg gatgactcac    1380
tatcaggcct tgcttttgga cacggaccgg gtccagttcg gaccggtggt agccctgaac   1440
ccggctacgc tgctcccact gcctgaggaa gggctgcaac acaactgcct tgatatcctg   1500
gccgaagccc acggaacccg acccgaccta acggaccagc cgctcccaga cgccgaccac   1560
acctggtaca cggatggaag cagtctctta caagagggac agcgtaaggc gggagctgcg   1620
gtgaccaccg agaccgaggt aatctgggct aaagccctgc cagccgggac atccgctcag   1680
cgggctgaac tgatagcact cacccaggcc ctaaagatgg cagaaggtaa gaagctaaat   1740
gtttatactg atagccgtta tgcttttgct actgcccata tccatggaga aatatacaga   1800
aggcgtgggt tgctcacatc agaaggcaaa gagatcaaaa ataaagacga gatcttggcc   1860
ctactaaaag ccctcttct gcccaaaaga cttagcataa tccattgtcc aggacatcaa   1920
aagggacaca cgcgccgaggc tagaggcaac cggatggctg accaagcggc ccgaaaggca   1980
gccatcacag agactccaga cacctctacc ctcctcata                          2019
```

<210> SEQ ID NO 69
<211> LENGTH: 2019
<212> TYPE: DNA
<213> ORGANISM: Artificial Seuence
<220> FEATURE:
<223> OTHER INFORMATION: Reverse transcriptase mutant O1+C5 nucleic acid
     sequence

<400> SEQUENCE: 69

```
atgaccctaa atatagaaga tgagcatcgg ctacatgaga cctcaaaaga gccagatgtt     60
tctctagggt ccacatggct gtctgatttt cctcaggcct gggcggaaac cggggggcatg   120 ggactggcag ttcgccaagc tcctctgatc atacctctga aagcaggttc tacccccgtg   180
tccataaaac aataccccat gtcacaagaa gccagactgg ggatcaagcc ccacatacag   240
agactgttgg accagggaat actggtaccc tgccagtccc cctggaacac gcccctgcta   300
cccgttaaga aaccagggac taatgattat aggcctgtcc aggatctgag agaagtcaac   360
aagcgggtgg aagacatcca ccccaccgtg cccaacccttt acaacctctt gagcgggctc   420
```

```
ccaccgtccc accagtggta cactgtgctt gatttaaagg atgccttttt ctgcctgaga      480
ctccacccca ccagtcagcc tctcttcgcc tttgagtgga gagatccaga gatgggaatc      540
tcaggacaat tgacctggac cagactccca cagggtttca aaacagtcc  cacc ctgttt     600 gatgaggcac tgcacagaga cctagcaccg ttccgggctc agcacccaga cttgatcctg      660
ctacagtacg tggatgactt actgctggcc gccacttctg agctagactg ccaacaaggt      720
actcgggccc tgttacaaac cctagggaac ctcgggtatc gggcctcggc caagaaagcc      780
caaatttgcc agaaacaggt caagtatctg gggtatcttc taaagagggt cagagatggg     840
ctgactgagg ccagaaaaga gactgtgatg gggcagccta ctccgaagac ccctcgacaa      900
ctaagggagt tcctagggac ggcaggcttc tgtcgcctct ggatccctgg gtttgcagaa      960
atggcagccc ccttgtaccc tctcaccaaa acgggactg  tgtttaattg gggcccagac     1020
caacaaaagg cctatcaaga aatcaagcaa gctcttctaa ctgccccagc cctggggttg     1080
ccagatttga ctaagccctt tgaactcttt gtcgacgaga agcagggcta cgccaaaggt     1140
gtcctaacgc aaaaactggg accttggcgt cggccggtgg cctacctgtc caaaaagcta     1200
gacccagtag cagctgggtg gccccccttgc ctacggatgg tagcagccat tgccgtactg    1260
acaaaggatg caggcaagct aaccatggga cagccactag tcattctggc cccccatgca     1320
gtagaggcac tagtcaaaca acccccgac  cgctggcttt ccaacgcccg gatgactcac     1380
tatcaggcct tgcttttgga cacggaccgg gtccagttcg gaccggtggt agccctgaac    1440
ccggctacgc tgctcccact gcctgaggaa gggctgcaac acaactgcct tgatatcctg    1500
gccgaagccc acggaacccg acccgaccta acggaccagc cgctcccaga cgccgaccac    1560
acctggtaca cggatggaag cagtctctta caagagggac agcgtaaggc gggagctgcg    1620
gtgaccaccg agaccgaggt aatctgggct aaagccctgc cagccgggac atccgctcag    1680
cgggctgaac tgatagcact cacccaggcc ctaaagatgg cagaaggtaa gaagctaaat    1740
gtttatactg atagccgtta tgcttttgct actgcccata tccatggaga aatatacaga    1800
aggcgtgggt tgctcacatc agaaggcaaa gagatcaaaa ataaagacga gatcttggcc    1860
ctactaaaag ccctctttct gcccaaaaga cttagcataa tccattgtcc aggacatcaa    1920
aagggacaca cgcgccgaggc tagaggcaac cggatggctg accaagcggc ccgaaaggca    1980
gccatcacag agactccaga cacctctacc ctcctcata                           2019
```

<210> SEQ ID NO 70
<211> LENGTH: 2019
<212> TYPE: DNA
<213> ORGANISM: Artificial Seuence
<220> FEATURE:
<223> OTHER INFORMATION: Reverse transcriptase mutant P12+C5 nucleic acid sequence

<400> SEQUENCE: 70

```
atgaccctaa atatagaaga tgagcatcgg ctacatgaga cctcaaaaga gccagatgtt       60
tctctagggt ccacatggct gtctgatttt cctcaggcct gggcggaaac cggggggcatg    120 ggactggcag ttcgccaagc tcctctgatc atacctctga agcaggttc  tacccccgtg     180 tccataaaac aataccccat gtcacaagaa gccagactgg ggatcaagcc ccacatacag    240
agactgttgg accagggaat actggtaccc tgccagtccc cctggaacac gcccctgcta    300
cccgttaaga aaccagggac taatgattat aggcctgtcc aggatctgag agaagtcaac     360
aagcgggtgg aagacatcca ccccaccgtg cccaaccctt acaacctctt gagcgggctc     420
```

-continued

```
ccaccgtccc accagtggta cactgtgctt gatttaaagg atgccttttt ctgcctgaga      480
ctccacccca ccagtcagcc tctcttcgcc tttgagtgga gagatccaga gatgggaatc      540
tcaggacaat tgacctggac cagactccca cagggtttca aaaacagtcc caccctgttt      600
gatgaggcac tgcacagaga cctagcaccg ttccgggctc agcacccaga cttgatcctg      660
ctacagtacg tggatgactt actgctggcc gccacttctg agctagactg ccaacaaggt      720
actcgggccc tgttacaaac cctagggaac ctcgggtatc gggcctcggc caagaaagcc      780
caaatttgcc agaaacaggt caagtatctg gggtatcttc taaaagaggg tcagagatgg      840
ctgactgagg ccagaaaaga gactgtgatg gggcagccta ctccgaagac ccctcgacaa      900
ctaagggagt tcctagggac ggcaggcttc tgtcgcctct ggatccctgg gtttgcagaa      960
atggcagccc ccttgtaccc tctcaccaaa acggggactc tgtttaattg gggcccagac     1020
caacaaaagg cctatcaaga aatcaagcaa gctcttctaa ctgccccagc cctggggttg     1080
ccagatttga ctaagccctt tgaactcttt gtcgacgaga agcagggcta cgccaaaggt     1140
gtcctaacgc aaaaactggg accttggcgt cggccggtgg cctacctgtc caaaaagcta     1200
gacccagtag cagctgggtg gccccttgc ctacggatgg tagcagccat tgccgtactg     1260
acaaaggatg caggcaagct aaccatggga cagccactag tcattctggc cccccatgca     1320
gtagaggcac tagtcaaaca accccccgac cgctggcttt ccaacgcccg gatgactcac     1380
tatcaggcct tgcttttgga cacggaccgg gtccagttcg gaccggtggt agccctgaac     1440
ccggctacgc tgctcccact gcctgaggaa gggctgcaac acaactgcct tgatatcctg     1500
gccgaagccc acggaacccg acccgaccta acggaccagc cgctcccaga cgccgaccac     1560
acctggtaca cggatggaag cagtctctta caagagggac agcgtaaggc gggagctgcg     1620
gtgaccaccg agaccgaggt aatctgggct aaagccctgc cagccgggac atccgctcag     1680
cgggctgaac tgatagcact cacccaggcc ctaaagatgg cagaaggtaa gaagctaaat     1740
gtttatactg atagccgtta tgcttttgct actgcccata tccatggaga aatatacaga     1800
aggcgtgggt tgctcacatc agaaggcaaa gagatcaaaa ataaagacga gatcttggcc     1860
ctactaaaag ccctctttct gcccaaaaga cttagcataa tccattgtcc aggacatcaa     1920
aagggacaca gcgccgaggc tagaggcaac cggatggctg accaagcggc ccgaaaggca     1980
gccatcacag agactccaga cacctctacc ctcctcata                            2019
```